(12) United States Patent
Mueller et al.

(10) Patent No.: US 8,680,239 B2
(45) Date of Patent: Mar. 25, 2014

(54) USE OF RGM AND ITS MODULATORS

(75) Inventors: Bernhard K. Mueller, Neustadt (DE); Paolo Macchi, Tubingen (DE); Friedrich Bonhoeffer, Tubingen (DE); Bernd Stahl, Tubingen (DE); Matthias Mann, Odense M (DK); Jens S. Andersen, Odense M (DK); Philippe P. Monnier, Toronto (CA)

(73) Assignee: Max-Planck-Gesellschaft zur Foerderung der Wissenschaften E.V., Munich (DE)

( * ) Notice: Subject to any disclaimer, the term of this patent is extended or adjusted under 35 U.S.C. 154(b) by 0 days.

(21) Appl. No.: 13/493,005

(22) Filed: Jun. 11, 2012

(65) Prior Publication Data

US 2013/0072667 A1    Mar. 21, 2013

Related U.S. Application Data

(63) Continuation of application No. 12/939,823, filed on Nov. 4, 2010, now abandoned, which is a continuation of application No. 10/451,586, filed as application No. PCT/EP01/15289 on Dec. 21, 2001, now Pat. No. 7,981,420.

(30) Foreign Application Priority Data

Dec. 22, 2000 (EP) .................................. 00128356

(51) Int. Cl.
C07K 14/705    (2006.01)
C07K 14/46     (2006.01)
C07K 14/465    (2006.01)
C07K 14/435    (2006.01)

(52) U.S. Cl.
USPC ........................................................ 530/350

(58) Field of Classification Search
None
See application file for complete search history.

(56) References Cited

U.S. PATENT DOCUMENTS

| | | |
|---|---|---|
| 4,394,448 A | 7/1983 | Szoka, Jr. et al. |
| 4,399,216 A | 8/1983 | Axel et al. |
| 4,510,245 A | 4/1985 | Cousens et al. |
| 4,526,938 A | 7/1985 | Churchill et al. |
| 4,554,101 A | 11/1985 | Hopp |
| 4,634,665 A | 1/1987 | Axel et al. |
| 4,704,692 A | 11/1987 | Ladner |
| 4,816,397 A | 3/1989 | Boss et al. |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,241,070 A | 8/1993 | Law et al. |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,490 A | 6/1996 | Erickson et al. |
| 5,525,524 A | 6/1996 | Buechler et al. |
| 5,530,101 A | 6/1996 | Queen et al. |
| 5,541,109 A | 7/1996 | Searfoss, III et al. |
| 5,543,524 A | 8/1996 | Mattingly et al. |
| 5,545,806 A | 8/1996 | Lonberg et al. |
| 5,565,332 A | 10/1996 | Hoogenboom et al. |
| 5,565,352 A | 10/1996 | Hochstrasser et al. |

(Continued)

FOREIGN PATENT DOCUMENTS

DE    102008014880    9/2009
EA    008253 B1    4/2007

(Continued)

OTHER PUBLICATIONS

Osada N. et al. (Jul. 2000) Isolation of full-length cDNA clones from macaque brain cDNA libraries. Uniprot Accession No. Q9N0A6. Submitted Jul. 2000, Last sequence update Oct. 1, 2000.*

(Continued)

*Primary Examiner* — Kimberly A Ballard

(74) *Attorney, Agent, or Firm* — Lisa V. Mueller; Michael Best & Friedrich LLP

(57) ABSTRACT

The present invention relates to the use of a modulator of a polypeptide having or comprising an amino acid sequence as disclosed herein or of a functional fragment or derivative thereof or of a polynucleotide encoding said polypeptide or fragment or derivative for the preparation of a pharmaceutical composition for preventing, alleviating or treating diseases or conditions associated with the degeneration or injury of vertebrate nervous tissue, associated with seizures or associated with angiogenic disorders or disorders of the cardio-vascular system.

5 Claims, 13 Drawing Sheets

(56) References Cited

U.S. PATENT DOCUMENTS

Figure 1A:
Figure 1A:
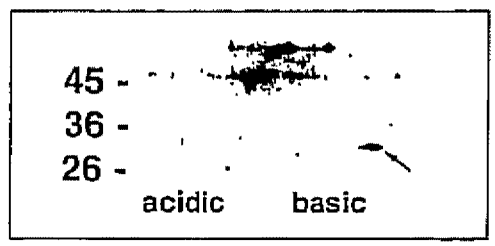
Figure 1B:
Figure 1B:
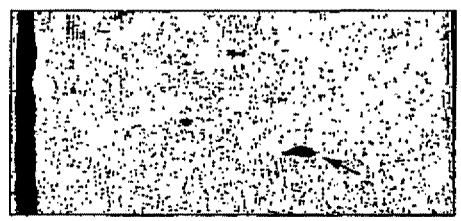
Figure 1C:
Figure 1C:
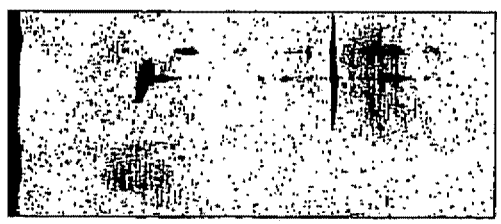
Figure 2A:
Figure 2A:
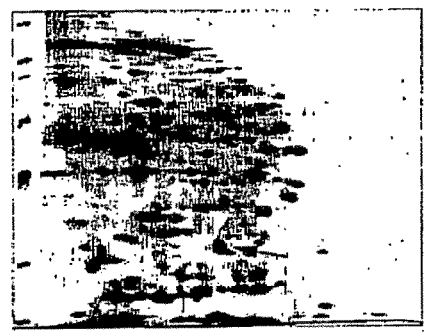
Figure 2A:
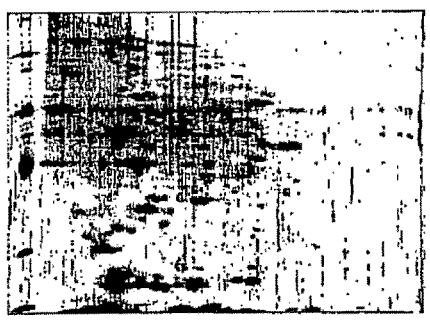
Figure 2A:
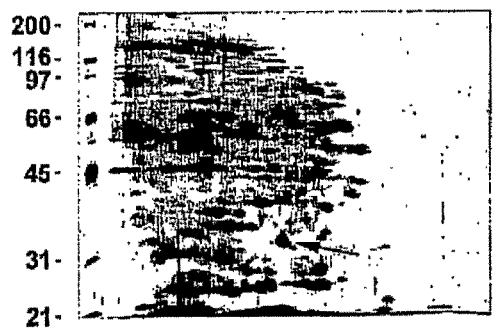

| | | |
|---|---|---|
| 5,565,362 A | 10/1996 | Rosen |
| 5,569,825 A | 10/1996 | Lonberg et al. |
| 5,571,698 A | 11/1996 | Ladner et al. |
| 5,573,904 A | 11/1996 | Mattingly |
| 5,580,717 A | 12/1996 | Dower et al. |
| 5,580,859 A | 12/1996 | Felgner et al. |
| 5,585,089 A | 12/1996 | Queen et al. |
| 5,593,896 A | 1/1997 | Adamczyk et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits et al. |
| 5,723,323 A | 3/1998 | Kauffman et al. |
| 5,733,743 A | 3/1998 | Johnson et al. |
| 5,747,262 A | 5/1998 | Hinck et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,837,500 A | 11/1998 | Ladner et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,877,397 A | 3/1999 | Lonberg et al. |
| 5,885,527 A | 3/1999 | Buechler et al. |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,994,619 A | 11/1999 | Stice et al. |
| 5,998,209 A | 12/1999 | Jokobovits et al. |
| 6,004,746 A | 12/1999 | Brent et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,087,326 A | 7/2000 | Hinck et al. |
| 6,091,001 A | 7/2000 | Jakobovits et al. |
| 6,096,311 A | 8/2000 | Fanger et al. |
| 6,111,166 A | 8/2000 | van de Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,350,861 B1 | 2/2002 | Co et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,682,928 B2 | 1/2004 | Keler et al. |
| 6,699,658 B1 | 3/2004 | Wittrup et al. |
| 6,864,239 B2 | 3/2005 | Peri et al. |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,094,761 B2 | 8/2006 | Peri et al. |
| 7,265,212 B2 | 9/2007 | Babcook et al. |
| 7,288,253 B2 | 10/2007 | Roskos et al. |
| 7,368,531 B2 * | 5/2008 | Rosen et al. ................ 530/350 |
| 7,439,063 B2 | 10/2008 | Digicaylioglu et al. |
| 7,498,034 B2 | 3/2009 | Bicknell et al. |
| 7,504,225 B2 | 3/2009 | Ring et al. |
| 7,524,492 B2 | 4/2009 | Sharma |
| 7,582,440 B2 | 9/2009 | Bicknell et al. |
| 7,612,181 B2 | 11/2009 | Wu et al. |
| 7,612,183 B2 | 11/2009 | Ellis et al. |
| 7,659,370 B2 | 2/2010 | Woolf et al. |
| 7,696,155 B2 | 4/2010 | Woolf et al. |
| 7,696,156 B2 | 4/2010 | Woolf et al. |
| 7,771,952 B2 | 8/2010 | Strittmatter et al. |
| 7,951,369 B2 | 5/2011 | Goldenberg et al. |
| 7,968,091 B2 | 6/2011 | Woolf et al. |
| 7,968,520 B2 | 6/2011 | Woolf et al. |
| 7,981,415 B2 | 7/2011 | Staunton et al. |
| 7,981,416 B2 | 7/2011 | Hardy et al. |
| 7,981,420 B2 | 7/2011 | Mueller et al. |
| 7,999,072 B2 | 8/2011 | Plouét et al. |
| 8,017,115 B2 | 9/2011 | Irving et al. |
| 2002/0110804 A1 * | 8/2002 | Stanton et al. ................ 435/5 |
| 2002/0136725 A1 | 9/2002 | Blackburn et al. |
| 2002/0137134 A1 | 9/2002 | Gerngross |
| 2003/0009152 A1 | 1/2003 | O'Hara et al. |
| 2003/0087394 A1 | 5/2003 | Sharma |
| 2003/0170881 A1 | 9/2003 | Davis et al. |
| 2003/0186374 A1 | 10/2003 | Hufton et al. |
| 2003/0212001 A1 | 11/2003 | Peri et al. |
| 2003/0235584 A1 | 12/2003 | Kloetzer et al. |
| 2004/0009491 A1 | 1/2004 | Birse et al. |
| 2004/0018577 A1 | 1/2004 | Emerson Campbell et al. |
| 2004/0018590 A1 | 1/2004 | Gerngross et al. |
| 2004/0038292 A1 | 2/2004 | Burslem et al. |
| 2004/0071711 A1 | 4/2004 | Bicknell et al. |
| 2004/0092444 A1 | 5/2004 | Digicaylioglu et al. |
| 2004/0102376 A1 | 5/2004 | Mueller et al. |
| 2005/0013809 A1 | 1/2005 | Owens et al. |
| 2005/0042664 A1 | 2/2005 | Wu et al. |
| 2005/0054078 A1 | 3/2005 | Miller et al. |
| 2005/0058649 A1 | 3/2005 | Landes et al. |
| 2005/0059604 A1 | 3/2005 | Peri et al. |
| 2005/0142137 A1 | 6/2005 | Gallo et al. |
| 2005/0197284 A9 | 9/2005 | Digicaylioglu et al. |
| 2006/0003391 A1 | 1/2006 | Ring et al. |
| 2006/0063208 A1 | 3/2006 | Woolf et al. |
| 2006/0104968 A1 | 5/2006 | Bookbinder et al. |
| 2006/0160164 A1 | 7/2006 | Miller et al. |
| 2006/0252101 A1 | 11/2006 | Strittmatter |
| 2006/0292613 A1 | 12/2006 | Peri et al. |
| 2007/0025913 A1 | 2/2007 | Bicknell et al. |
| 2007/0071675 A1 | 3/2007 | Wu et al. |
| 2007/0122491 A1 | 5/2007 | Lyons et al. |
| 2007/0155687 A1 | 7/2007 | Lyons et al. |
| 2007/0166711 A1 | 7/2007 | Samuels et al. |
| 2007/0253946 A1 | 11/2007 | Yamashita et al. |

(56) References Cited

U.S. PATENT DOCUMENTS

| | | |
|---|---|---|
| 2008/0004255 A1 | 1/2008 | Lyons et al. |
| 2008/0008692 A1 | 1/2008 | Lyons et al. |
| 2008/0020401 A1 | 1/2008 | Grenier et al. |
| 2008/0081337 A1 | 4/2008 | Sharma |
| 2008/0105705 A1 | 5/2008 | Schmidt |
| 2008/0135582 A1 | 6/2008 | Schmidt |
| 2008/0145359 A1 | 6/2008 | Bicknell et al. |
| 2008/0160034 A1 | 7/2008 | Brennan et al. |
| 2008/0181897 A1 | 7/2008 | Ni et al. |
| 2008/0213791 A1 | 9/2008 | Freije et al. |
| 2008/0219924 A1 | 9/2008 | Bicknell et al. |
| 2008/0274045 A9 | 11/2008 | Bicknell et al. |
| 2008/0279859 A1 | 11/2008 | Mezler et al. |
| 2009/0012628 A1 | 1/2009 | Shortkroff et al. |
| 2009/0017039 A1 | 1/2009 | Mi et al. |
| 2009/0028852 A1 | 1/2009 | Herrera et al. |
| 2009/0054984 A1 | 2/2009 | Shortkroff et al. |
| 2009/0069903 A1 | 3/2009 | Shortkroff et al. |
| 2009/0093409 A1 | 4/2009 | Digicaylioglu et al. |
| 2009/0123413 A1 | 5/2009 | Hardy et al. |
| 2009/0191118 A1 | 7/2009 | Young et al. |
| 2009/0191572 A1 | 7/2009 | Bicknell et al. |
| 2009/0220588 A1 | 9/2009 | Edelman et al. |
| 2009/0220589 A1 | 9/2009 | Trieu et al. |
| 2009/0227502 A1 | 9/2009 | Goldberg et al. |
| 2009/0252742 A1 | 10/2009 | Bergstein |
| 2009/0252748 A1 | 10/2009 | Mi et al. |
| 2009/0269356 A1 | 10/2009 | Epstein et al. |
| 2009/0280116 A1 | 11/2009 | Smith et al. |
| 2009/0297527 A1 | 12/2009 | Muller et al. |
| 2009/0304693 A1 | 12/2009 | Ghayur et al. |
| 2009/0311253 A1 | 12/2009 | Ghayur et al. |
| 2010/0004431 A1 | 1/2010 | Bernett et al. |
| 2010/0015665 A1 | 1/2010 | Latham et al. |
| 2010/0028340 A1 | 2/2010 | Mueller et al. |
| 2010/0036091 A1 | 2/2010 | Robinson et al. |
| 2010/0036502 A1 | 2/2010 | Svrluga et al. |
| 2010/0041139 A1 | 2/2010 | Goldberg |
| 2010/0047239 A1 | 2/2010 | Wu et al. |
| 2010/0068803 A1 | 3/2010 | Goldberg |
| 2010/0099103 A1 | 4/2010 | Hsieh et al. |
| 2010/0105569 A1 | 4/2010 | Hsieh et al. |
| 2010/0111967 A1 | 5/2010 | Baehner et al. |
| 2010/0150918 A1 | 6/2010 | Kufer et al. |
| 2010/0168393 A1 | 7/2010 | Clube et al. |
| 2010/0183588 A1 | 7/2010 | Plouet et al. |
| 2010/0183608 A1 | 7/2010 | Woolf et al. |
| 2010/0183631 A1 | 7/2010 | Rothe et al. |
| 2010/0184033 A1 | 7/2010 | West et al. |
| 2010/0249039 A1 | 9/2010 | Zangemeister-Wittke et al. |
| 2010/0254979 A1 | 10/2010 | Staunton et al. |
| 2010/0286048 A1 | 11/2010 | Rosen et al. |
| 2010/0297121 A1 | 11/2010 | Mi |
| 2010/0310573 A1 | 12/2010 | Nakagawa et al. |
| 2010/0322948 A1 | 12/2010 | Mueller et al. |
| 2011/0003971 A1 | 1/2011 | Strittmatter et al. |
| 2011/0020221 A1 | 1/2011 | Berman et al. |
| 2011/0070156 A1 | 3/2011 | Govindan et al. |
| 2011/0110852 A1 | 5/2011 | Miller et al. |
| 2011/0110936 A1 | 5/2011 | Nam et al. |
| 2011/0112280 A1 | 5/2011 | Mueller et al. |
| 2011/0117085 A1 | 5/2011 | Rotem-Yehudar et al. |
| 2011/0135657 A1 | 6/2011 | Hu et al. |
| 2011/0135664 A1 | 6/2011 | Mueller |
| 2011/0171126 A1 | 7/2011 | Burton et al. |
| 2011/0183924 A1 | 7/2011 | Mintz et al. |
| 2011/0195021 A1 | 8/2011 | Deckert et al. |
| 2011/0206671 A1 | 8/2011 | Yamashita et al. |
| 2011/0212107 A1 | 9/2011 | Goldberg et al. |
| 2011/0243841 A1 | 10/2011 | Chang et al. |
| 2011/0263827 A1 | 10/2011 | Ghayur et al. |
| 2011/0293526 A1 | 12/2011 | Plikus et al. |

FOREIGN PATENT DOCUMENTS

| | | |
|---|---|---|
| EP | 239400 | 9/1987 |
| EP | 321201 A2 | 6/1989 |
| EP | 360257 A2 | 3/1990 |
| EP | 368684 | 5/1990 |
| EP | 0368684 A1 | 5/1990 |
| EP | 404097 | 12/1990 |
| EP | 0471293 | 2/1992 |
| EP | 519596 | 12/1992 |
| EP | 0519596 A1 | 12/1992 |
| EP | 229246 B1 | 8/1993 |
| EP | 592106 | 4/1994 |
| EP | 592106 A1 | 4/1994 |
| EP | 291533 B1 | 10/1995 |
| EP | 0963376 A1 | 12/1999 |
| EP | 1176195 A1 | 1/2002 |
| EP | 1347046 | 9/2003 |
| EP | 1396543 | 3/2004 |
| EP | 1440981 | 7/2004 |
| EP | 1677113 | 7/2006 |
| EP | 1733737 | 12/2006 |
| EP | 2033971 | 3/2009 |
| EP | 2260055 | 12/2010 |
| GB | 8901334 | 5/1990 |
| GB | 9101134 | 1/1992 |
| GB | 9201755 | 4/1993 |
| GB | 2456390 | 7/2009 |
| JP | 2010065045 | 3/2010 |
| JP | 2011512806 A | 4/2011 |
| JP | 4986370 | 7/2012 |
| KR | 20080058021 | 6/2008 |
| RU | 2212241 C2 | 9/2003 |
| RU | 2362780 C2 | 7/2009 |
| WO | WO 90/02809 | 3/1990 |
| WO | WO 90/05144 | 5/1990 |
| WO | 9014424 A1 | 11/1990 |
| WO | 9014430 A1 | 11/1990 |
| WO | 9014443 A1 | 11/1990 |
| WO | 9105939 A1 | 5/1991 |
| WO | WO 91/05548 | 5/1991 |
| WO | 9109630 A1 | 7/1991 |
| WO | WO 91/09967 | 7/1991 |
| WO | WO 91/10737 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/09690 | 6/1992 |
| WO | WO 92/15679 | 9/1992 |
| WO | 9218619 A1 | 10/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/11236 | 6/1993 |
| WO | 9401234 A2 | 1/1994 |
| WO | WO 94/02602 | 2/1994 |
| WO | WO 94/29469 | 12/1994 |
| WO | WO 95/15982 | 6/1995 |
| WO | WO 95/20401 | 8/1995 |
| WO | WO 96/13518 | 5/1996 |
| WO | 9618978 A1 | 6/1996 |
| WO | WO 96/20698 | 7/1996 |
| WO | WO 96/33735 | 10/1996 |
| WO | WO 96/34096 | 10/1996 |
| WO | WO 97/00957 | 1/1997 |
| WO | WO 97/08320 | 3/1997 |
| WO | 9729131 A1 | 8/1997 |
| WO | WO 97/29131 | 8/1997 |
| WO | WO 97/32572 | 9/1997 |
| WO | 9744013 A1 | 11/1997 |
| WO | WO 97/44013 | 11/1997 |
| WO | 9816280 A1 | 4/1998 |
| WO | WO 98/16654 | 4/1998 |
| WO | WO 98/24893 | 6/1998 |
| WO | WO 98/25947 | 6/1998 |
| WO | WO 98/31346 | 7/1998 |

(56) References Cited

FOREIGN PATENT DOCUMENTS

| | | |
|---|---|---|
| WO | WO 98/31700 | 7/1998 |
| WO | WO 98/47343 | 10/1998 |
| WO | WO 98/49286 | 11/1998 |
| WO | WO 98/50433 | 11/1998 |
| WO | WO 99/01047 | 1/1999 |
| WO | WO 99/11274 | 3/1999 |
| WO | 9920253 A1 | 4/1999 |
| WO | WO 99/15154 | 4/1999 |
| WO | WO 99/20253 | 4/1999 |
| WO | WO 99/25044 | 5/1999 |
| WO | WO 99/36569 | 7/1999 |
| WO | WO 99/45031 | 9/1999 |
| WO | WO 99/45962 | 9/1999 |
| WO | 9954342 A1 | 10/1999 |
| WO | WO 99/51741 | 10/1999 |
| WO | WO 99/53049 | 10/1999 |
| WO | WO 99/66903 | 12/1999 |
| WO | WO 00/02911 | 1/2000 |
| WO | WO 00/05410 | 2/2000 |
| WO | WO 00/09560 | 2/2000 |
| WO | WO 00/14271 | 3/2000 |
| WO | WO 00/17221 | 3/2000 |
| WO | 0037504 A2 | 6/2000 |
| WO | WO 00/37504 | 6/2000 |
| WO | WO 00/56772 | 9/2000 |
| WO | WO 00/73801 | 12/2000 |
| WO | WO 0073801 | 12/2000 |
| WO | WO 01/58956 | 8/2001 |
| WO | WO 0154708 A1 * | 8/2001 |
| WO | WO 01/83525 | 11/2001 |
| WO | WO 0190304 | 11/2001 |
| WO | WO 02/02773 | 1/2002 |
| WO | WO 02/051438 | 7/2002 |
| WO | 02072636 A2 | 9/2002 |
| WO | WO 03004615 A2 * | 1/2003 |
| WO | 03016466 A2 | 2/2003 |
| WO | WO 03/031462 | 4/2003 |
| WO | 03035835 A2 | 5/2003 |
| WO | WO 03/089608 | 10/2003 |
| WO | WO 2004/003150 | 1/2004 |
| WO | WO 2004005457 | 1/2004 |
| WO | WO 2004/067561 | 8/2004 |
| WO | WO 2004/078140 | 9/2004 |
| WO | WO 2004/092405 | 10/2004 |
| WO | WO 2005016955 | 2/2005 |
| WO | WO 2005061554 | 7/2005 |
| WO | WO 2005087268 | 9/2005 |
| WO | 2005100584 A2 | 10/2005 |
| WO | WO 2006054000 | 5/2006 |
| WO | 2006066171 A1 | 6/2006 |
| WO | WO 2006088972 | 8/2006 |
| WO | WO 2006/094724 | 9/2006 |
| WO | WO 2006127861 | 11/2006 |
| WO | 2007024715 A2 | 3/2007 |
| WO | WO 2007/024715 | 3/2007 |
| WO | WO 2007039256 | 4/2007 |
| WO | WO 2007058671 | 5/2007 |
| WO | WO 2007/062852 | 6/2007 |
| WO | WO 2007106507 | 9/2007 |
| WO | WO 2007141258 | 12/2007 |
| WO | WO 2008013492 | 1/2008 |
| WO | WO 2008038599 | 4/2008 |
| WO | WO 2008073919 | 6/2008 |
| WO | WO 2008073923 | 6/2008 |
| WO | 2008082651 A2 | 7/2008 |
| WO | WO 2008085797 | 7/2008 |
| WO | WO 2008087224 | 7/2008 |
| WO | WO 2009002386 | 12/2008 |
| WO | WO 2009006543 | 1/2009 |
| WO | WO 2009026392 | 2/2009 |
| WO | WO 2009/030500 | 3/2009 |
| WO | WO 2009092032 | 7/2009 |
| WO | WO 2009094592 | 7/2009 |
| WO | WO 2009106356 | 9/2009 |
| WO | WO 2009140383 | 11/2009 |
| WO | WO 2009149185 | 12/2009 |
| WO | WO 2010006060 | 1/2010 |
| WO | WO 2010006184 | 1/2010 |
| WO | WO 2010006189 | 1/2010 |
| WO | WO 2010007144 | 1/2010 |
| WO | WO 2010017451 | 2/2010 |
| WO | WO 2010021696 | 2/2010 |
| WO | WO 2010062914 | 6/2010 |
| WO | WO 2010088688 | 8/2010 |
| WO | WO 2010105298 | 9/2010 |
| WO | WO 2010127284 | 11/2010 |
| WO | WO 2011039289 | 4/2011 |
| WO | WO 2011039734 | 4/2011 |
| WO | WO 2011068839 | 6/2011 |
| WO | WO 2011070045 | 6/2011 |
| WO | WO 2011071059 | 6/2011 |

OTHER PUBLICATIONS

International Search Report and Written Opinion for Application No. PCT/US2013/023277, mailed on Jun. 5, 2013, 21 pages.
U.S. Appl. No. 60/126,603, filed Mar. 25, 1999, Jochen Salfeld.
U.S. Appl. No. 61/142,048, filed Dec. 31, 2008, Collier et al.
A1L187—Human, Database UniProt; Feb. 6, 2007.
Adamczyk et al., Anal. Chim. Acta 579(1): 61-67 (2006).
Adamczyk et al., Bioconjugate Chem. 11: 714-724 (2000).
Adamczyk et al., Bioorg. Med. Chem. Lett. 14: 2313-2317 (2004).
Adamczyk et al., Bioorg. Med. Chem. Lett. 16: 1324-1328 (2006).
Adamczyk et al., Biorg. Med. Chem. Lett. 14: 3917-3921 (2004).
Adamczyk et al., J. Drg. Chem. 63: 5636-5639 (1998).
Adamczyk et al., Org. Lett. 1: 779-781 (1999).
Adamczyk et al., Org. Lett. 5: 3779-3782 (2003).
Adamczyk et al., Tetrahedron 55: 10899-10914 (1999).
Albert, S.E. et al. (1997) J. Immunol. 159:1393-1403.
Alberts et al. 1994. Molecular Biology of the Cell, Third Edition, pp. 1216-1220.
Amann et al., (1988) Gene 69:301-315.
Ames et al., J. Immunol. Methods 184:177-186 (1995).
Anderson, Science 256 (1992), 808-813.
Ara et al., J. Neurosci. Res. 86: 125-35, 2008.
Arai, K. et al. (1998) J. Immunol. Methods 217:79-85.
Atsushi Nagata et al., In Vivo Quantitative Evaluation of the Rat Retinal Nerve Fiber Layer with Optical Coherence Tomography, Investigative Ophthalmology & Visual Science, Jun. 2009, vol. 50, No. 6.
Ausubel et al. (eds.), Current Protocols in Molecular Biology, John Wiley & Sons, NY (1993).
Ausubel, "Short Protocols in Molecular Biology", Green Publishing Associates; and Wiley Interscience, N.Y. (1989).
Ausubel, F.M. et al., Current Protocols in Molecular Biology, Greene Publishing Assoc. and Wiley Interscience (1987).
Babcock, J.S. et al. (1996) Proc. Natl. Acad. Sci. USA 93:7843-7848.
Babitt, J.L., et al., "Bone morphogenetic protein signaling by hemojuvelin regulates hepcidin expression," Nature Genetics, vol. 38, No. 5, May 2006, pp. 531-539.
Babitt, J.L., et al., "Repulsive guidance molecule (RGMa), a DRAGON homologue, is a bone morphogenetic protein co-receptor," Journal of Biological Chemistry, vol. 280, No. 33, Aug. 2005. pp. 29820-29827.
Babitt,J.L. et al., The Journal of Clinical Investigation, 2007, vol. 117, 7, 1933-1939.
Bagnard, Development 125 (1998), 5043-5053.
Baldari et al., (1987) Embo J. 6:229-234.
Barbas et al. (1991) PNAS 88:7978-7982.
Barbas et al., Proc. Nat. Acad. Sci. USA, 91: 3809-3813 (1994).
Beaud ML et al. 2008. BMC Neurosci. 9: 5.
Becker, D., et al., (1992) "New plant binary vectors with selectable markers located proximal to the left border", Plant Mol. Biol. 20: 1195-1197.
Berrar et al., J. Comput. Biol. (2005) 12 (5),534-544.
Beschorner, Acta Neuropathol. 100 (2000), 377-384.
Better et al., Science 240:1041-1043 (1988).
Bevan, M.W. (1984) "Binary *Agrobacterium* vectors for plant transformation", Nucl. Acids Res. 12:8711-8721.

(56) References Cited

OTHER PUBLICATIONS

Bird et al. (1988) Science 242:423-426.
Blomer, J. Virology 71 (1997) 6641-6649.
Bocher, W.O. et al. (1999) Immunology 96:634-641.
Bodonszky et al., Active esters and resins in peptide synthesis. Chem Ind. Sep. 17, 1966;38:1597-8.
Bombil, F. et al. (1996) Immunobiol. 195:360-375.
Bonhoeffer & Gierer, Trends Neurosci. 7 (1984) 378-381.
Boss, M.A. and Wood, C. R. (1985) Immunology Today 6:12-13.
Braisted et al. J. Neurosci. 20: 5792-5801, 2000.
Brinkman et al., J. Immunol. Methods 182:41-50 (1995).
Brown et al. (1980) J Biol Chem 255:4980-83.
Brown et al. (1981) J. Immunol 127:539-46.
Brown, Cell 102 (2000), 77-88.
Buchwald et al., 1980, Surgery 88:507.
Burton et al., Advances in Immunology 57:191-280 (1994).
Burtrum, D., et al., "A Fully Human Monoclonal Antibody to the Insulin-Like Growth Factor I Receptor Blocks Ligand-Dependent Signaling and Inhibits Human Tumor Growth in Vivo" Cancer Research 63, Dec. 15, 2003, 8912-8921.
Camus, et al., "Molecular Evolution of Hemojuvelin and the Repulsive Guidance Molecule Family", Journal of Molecular Evolution, vol. 65, pp. 68-81 (2007).
Caroni and Schwab (Neuron 1, 85-96) 1988.
Caroni, J. Cell Biol. 106 (1988),1281-1288.
Carter et al., Proc. Natl. Acad. Sci. U.S.A. 89:4285 (1992).
Chamat, S. et al. (1999) J. Infect. Diseases 180:268-277.
Charron, J. Biol. Chem 270 (1995), 25739-25745.
Chen, Nature 403 (2000), 434-438.
Cheng et al., Clin. Exp. Med., 11:33-42 (2011).
Cheng, Cell 79 (1994), 157-168.
Chi H. E. Ma et al., The BMP Coreceptor RGMb Promotes While the Endogenous BMP Antagonist Noggin Reduces Neurite Outgrowth and Peripheral Nerve Regeneration by Modulating BMP Signaling, The Journal of Neuroscience, Dec. 14, 2011, 31(50):18391-18400.
Chothia & Lesk, J. Mol. Biol. 196:901-917 (1987).
Chothia et al., J. Mol. Biol. 227:799-817 (1992).
Chothia et al., Nature 342:877-883 (1989).
Christopher J. Severyn et al., Molecular biology, genetics and biochemistry of the repulsive guidance molecule family, Biochem. J. (2009) 422, 393-403.
Clarkson et al. (1991) Nature 352:624-628.
Cleek et al., 1997, "Biodegradable Polymeric Carriers for a bFGF Antibody for Cardiovascular Application," Pro. Int'l. Symp. Control. Rel. Bioact. Mater. 24:853-854.
Colombian Opposition, Colombia Application No. 1 0 117825, dated Aug. 22, 2011, pp. 1-6.
Conrad et al. (1998) Plant Mol. Biol. 38:101-109.
Conrad S. et al., J. Biol. Chem. 282: 16423-16433, 2007.
Corder et al., Science 261: 921 (1993).
Cox, Neuron 4 (1990), 31-7.
Cramer et al. (1999) Cuff. Top. Microbol. Immunol 240:95-118.
David, Science 214 (1981), 931-933.
Davis (1994), Science 266, 816-819.
Divry, P., J. Neurol. Psych. 27: 643-657 (1927).
Drescher, Cell 82 (1995), 359-70.
During et al., 1989, Ann. Neurol. 25:351.
Eduard Resch et al., Long signal peptides of RGMa and DCBLD2 are dissectible into subdomains according to the NtraC model, Mol. BioSyst., 2011, 7, 942-951.
Eren, R. et al. (1998) Immunology 93:154-161.
Famulok, Curro Op. Chem. Biol. 2 (1998), 320-327.
Fanger et al. Immunol Methods 4: 72-81 (1994).
Fazeli, A. et al. Phenotype of mice lacking functional Deleted in colorectal cancer (Dec) gene. Nature 386, 796-804 (1997).
Feldheim et al., Genetic analysis of ephrin-A2 and ephrin-A5 shows their requirement in multiple aspects of retinocollicular mapping. Neuron 25 (2000), 563-74.
Feldheim, Neuron 21 (1998), 1303-1313.
Feys et al., Haematologica 2007, vol. 92, 913-20.
Fishwild, D. M. et al. (1996) Nature Biotechnology 14:845-851.
Fitzgerald, D.P. et al., Neogenin is expressed on neurogenic and gliogenic progenitors in . . . Gene Expr. Pattern (2007), 7:784-792.
Fitzgerald, et al., Characterization of neogenin-expressing neural progenitor populations and migrating neuroblasts in the embryonic mouse forebrain, Neuroscience (2006), 142(3): 703-16.
Flanagan, Ann. Rev. Neurosc. 21 (1998), 309-345.
Foote and Winter 1992, J. Mol. Biol. 224:487-499.
Fournier, A. E., GrandPre, T. & Strittmatter, S. M. Identification of a receptor mediating Nogo-66 inhibition of axonal regeneration. Nature 409, 341-6 (2001).
Frisen, J. et al., "Ephrin-A5 (AL-1/RAGS) is essential for proper retinal axon guidance and topographic mapping in the mammalian visual system" Neuron 20 (1998), 235-243.
FTO RGM-A Sequence search dated Feb. 15, 2010.
Fuchs et al. (1991) Bio/Technology 9:1369-1372.
Funaro et al., BMC Biotechnology, 2008(8):85.
G. Galfre et al. (1977) Nature 266:550-52.
Gallo, M.L. et al.(2000) Eur. J. Immunol. 30:534-540.
Ganz, T., Blood, 117:4425-33, 2011.
Garrad et al. (1991) Bio/Technology 9:1373-1377.
Gavilondo JV., and Larrick J.W. (2000) BioTechniques 29:128-145.
Geddes, Front Neuroendocrinol. 20 (1999), 296-316.
Geddes, Nat. Med. 3 (1997), 1402-1404.
Gefter et al. (1977) Somatic Cell Genet., 3:231-36.
Geisbrecht, B. V., et al. Netrin binds discrete subdomains of DCC and UNC5 and mediates interactions between DCC and heparin. J Bioi Chem (2003).
GenomeQuest—Sequence Search Report result Feb. 15 11:32 am dated Feb. 15, 2010.
GenomeQuest—Sequence Search Report result Feb. 15 11:32 am dated Feb. 15, 2010 (redo 1).
Gheith, M., et al., Managing refractory glaucoma with a fixed combination of bimatoprost (0.03%) and timolol (0.5%), Clinical Ophthalmology, 2008, 2(1), pp. 15-19.
Giege, R. et al., Crystallization of Nucleic Acids and Proteins, a Practical Approach, 2nd ed., pp. 201-216, Oxford University Press, New York, New York, (1999).
Gierer, Development 101 (1987),479-489.
Giger RJ et al. 2008. Restorative Neurol Neurosci. 26: 97-115.
Gillies et al., (1989) J. Immunol Methods 125:191-202.
Giordano, Nature Medicine 2 (1996), 534-539.
Gisin, Helv. Chim. Acta. 56: 1467 (1973).
Glenner, G. N. Eng. J. Med. 302: 1283-1333 (1980).
Goeddel, Gene Expression Technology: Methods in Enzymology 185, Academic Press, San Diego, CA (1990).
Gold, Ann. Rev. Biochem. 64 (1995), 763-797.
Goldspiel et al., 1993, Clinical Pharmacy 12:488-505.
Goodhill, Neuron 25 (2000), 501-503.
Goodman, Annu. Rev. Neurosci. 19 (1996),341-77.
Goodson, in Medical Applications of Controlled Release, supra, vol. 2, pp. 115-138 (1984).
Graham, "Greenfield's Neuropathology." D.I. Graham and P.L. Lantos (eds), 6th. Edn., Edward Arnold, London (1996), pp. 197-248.
Gram et al. (1992) PNAS 89:3576-3580.
GrandPre, Nature 403 (2000), 439-444.
Gray et al. (1995) J. Imm. Meth. 182:155-163.
Green and Jakobovits, J. Exp. Med., 188: 483-495 (1998).
Green et al. Nature Genetics 7:13-21 (1994).
Green, L.L. (1999) J. Immunol. Methods 231:11-23.
Griffiths et al. (1993) EMBO J 12:725-734.
Guanghui Zhang et al., Electrical stimulation of olfactory bulb downregulates RGMa expression after ischemia/reperfusion injury in rats, Brain Research Bulletin 86 (2011) 254-261.
Halbrooks, P.J., et al. "Role of RGM coreceptors in bone morphogenetic protein signaling," Journal of Molecular Signaling, vol. 2, Jul. 5, 2007, pp. 1-10.
Hall and Miller, J. Neurosci. Res. 76 18, 2004.
Hammerling, et al., in: Monoclonal Antibodies and T-Cell Hybridomas 563-681 (Elsevier, NY., 1981).
Hanes et al. (1997) Proc. Natl. Acad. Sci. USA, 94:4937-4942.
Hanes et al. (1998) Proc. Natl. Acad. Sci. USA, 95:14130-14135.

(56) References Cited

OTHER PUBLICATIONS

Harding, F.A. and Lonberg, N. (1995) Ann. N.Y. Acad. Sci. 764:536-546.
Harel, N., et al., "Can Regenerating Axons Recapitulate Developmental Guidance During Recovery from Spinal Cord Injury?," Nature Reviews—Neuroscience, 2006, vol. 7 (8), pp. 603-616.
Harlow and Lane "Antibodies, A Laboratory Manual", CSH Press, Cold Spring Harbor, 1988.
Hata et al., 2006, Journal of Cell Biology, 173(1): 47-58.
Haugland, Handbook of Fluorescent Probes and Research Chemicals (1996).
Hawkins et al. (1992) J Mol Biol 226:889-896.
Hay et al. (1992) Hum Antibod Hybridomas 3:81-85.
Heard, C. et al. (1999) Molec. Med. 5:35-45.
Hentze et. al. (2010) Cell 142:24-38.
Herz, U. et al. (1997) Int. Arch. 30 Allergy Immunol. 113:150-152.
Heukeshoven et al., Electrophoresis 1988, 9, 28-32.
Heukeshoven et al., Electrophoresis 1988, 9, 60-61.
Higgins DG, Sharp PM. Fast and sensitive multiple sequence alignments on a microcomputer. Comput Appl. Biosci. Apr. 1989;5(2):151-1.
Highsmith W.E., (2002) Clin. Biochem. 35:425-445.
Holliger, P., et al. (1993) Proc. Natl. Acad. Sci. USA 90:6444-6448.
Hong, K. et al. A ligand-gated association between cytoplasmic domains of UNC5 and DCC family receptors converts netrin-induced growth cone attraction to repulsion. Cell 97, 927-41 (1999).
Hood et al., Adv. Exp. Med. Biol. (1999) 464:127-147.
Hoogenboom et al. (1991) Nuc Acid Res 19:4133-4137.
Hoogenboom H., and Chames P. (2000) Immunology Today 21:371-378.
Hoogenboom HR., (1997) T1B Tech. 15:62-70.
Horsley, M.B., "Retinal nerve fiber layer thickness in patients receiving chronic anti-vascular endothelial growth factor therapy," American Journal of Ophthalmology, Oct. 2010, vol. 150, No. 4, pp. 558-561.
Howard et al., 1989, J. Neurosurg. 7 1:105.
Huang et al., The Journal of Clinical Investigation (2005), 115, 2087-2091.
Hue et al., Clinical Cancer Research (2001) 7, 2213-2221.
Hunt D et al. 2002. J Neurocytol. 31: 93-120.
Hurrel, ed., "Monoclonal Hybridoma Antibodies: Techniques and Applications", CRC Press Inc., Boco Raron, FL (1982).
Huse et al. (1989) Science 246:1275-1281.
Huston et al. (1988) Proc. Natl. Acad. Sci. USA 85:5879-5883.
Huston et al., Methods in Enzymology 203:46-88 (1991).
Hutchins, W.A. et al. (1999) Hybridoma 18:121-129.
Ike et al. (1983) Nucleic Acids Res. 11:477.
Ilan, E. et al. (1999) Hepatology 29:553-562.
Iseda T et al. 2008. J Neurotrauma. 25: 334-349.
Isner, Lancet 348 (1996), 370-374.
Itakura et al. (1984) Annu. Rev. Biochem. 53:323-356.
Itakura et al., (1984) Science 198:1056-1063.
Jackson et al., J. Immunol., 154(7): 3310-3319 (1995).
Jacobi, Oncogene 19 (2000), 2052-2059.
Jaya P. Gnana-Prakasam et al., Iron-mediated retinal degeneration in hemojuvelin knockout mice, Biochemical Journal Immediate Publication. Published on Sep. 26, 2011.
Jens Schmidtmer et al., Isolation and expression pattern of three mouse homologues of chick Rgm, Gene Expression Patterns 4 (2004) 105-110.
Jin Li et al., Potential Prognostic Value of Repulsive Guidance Molecules in Breast Cancer, Anticancer Research 31: 1703-1712 (2011).
Jin Li et al., Repulsive guidance molecule B (RGMB) plays negative roles in breast cancer by coordinating BMP signaling, Journal of Cellular Biochemistry, 2012.
Jin Li et al., Repulsive guidance molecules, novel bone morphogenetic protein co-receptors, are key regulators of the growth and aggressiveness of prostate cancer cells, International Journal of Oncology 40: 544-550, 2012.
Johnnson, B., et al. (1991) Anal. Biochem. 198:268-277.
Johnnson, B., et al. (1995) J. Mol. Recognit. 8:125-131.
Joliot et al., 1991, Proc. Natl. Acad. Sci. USA 88:1864-1868.
Jönsson, U. et al. (1991) Biotechniques 11:620-627.
Jönsson, U. et al. (1993) Ann. Biol. Clin. 51:19-26.
Judit Oldekamp et al., Expression pattern of the repulsive guidance molecules RGM A, B and C during mouse development, Gene Expression Patterns 4 (2004) 283-288.
Kabat et al. (1971) Ann. NY Acad, Sci. 190:382-391.
Kabat et al., Sequences of Proteins of Immunological Interest (National Institutes of Health, Bethesda, Md. (1987).
Kabat et al., Sequences of Proteins of Immunological Interest (National Institutes of Health, Bethesda, Md. (1991).
Kalimo, Greenfield's Neuropathology 6th. Edn. Arnold, London Sydney Auckland (1996), pp. 315-381.
Kato, Brain Pathol., 10 (2000), 137-143.
Kaufman and Sharp, J. Mol. Biol., 159: 601-621 (1982).
Kaufman et al. (1987) EMBO J. 6:187-193.
Keeling SL, et al., "Mouse Neogenin, a DCC-like molecule, has four splice variants and is expressed widely in the adult mouse and during embryogenesis." Oncogene. Aug. 7, 1997;15(6):691-700.
Keino-Masu et al. Cell, 87(2) :175-185, 1996.
Kellermann S-A. et al., (2002) Current Opinion in Biotechnology 13:593-597.
Kenneth, in Monoclonal Antibodies: A New Dimension in Biological Analyses, Plenum Publishing Corp., New York, New York (1980).
Kenny et al. (1995) Bio/Technol. 13:787-790.
Kettleborough et al., Eur. J. Immunol. 24:952-958 (1994).
Khachaturian, Arch. Neurol., supra (1985).
Kipriyanov, S.M., et al. (1994) Mol. Immunol. 31 :1047-1058.
Kipriyanov, S.M., et al. (1995) Human Antibodies and Hybridomas 6:93-101.
Kirschner et al., PNAS 83: 503 (1986).
Kitayama et al., PLoS One, (2011) Vol. 6 (9), pp. 1-9.
Klemens Konig et al., The Axonal Guidance Receptor Neogenin Promotes Acute Inflammation, PLoS ONE, Mar. 2012, vol. 7, Issue 3.
Knappik et al. (2000) J. Mol. Biol. 296:57-86.
Koeberle, P.D., et al., "The repulsive guidance molecule, RGMa, promotes retinal ganglion cell survival in vitro and in vivo," Neuroscience, 169 (2010), pp. 495-504.
Kohler and Milstein, Nature 256 (1975), 494-497.
Kolodkin Cell 75 (1993) 1389-99.
Kontermann and Dubel eds., Antibody Engineering (2001) Springer-Verlag. New York. 790 pp. (ISBN 3-540-41354-5).
Korchynskyi and ten Dijke (1. Biol. Chem. 2002, 277:4883).
Kriegler, Gene Transfer and Expression, A Laboratory Manual, Stockton Press, NY (1990).
Kuby 1997. Immunology, Third Edition, pp. 131-134.
Kurjan and Herskowitz (1982) Cell 30:933-943.
Kyoto, et al., "Synapse formation of the cortico-spinal axons is enhanced by RGMa inhibition after spinal cord injury," Brain Research (2007), 1186:74-86.
Kyte et al., J. Mol. Biol. 157: 105-132 (1982).
Lah et al., Dual roles of the chemorepellent axon guidance molecule RGMa in establishing pioneering axon tracts and neural fate decisions in embryonic vertebrate forebrain, Developmental Neurobiology, 2012.
Lah et al., Novel roles of the chemorepellent axon guidance molecule RGMa in cell migration and adhesion, Mol. Cell. Biol., Jan. 3, 2012.
Lai et al., Neuroreport 8: 2691-94, 1997.
Lam et al., 1997, "Microencapsulation of Recombinant Humanized Monoclonal Antibody for Local Delivery," Proc. Int'l. Symp. Control Rel. Bioact. Mater. 24:759-760.
Langer 1990, Science 249:1527-1533.
Langer and Wise (eds.), CRC, Medical Applications of Controlled Release, Pres., Boca Raton, Fla. (1984).
Langer et al., Chemical and physical Structure of Polymer as Carriers for Controlled Release of Bioactive Agents: A Review, JMS-Rev. Macromol. Chem. Phys., C23(1), 61-126 (1983).
Leader, K.A. et al. (1992) Immunology 76:229-234.
Leonardo P. Capelli et al., Deletion of the RMGA and CHD2 genes in a child with epilepsy and mental deficiency, European Journal of Medical Genetics, 2012, 1-3.
Lerner (1981) Yale J. Biol. Med., 54:387-402.

(56) References Cited

OTHER PUBLICATIONS

Letter dated Dec. 23, 1998 from Bernhard Mueller to Dr. Thomas Hesse reporting on the results of research performed during a sabbatical relating to RGM during Jul. 29, 1998 to Sep. 6, 1998. (English translation).
Levy et al., 1985, Science 228:190.
Lingor et al. J. Neurochem, 2007.
Little M. et al. (2000) Immunology Today 21:364-370.
Logeart-Avramoglou D, et al., An assay for the determination of biologically active bone morphogenetic proteins using cells transfected with an inhibitor of differentiation promoter-luciferase construct. Anal Biochem 2006; 349:78-86.
Lonberg, N. and Huszar, D. (1995) Int. Rev. Immunol. 13:65-93.
Lonberg, N. et al. (1994) Nature 368:856-859.
Lorelei D. Shoemaker et al., Identification of Differentially Expressed Proteins in Murine Embryonic and Postnatal Cortical Neural Progenitors, PLoS ONE, Feb. 2010, vol. 5, Issue 2.
Lories and Luyten, Cytokine & Growth Factor Reviews 2005, vol. 16, 287-298.
Luciani, N. et. al. (2011) Obesity doi:10.1038/oby.2011.12 Article.
Lucklow and Summers (1989) Virology 170:31-39.
Lunn, M.P. et al. (2000) J. Neurochem. 75:404-412.
MacCallum J Mol Biol 262(5):732-45 (1996).
MacQuitty, J.J. and Kay, R.M. (1992) Science 257:1188.
Mann et al., J. Neurol. Sci. 89:169-179 (1989).
Mann, Mech. Ageing Dev. 31: 213 (1985).
Marchalonis et al., Adv Exp Med Biol. 484: 13-30 (2001).
Mari Kitayama et al., Activated Microglia Inhibit Axonal Growth through RGMa, PLoS ONE, Sep. 2011 vol. 6 Issue 9.
Marks et al., BioTechnology, 10: 779-783 (1992).
Martinez et al. Brain Res. 894: 1-11, 2001.
Matsunaga Eiji et al: "Repulsive guidance molecule/neogenin: a novel ligand-receptor system playing multiple roles in neural development." Development, Growth & Differentiation Dec. 2004, vol. 46, No. 6, Dec. 2004, pp. 481-486.
Matsunaga Eiji et al: "RGM and its receptor neogenin regulate neuronal survival." Nature Cell Biology Aug. 2004, vol. 6, No. 8, Aug. 2004, pp. 749-755.
Matsunaga, E. et al., "Repulsive Guidance Molecule Plays Multiple Roles in Neuronal Differentiation and Axon Guidance," The Journal of Neuroscience, May 31, 2006, 26(22):6082-6088.
Matsuura et al. Biochem Biophys Res Commun., 360: 868-73, 2007.
Mattingly et al., In Luminescence Biotechnology: Instruments and Applications; Dyke, K. V. Ed.; CRC Press: Boca Raton, pp. 77-105 (2002).
Mattingly, J. Biolumin. Chemilumin. 6:107-114 (1991).
Mautes et al. Vascular events after spinal cord injury: contribution to secondary pathogenesis. Phys Ther. Jul. 2000;80(7):673-687.
McCafferty et al., Nature (1990) 348:552-554.
McCapra et al., Photochem. Photobiol. 4: 1111-21 (1965).
McNamara, Nat. Suppl. 399 (1999).
Meier (1999), J. Neuropatho J. Exp. Neurol. 58, 1099-1110.
Mendez, M. J. et al. (1997) Nature Genetics 15:146-156.
Merrifield, J. Am. Chem. Soc. 85: 2149 (1963).
Mey & Thanos, (1992); J. Hirnforschung 33, 673-702.
Meyerhardt et al. reported in Oncogene (1997) 14, 1129-1136.
Mills et al. Strain and model differences in behavioral outcomes after spinal cord injury in rat,]. Neurotrauma Aug; 18(8):743-756, 2001.
Milstein et al., Nature, 305(5934): 537-540 (1983).
Mimms et al., Virology 176 (1990), 604-619.
Ming, G. L. et al. cAMP-dependent growth cone guidance by netrin-1. Neuron 19, 1225-35 (1997).
Mirakaj et al., RGM a leukocyte migration inflammation supporting information, PNAS, 2011.
Monnier, P. P. et al. RGM is a repulsive guidance molecule for retinal axons. Nature 419, 392-395 (2002).
Monschau et al., The EMBO Journal vol. 16 No. 6 pp. 1258-1267, 1997.
Morgan and Anderson, Ann. Rev. Biochem. 62:191-217 (1993).
Mori et al., Journal of Biological Chemistry 267: 17082 (1992).
Morrison, Science 229:1202 (1985).
Mueller et al., Philos. Trans. R. Soc. Lond. B Biol. Sci. 361: 1513-1529, 2006.
Mueller, Annu. Rev. Neurosci 22, (1999), 351-88.
Muhlhauser, Circ. Res. 77 (1995), 1077-1086.
Müller et al., "RGM, a repulsive guidance molecule, is involved in retinal axon guidance in vitro." Taniguchi Symposia on Brain Sciences, vol. 20 Mol. Basis of Axon Growth & Nerve Pattern Form 1997, pp. 215-229.
Müller et al., Current Biology 1995, vol. 5 No. 11, 1255-1256.
Muller et al., Current Opinion in Genetics and Development 1996, 6:469-474.
Müller, B.K., et al., "Chromophore-assisted laser inactivation of a repulsive axonal guidance molecule," Current Biology 1996, vol. 6 No. 11: 1497-1502.
Müller, B.K., et al., "In Vitro Experiments on Axonal Guidance and Growth-Cone Collapse," J. Exp. Biol. 153, 29-46 (1990).
Mulligan, Science 260:926- 932 (1993).
Mullinax et al., BioTechniques 12(6):864-869 (1992).
Muramatsu et al., Nat. Medicine (2011) 17:488-94.
Murphy, W.J. et al. (1996) Semin. Immunol. 8.233-241.
Murphy, W.J. et al. (1999) Clin. Immunol. 90:22-27.
Nakamoto, Cell 86 (1996), 755-66.
Narang, S.A. (1983) Tetrahedron 39:3.
Nemeth, E. et. al. (2003) Blood:101:7,2461.
Neuberger et al., 1984, Nature 312:604-608.
Nguyen, H. et al. (1997) Microbiol. Immunol. 41 :901-907.
Niederkofler V. et al., J. Neurosci. 24, 808-818, 2004.
Niederkofler, V. et al. (2005) J. Clin Invest. 115:2180.
Nielsen, Science 254 (1991), 1497-1500.
Ning et al., 1996, "Intratumoral Radioimmunotherapy of a Human Colon Cancer Xenograft Using a Sustained Release Gel," Radiotherapy &Oncology 39:179-189.
Oi et al., BioTechniques 4:214 (1986).
Oldekamp J et al: "Expression pattern of the repulsive guidance molecules RGM A, B and C during mouse development" Gene Expression Patterns, Elsevier, vol. 4, No. 3, May 2004, pp. 283-288.
Padlan FASEB J. 9:133-139 (1995).
Padlan, Molecular Immunology 28 (4/5) :489-498 (1991).
Papanikolaou, G. et. al (2005) Blood 105:10,4103-4105.
Papanikolaou, G. et. al. (2004) Nat. Genet. 36:77.
Pauwels, R. (1985). Pharmacokinetics of inhaled drugs. Aerosols in Medicine. Principles, diagnosis and therapy. eds. Moren, F., Newhouse, M. T. & Dolovich, M. B. Amsterdam, New York, Oxford: Elsevier.
Pearson and Lipman, Proc. Natl. Acad, Sci. (USA) 85(8), 1988, 2444-2448.
Persic et al., Gene 187: 9-18 (1997).
Picker, Development 126 (1999), 2967-78.
Pietrangelo, J. Hepatology, 54: 173-181 (2011).
Pietta and Marshall, Chem. Comm. 650 (1970).
Polak and Van Noorden, Introduction to Immunocytochemistry, 2nd ed., Springer Verlag, N.Y. (1997).
Poljak, R.J., et al. (1994) Structure 2:1121-1123.
Postler, Glia 19 (1997), 27-34.
Powell et al. (1990) Biotechnol. 8:333-337.
Presta et al., J. Immunol. 151:2623 (1993).
Puchtler et al., J. Histochem. Cytochem. 10: 365 (1962).
Puschel, Neuron 14 (1995), 941-948.
Rajagopalan, S., et al., "Neogenin mediates the action of repulsive guidance molecule." Nat Cell Biol. 6, pp. 756-762, 2004.
Raper & Kapfhammer, Neuron 4 (1990), 21-29.
Razavi et al., Luminescence 15: 239-249 (2000).
Reifers, Development 125 (1998), 2381-95.
Reisner, Yand Dagan, S. (1998) Trends Biotechnol. 16:242-246.
Remington's Pharmaceutical Sciences and Introduction to Pharmaceutical Dosage Forms, 19th ed., Mack Pub. Co., Easton, Pa. (1995).
RGM and Retinal Neuronal Regeneration Search—Jan. 25, 2010.
RGM or RGMA or Neogenin Search—Feb. 16, 2010.
RGM—A human isoform 1 NP_001159755 Blast search dated Feb. 15, 2010.
Riechmann et al., Nature 332:323 (1988).

(56) References Cited

OTHER PUBLICATIONS

Rieko Muramatsu et al., RGMa modulates T cell responses and is involved in autoimmune encephalomyelitis, Nature Medicine, published online Mar. 20, 2011.
Roberts, R.W. and Szostak, J.W. (1997) Proc. Natl. Acad. Sci. USA 94:12297-12302.
Robinson, ed., Sustained and Controlled Release Drug Delivery Systems, Marcel Dekker, Inc., New York, 1978.
Robinson, May 1993, TIBTECH 11(5): 155.
Roes, J. et al. (1995) J. Immunol. Methods 183:231-237.
Roguska. et al. PNAS 91: 969-973 (1994).
Rosen, C.A., et al., "Therapeutic protein HARMJ38—Seq Id No. 1853", database EMBL/GENBANK/DDBJ; Jun. 15, 2006.
Routbort, Neuroscience 94 (1999), 755-765.
Ruoshlahti, Annu. Rev. Cell Dev. Biol. 12 (1996), 697-715.
Saeed et al., Arterioscler. Thromb. Vasco Biol., 32 (Feb. 2012), Accepted on Nov. 5, 2011.
Saltzman et al., Biophys. J. 55: 163 (1989).
Samad, T.A. et al., "DRAGON, a bone morphogenetic protein co-receptor," Journal of Biological Chemistry, vol. 280, No. 14, Apr. 2005, pp. 14122-14129.
Sambrook, et al., Molecular Cloning; A Laboratory Manual, 2nd Edition, Cold Spring Harbour Laboratory Press, Cold Spring Harbour, NY (1989).
Sandhu et al. (1996) Crit. Rev. Biotechnol. 16:95-118.
Santoro, Proc. Natl. Acad. Sci. USA 94 (1997), 4262.
Saudek et al., 1989, N. Engl. J. Med. 321:574.
Sawai et al., Am. J. Reprod. Immunol., 34:26-34 (1995).
Schaffar, G., et al., "Lim-only Protein 4 Interacts Directly with the Repulsive Guidance Molecule a Receptor Neogenin," Journal of Neurochemistry, 2008, vol. 107 (2), pp. 418-431.
Schaper, Circ. Res. 79 (1996), 911-919.
Schaper, Current Opinion in Biotechnology 7 (1996), 635-640.
Schier et al., Gene, 169: 147-155 (1995).
Schmidtmer, J. and D. Engelkamp (2004) Gene Exp. Patterns 4:105.
Schnell, Nature 343 (1990) 269-272.
Schnichels, S., et al., "Gene expression of the repulsive guidance moleculeslneogenin in the developing and mature mouse visual system: C57BL16J vs. the glaucoma model DBA/2J," Gene Expression Patterns, 8, (2007), pp. 1-11.
Schultz et al. (1987) Gene 54:113-123.
Schwab et al. Eur. J. Neurosci. 21:1569-1576, 2005.
Schwab J.M. et al., Arch. Neurol. in press, 62: 1561-1568, 2005.
Schwab, Acta Neuropathol. 99 (2000), 609-614.
Seed, B. (1987) Nature 329:840.
Sefton, 1987, CRC Crit. Ref. Biomed. Eng. 14:20.
Serafini, T. et al. Netrin-1 is required for commissural axon guidance in the developing vertebrate nervous system. Cell 87, 1001-14 (1996).
Setoguchi et al., Exp. Neurol. 189: 33-44, 2004.
Severyn et al., Biochem. J., 422:393-403 (2009).
Shapiro et al., Crit. Rev. Immunol. 22(3): 183-200 (2002).
Sharp, Genes and Dev. 13 (1999),139-141.
Sherwood et al., Bio/Technology 10: 1446 (1992).
Shu et al., PNAS 90:7995-7999 (1993).
Silhavy, M.L. Berman and L.W. Enquist, Experiments with Gene Fusions, Cold Spring Harbor Laboratory, Cold Spring Harbor, NY (1984).
Skerra et al., Science 240:1038-1040 (1988).
Smith et al., (1983) Mol. Cell Biol. 3:2156-2165.
Smith, D.B. and Johnson, K.S. Pharmacia Biotech Inc (1988) Gene 67:31-40.
Smithson, S.L. et al. (1999) Mol. Immunol. 36:113-124.
Smolen and Ball (eds.), Controlled Drug Bioavailability, Drug Product Design and Performance, Wiley, New York (1984).
Song et al., 1995, "Antibody Mediated Lung Targeting of Long-Circulating Emulsions," PDA Journal of Pharmaceutical Science & Technology 50:372-397.
Sperry, Proc. Natl. Acad. Sci. USA 50 (1963), 703-710.
Staerz et al., Nature, 314(2012): 628-631 (1985).

Stahl, et al., "Biochemical Characterization of a Putative Axonal Guidance Molecule of the Chick Visual System", Neuron, vol. 5, pp. 735-743 (1990).
Steenbakkers et al. (1994) Molec. Biol. Reports 19:125-134 (1994).
Steinecke, Ribozymes, Methods in Cell Biology 50, Galbraith, eds. Academic Press, Inc. (1995), 449-460.
Steward, et al. 2008. Exp Neurol. 209: 446-468.
Stewart and Young in Solid Phase Peptide Syntheses (2nd Ed., Pierce Chemical Company, 1984).
Stokes et al., Experimental modeling of human spinal cord injury: a model that crosses the species barrier and mimic the spectrum of human cytopathology, Spinal Cord 40: 101-109, 2002.
Stoll, Prog. Neurobiol. 56 (1998), 149-171.
Streit, Prog. Neurobiol. 57 (1999), 563-581.
Studier et al. Gene Expression Technology: Methods in Enzymology 185, Academic Press, San Diego, California (1990) 60-89.
Studnicka et al., Protein Engineering 7 (6) : 805-814 (1994).
Suda, M., et al., "Peptides Derived from Repulsive Guidance Molecule Act as Antagonists," Biochemical and Biophysical Research Communications, 2008, vol. 371 (3), pp. 501-504.
Sven Schnichels et al., RGMA and neogenin protein expression are influenced by lens injury following optic nerve crush in the rat retina, Graefes Arch Clin Exp Ophthalmol, 2011.
Takahide Itokazu et al., Identification of the Neogenin-Binding Site on the Repulsive Guidance Molecule A, PLoS ONE, Mar. 2012, vol. 7, Issue 3.
Takeda et al., 1985, Nature 314:452-454.
Takekazu Kubo et al., Crosstalk Between the Immune and Central Nervous Systems with Special Reference to Drug Development, 2011.
Talac et al. Animal models of spinal cord injury for evaluation of tissue engineering treatment strategies, Biomaterials 25: 1505-1510, 2004.
Tanelian, Nat. Med. 3 (1997), 1398-1401.
Tassew, N., et al., "Intraretinal RGMa is involved in retino-tectal mapping," Mol. Cell. Neurosci., 37 (2008), pp. 761-769.
Tassew, N.G. et al., "Sustained In Vivo Inhibition of Protein Domains Using Single-Chain Fv Recombinant Antibodies and Its Application to Dissect RGMa Activity on Axonal Outgrowth," The Journal of Neuroscience, Jan. 28, 2009, 29(4): 11126-1131.
Taylor, L.D. et al. (1992) Nucleic Acids Res. 20:6287-6295.
Terry et al., J. Neuropathol. Exp. Neurol 46: 262 (1987).
Tessier-Lavigne, M. & Goodman, C. S. The molecular biology of axon guidance. Science 274, 1123-1133. (1996).
Tolstoshev, Ann. Rev. Pharmacol. Toxicol. 32:573-596, (1993).
Urist et al., Prog. Clin. Biol. Res. 1985, vol. 187: 77-96.
Urlaub and Chasin, (1980) Proc. Natl. Acad. Sci. USA 77:4216-4220.
Valbona Mirakaj et al., Repulsive guidance molecule-A (RGM-A) inhibits leukocyte migration and mitigates inflammation, PNAS, Apr. 19, 2011, vol. 108, No. 16, 6555-6560.
Valbona Mirakaj et al., The guidance receptor neogenin promotes pulmonary inflammation during lung injury, The FASEB Journal, Published online Dec. 23, 2011.
van den Hondel, C.A.M.J.J. & Punt, P.J. (1991) Gene transfer systems and vector development for filamentous fungi, in: Applied Molecular Genetics of Fungi, J.F. Peberdy et al., eds, pp. 1-28, Cambridge University Press: Cambridge.
Verma, Nature 389 (1997), 239-242.
Vielmetier, J., et al. Neogenin, an Avian cell Surface Polypeptide Expressed Terminal Neuronal Differentiation, Is Closely Related to the Human Tumor Suppressor Molecule Deleted in Colorectal Cancer. J. Cell. Bio. Dec. 1994, vol. 127, No. 6, 1-12, 15-17 pp. 2009-2020.
Vielmetter, J., et al., In vitro assay to test differential substrate affinities of growing axons and migratory cells. Exp Brain Res 81, 283-7 (1990).
Voet, Voet, Biochemistry, Second Edition, p. 1361, John Wiley & Sons, Inc., 1995.
Wahl, J. Cell Biol. 149(2) (2000), 263-70.
Wallemacq et al., Evaluation of the New AxSYM Cyclosporine Assay: Comparison with TDx Monoclonal Whole Blood and EMIT Cyclosporine Assays, Clin. Chem. 45: 432-435 (1999).

(56) References Cited

OTHER PUBLICATIONS

Walter, Development 101, (1987), 685-96.
Walter, J. Physiol 84 (1990), 104-10.
Walter, J., Henke-Fable, S. & Bonhoeffer, F. Avoidance of posterior tectal membranes by temporal retinal axons. Development 101, 909-13 (1987).
Wang, H., et al., Netrin-3, a mouse homolog of human NTN2L, is highly expressed in sensory ganglia and shows differential binding to netrin receptors. J Neurosci 19, 4938-47 (1999).
Wang, Nature Medicine 2 (1996), 714-716.
Ward et al., (1989) Nature 341 :544-546.
Weinstein, D. et. al. (2002) Blood:100:10, 3776.
Weiss M.D. and Goodnough, L.T., New Engl. J. Med. 352: 1011-1022, 2005.
Wells, High Throughput Bioanalytical Sample Preparation. Methods and Automation Strategies, Elsevier (2003).
Wen et al. (1987) J. Immunol. 17:887-892.
Wilbur, W. J. and Lipman, D. J. Proc. Natl. Acad. Sci. USA 80, 726-730 (1983).
Wilm & Mann, Anal. Chem. 68 (1996), 1-8.
Wilm, Nature 379 (1996), 466-9.
Winnaker, From Genes to Clones (Verlagsgesellschaft, Weinheim, Germany 1987).
Wisniewski et al., Zimmerman, H. M. (ed.): Progress in Neuropathology (Grune and Stratton, N.Y. 1973) vol. 2, pp. 1-26.
Wu and Wu, Biotherapy 3:87-95, (1991).
Wu and Wu, J. Biol. Chem. 262:4429-4432 (1987).
Wu, C., et al., Nature Biotechnology, 25(11): 1290-1297 (2007).
Xia, Y., et al., "Localization and action of dragon (repulsive guidance molecule b), a novel bone morphogenetic protein coreceptor, throughout the reproduction axis," Endocrinology, vol. 146, No. 8, Aug. 2005, pp. 3614-3621.
Xia, Yin, et el., "Repulsive guidance molecule RGMa alters utilization of bone morphogenetic protein (BMP) type II receptors by BMP 2 and BMP 4," Journal of Biological Chemistry, vol. 282, No. 25, Jun. 2007, pp. 18129-18140.
Yamashita et al. "Neogenin and repulsive guidance molecule signaling in the central nervous system" Curr. Opin. Neurobiol. 17: 29-34, 2007.
Yang, X.D. et al. (1999) J. Leukoc. Biol. 66:401-410.
Yatscoff et al., Abbott TDx Monoclonal Antibody Assay Evaluated for Measuring Cyclosporine in Whole Blood, Clin. Chem. 36: 1969-1973 (1990).
Yeh et al. (1976) PNAS 76:2927-31.
Yeh et al. (1982) Int. J. Cancer 29:269-75.
Yelton et al., J. Immunol., 155: 1994-2004 (1995).
Yin Xia et al., Dragon (Repulsive Guidance Molecule b) Inhibits IL-6 Expression in Macrophages, J Immunol 2011;186;1369-1376; Prepublished online Dec. 27, 2010.
Yoshinari, K. and Arai, K. (1998) Hybridoma 17:41-45.
Yu, T. W. & Bargmann, C. I. Dynamic regulation of axon guidance. Nat Neurosci 4 Suppl, 1169-76 (2001).
Zapata et al. (1995) Protein Eng. 8(10): 1057-1062.
PCT/EP2001/015289 International Search Report dated May 13, 2003 (5 pages).
PCT/US2003/20147 International Search Report dated Jun. 21, 2004 (1 page).
PCT/EP2006/009497 International Search Report dated May 14, 2007 (6 pages).
International Search Report from International Patent Application Publication WO2009/030500 dated Apr. 3, 2007.
International Search Report for Application No. PCT/EP2009/001437, mailed on Jun. 18, 2009,3 pages.
International Written Opinion for Application No. PCT/EP2009/001437, issued Aug. 31, 2010, 7 pages.
Supplemental International Search Report for Application No. PCT/EP2009/001437, mailed on Apr. 8, 2010, 2 pages.
International Search Report and Written Opinion from International Patent Application No. PCT/EP2010/069120, dated Apr. 11, 2011.
International Search Report and Written Opinion from International Patent Application No. PCT/EP2008/007339 dated Sep. 2, 2009 (12 pages).
United States Patent Office Final Rejection for U.S. Appl. No. 12/939,823 dated Dec. 22, 2011 (16 pages).
United States Patent Office Action for U.S. Appl. No. 12/758,445 dated Jan. 13, 2012 (10 pages).
United States Patent Office Action for U.S. Appl. No. 12/992,720 dated Sep. 8, 2011 (11 pages).
United States Patent Office Notice of Allowance for U.S. Appl. No. 12/389,927 dated Jun. 18, 2012 (25 pages).
United States Patent Office Notice of Allowance for U.S. Appl. No. 12/389,927 dated Mar. 2, 2012 (8 pages).
United States Patent Office Final Rejection for U.S. Appl. No. 12/389,927 dated Oct. 28, 2011 (18 pages).
Mexican Patent Office Action for Application No. MX/a/2008/004108 dated Jan. 12, 2012 (4 pages—with English summary).
Israeli Patent Office Action for Application No. 207787 dated Aug. 17, 2012 (3 pages).
New Zealand Patent Office Examination Report for Application No. 587198 dated Mar. 11, 2011 (3 pages).
Hungarian Patent Office Written Opinion for Application No. 201005799-0 dated Jun. 8, 2012 (10 pages).
Japanese Patent Office Action for Application No. 2009-250440 dated Feb. 28, 2012 (6 pages—with English summary).
Japanese Patent Office Action for Application No. 2008-532684 dated Mar. 7, 2012 (11 pages—English Translation).
Chinese Patent Office Second Action for Application No. 2006800363460 dated Feb. 16, 2012 (3 pages—English Translation).
Chinese Patent Office Second Action for Application No. 200880103451 dated Aug. 9, 2012 (32 pages—with English Translation).
Canadian Patent Office Action for Application No. 2,542,171 dated Apr. 13, 2012 (2 pages).
European Patent Office Action for Application No. 08801915.3 dated Feb. 2, 2011 (4 pages).
Canadian Patent Office Action for Application No. 2,542,171 dated Feb. 7, 2011 (3 pages).
Abstracts of the XIIth International Symposium on Bioluminescence and Chemiluminescence to be Held at Robinson College, University of cambridge, England, Apr. 5-9, 2002, Luminescence, 2002, vol. 17, pp. 77-115.
Adamczyk M., et al., "Chemiluminescent N-Sulfonylacridinium-9-Carboxamides and Their Application in Clinical Assays ," Luminescence Biotechnology: Instruments and Applications , 2002, pp. 77-105.
Ausubel F.M., et al., eds., Current Protocols in Molecular Biology, 1994-1998, vol. 1, John Wiley & Sons Inc, Table of Contents.
Berzofsky J.A., "Intrinsic and Extrinsic Factors in Protein Antigenic Structure," Science, 1985, vol. 229 (4717), pp. 932-940.
Bork P., et al., "Go Hunting in Sequence Databases but Watch out for the Traps ," Trends in Genetics, 1996, vol. 12 (10), pp. 425-427.
Bork P., "Powers and Pitfalls in Sequence Analysis: The 70% Hurdle ," Genome Research, 2000, vol. 10 (4), pp. 398-400.
Bossers K., et al., "Analysis of Gene Expression in Parkinson's Disease: Possible Involvement of Neurotrophic Support and Axon Guidance in Dopaminergic Cell Death," Brain Pathology, 2009, vol. 19 (1), pp. 91-107.
Brenner S.E., "Errors in Genome Annotation ," Trends in Genetics, 1999, vol. 15 (4), pp. 132-133.
Camus L., et al., "Molecular Evolution of Hemojuvelin and the Repulsive Guidance Molecule Family," Journal of Molecular Evolution, 2007, vol. 107 (2), pp. 428-431.
Casset, F., et al., "A Peptie Mimetic of an Anti-CD4 Monoclonal Antibody by Rational Design," Biochemical and Biophysical Research Communications, 2003, vol. 307 (1), pp. 198-205.
Chen Y., et al., "Selection and Analysis of an Optimized Anti-VEGF Antibody: Crystal Structure of an Affinity-Matured Fab in Complex with Antigen," Journal of Molecular Biology , 1999, vol. 293 (4), pp. 865-881.

(56) References Cited

OTHER PUBLICATIONS

Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
De Pascalis R., et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunological Methods, 2002, vol. 169 (6), pp. 3076-3084.
Doerks T., et al., "Protein Annotation: Detective work for Function Prediction," Trends in Genetics, 1998, vol. 14 (6), pp. 248-250.
Elmer L.W., et al., "The Increasing Role of Monoamine Oxidase Type B Inhibitors in Parkinson's Disease Therapy," Expert Opinion on Pharmacotherapy, 2008, vol. 9 (16), pp. 2759-2772.
European Search Report for Application No. EP07115856, mailed on Apr. 15, 2008, 8 pages.
Final Office Action mailed Nov. 8, 2011 for U.S. Appl. No. 11/992,720, filed May 16, 2009.
Genbank Accession No. AK080819, Mar. 3, 2004.
Genbank Accession No. BCO23870, Feb. 24, 2004.
Genbank Accession No. BCO22603, Jan. 3, 2005.
Genbank Accession No. BI769500, Sep. 25, 2001.
Genbank Accession No. BI818609, Oct. 4, 2001.
Gennaro A.R., ed., Remington: The Science and Practice of Pharmacy, 19th Edition, Mack Publishing, 1995, Table of Contents.
Giege R., et al., "An Introduction to the Crystallogenesis of Biological Macromolecules" in: Crystallization of Nucleic Acids and Proteins, Chapter 1, 2nd Edition, Ducruix A., et al., Eds., Oxford University Press, 1999, pp. 1-16.
Gnana-Prakasam J.P., et al., "Iron-mediated Retinal Degeneration in Haemojuvelin-knockout Mice," The Biochemical Journal, 2012, vol. 441 (2), pp. 599-608.
Goeddel D.V., "Systems for Heterologous Gene Expression," Methods in Enzymology, 1990, vol. 185, pp. 3-7.
Graham D.I., et al., Trauma, Chapter 5, 1996, pp. 197-248.
Hammerling G.J., et al., Eds., Monoclonal Antibodies and T-Cell Hybridomas : Perspectives and Technical Advances, Elsevier/North-Holland Biomedical Press, 1981, Appendix, pp. 563-587.
Hanson L.R., et al., "Intranasal Delivery Bypasses the Blood-Brain Barrier to Target Therapeutic Agents to the Central Nervous System and Treat Neurodegenerative Disease," BMC Neuroscience, 2008, vol. 9 (Suppl 3), pp. S5.
Harlow E., et al., Antibodies: A Laboratory Manual, Cold Spring Harbor Laboratory Press, 1988, pp. 555-561, 578-582 and 591-592.
Huang FW., et al., "A Mouse Model of Juvenile Hemochromatosis," The Journal of Clinical Investigation, 2005, vol. 115 (8), pp. 2187-2191.
International Search Report and Written Opinion for Application No. PCT/EP2010/69120, mailed on May 4, 2011.
Jefferis R., "Glycosylation of Recombinant Antibody Therapeutics," Biotechnology Program, 2005, vol. 21 (1), pp. 11-16.
Jones P.T., et al., "Replacing the Complementarity-Determining Regions in a Human Antibody with those from a Mouse," Nature, 1986, vol. 321 (6069), pp. 522-525.
Jost W.H., et al., "Initial Experience with Ropinirole PR (Prolonged Release)," Journal of Neurology, 2008, vol. 255 (Suppl 5), pp. 60-63.
Kabat E.A., et al., in: Sequence of Proteins of Immunological Interest, 4th Edition, 1987, Table of Contents.
Kalimo H., et al., "Vascular Diseases", in: Greenfield's Neuropathology, Chapter 7, Graham D.I., et al., eds., Oxford University Press, 1997, pp. 315-396.
Khor S.P., et al., "The Pharmacokinetics and Pharmacodynamics of Levodopa in the Treatment of Parkinson's Disease," Current Clinical Pharmacology, 2007, vol. 2 (3), pp. 234-243.
Knoll B., et al., "Stripe Assay to Examine Axonal Guidance and Cell Migration," Nature Protocols, 2007, vol. 2 (5), pp. 1216-1224.
Lamminmaki U., et al., "Crystal Structure of a Recombinant Anti-Estradiol Fab Fragment in Complex with 17beta -Estradiol," The Journal of Biological Chemistry, 2001, vol. 276 (39), pp. 36687-36694.
Langer R.S., et al., eds., Medical Applications of Controlled Release: Applications and Evaluation, vol. 2, CRC Press, 1984, pp. 113-138.
Liang B.A., et al., "Review of Tissue Plasminogen Activator, Ischemic Stroke, and Potential Legal Issues," Archives of Neurology, 2008, vol. 65 (11), pp. 1429-1433.
Lund J., et al., "Human Fc Gamma RI and Fc Gamma RII Interact with Distinct but Overlapping Sites on Human IgG," Journal of Immunology, 1991, vol. 147 (8), pp. 2657-2662.
Monahan M.W., et al., "A Rapid Method for the Preparation of Amino Acid Resin Esters for Merrifield Solid-phase Peptide Synthesis," Biopolymers, 1973, vol. 12 (11), pp. 2513-2519.
Ngo J.T., et al., "Computational Complexity, Protein Structure Prediction, and the Levinthal Paradox," 1994, pp. 491-495.
Non-Final Office Action mailed May 27, 2011 for U.S. Appl. No. 11/992,720, filed May 16, 2009.
Office Action mailed May 25, 2012 for Chinese Application No. 200880103451 filed Sep. 8, 2008.
Opposition mailed Aug. 22, 2011 for Colombian Application No. 10117825 filed Sep. 23, 2010.
Padlan E.A., et al., "Structure of an Antibody-antigen Complex: Crystal Structure of the HyHEL-10 Fab-lysozyme Complex," Proceedings of the National Academy of Sciences, 1989, vol. 86 (15), pp. 5938-5942.
Razavi Z., et al., "Stable and Versatile Active Acridinium Esters II ," Luminescence, 2000, vol. 15, pp. 245-249.
Remington, "The Science and Practice of Pharmacy," Table of Contents, 1995.
Rudikoff S., et al., "Single Amino Acid Substitution Altering Antigen-Binding Specificity," Proceedings of the National Academy of Sciences of the United States of America, 1982, vol. 79 (6), pp. 1979-1983.
Sambrook J., et al., "Molecular Cloning," A Laboratory Manual, Second Edition, Cold Spring Harbor Laboratory Press,1989, Table of Contents.
Schier R., et al., "Identification of Functional and Structural Amino-Acid Residues by Parsimonious Mutagenesis," Gene, 1996, vol. 169 (2), 147-155.
Shields R.L., et al., "Lack of Fucose on Human IgG1 N-Linked Oligosaccharide Improves Binding to Human Fcgamma RIII and Antibody-Dependent Cellular Toxicity," The Journal of Biological Chemistry, 2002, vol. 277 (30), pp. 26733-26740.
Shoemaker L.D., et al., "Identification of Differentially Expressed Proteins in Murine Embryonic and Postnatal Cortical Neural Progenitors," PLoS One, 2010, vol. 5 (2), pp. e9121.
Sims M.J., et al., "A Humanized CD18 Antibody can Block Function without Cell Destruction," Journal of Immunology, 1993, vol. 151 (4), pp. 2296-2308.
Skolnick J., et al., "From Genes to Protein Structure and Function: Novel Applications of Computational Approaches in the Genomic Era," Trends in Biotechnology, 2000, vol. 18 (1), pp. 34-39.
Smith T.F., et al., "The Challenges of Genome Sequence Annotation or "The Devil Is In The Details"," Nature Biotechnology, 1997, vol. 15 (12), pp. 1222-1223.
Smolen V.F., et al., Eds., Controlled Drug Bioavailability, John Wiley & Sons, 1984, Table of Contents.
Sutcliffe J.G., et al., "Antibodies that React with Predetermined Sites on Proteins," Science, 1983, vol. 219 (4585), pp. 660-666.
Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.
Vajdos F.F., et al., "Comprehensive Functional Maps of the Antigen-binding Site of an Anti-ErbB2 Antibody Obtained with Shotgun Scanning Mutagenesis," Journal of Molecular Biology, 2002, vol. 320 (2), pp. 415-428.
Verhoeyen M., et al., "Reshaping Human Antibodies: Grafting an Antilysozyme Activity ," Science, 1988, vol. 239, pp. 1534-1536.
Viewing Sequence(s): 1853 of 2267 for Document # 20060084794, Publication Site for Issued and Published Sequences (PSIPS), Seq Id

(56) References Cited

OTHER PUBLICATIONS

No. 1853 [online], Jan. 2011 [Last Modified on Jan. 25, 2011]. Retrieved from the Internet:< seqdata.uspto.gov/?pagerequest=view. . . .

Voet D., et al., Biochemistry, Second Edition, John Wiley & Sons, Inc, 1995, Table of Contents.

Wallick S.C., et al., "Glycosylation of a VH Residue of a Monoclonal Antibody against Alpha (1----6) Dextran Increases its Affinity for Antigen," Journal of Experimental Medicine, 1988, vol. 168 (3), pp. 1099-1109.

Wells J.A., "Additivity of Mutational Effects in Proteins," Biochemistry, 1990, vol. 29 (37), pp. 8509-8517.

Wells J.A., et al., "Additivity of Mutational Effects in Proteins," Biochemistry, 1990, vol. 29 (37), pp. 8508-8517.

Wright A., et al., "Antibody Variable Region Glycosylation: Position Effects on Antigen Binding and Carbohydrate Structure," The EMBO Journal, 1991, vol. 10 (10), pp. 2717-2723.

Written Opinion for Application No. PCT/EP2009/001437, mailed on Jun. 18, 2009, 7 pages.

Wu H., et al., "Humanization of a Murine Monoclonal Antibody by Simultaneous Optimization of Framework and CDR Residues," Journal of Molecular Biology, 1999, vol. 294 (1), pp. 151-162.

Brinks H., et al., "The Repulsive Guidance Molecule RGMa is Involved in the Formation of Afferent Connections in the Dentate Gyrus," The Journal of Neuroscience, 2004, vol. 24 (15), pp. 3862-3869.

Casadevall A., et al., "Immunoglobulin Isotype Influences Affinity and Specificity," Proceedings of the National Academy of Sciences, 2012, vol. 109 (31), pp. 12272-12273.

Genbank Accession No. CAK97872.1, Jun. 30, 2006.

Genbank Accession No. NM008684, Feb. 28, 2005.

Genbank Accession No. NT039474, Aug. 31, 2004.

Genbank, "RGM Domain Family Member B [*Homo sapiens*]", Accession No. NP_001012779.2, Jul. 1, 2012.

Genbank, "Hemojuvelin Isoform a Precursor [*Homo sapiens*]", Accession No. NP_998818.1, Jun. 30, 2012.

Genbank, "*Homo sapiens* RGM Domain Family, Member A (RGMA), Transcript Variant 4, mRNA", Accession No. NM_0202112, Jun. 29, 2012.

Genbank, "Repulsive Guidance Molecule A Isoform 3 [*Homo sapiens*]", Accession No. NP_064596.2, Jun. 29, 2012.

Mirakaj et al., Supporting Information [online], Retrieved from the Internet:< URL: www.pnas.org/cgi/content/short/1015605108> (2011).

Uniprpot, Human Protein Encoded by Full Length cDNA Clone Seq Id No. 3867, EBI Accession No. ADL31834, May 20, 2004.

Uniport, Hemojuvelin Variant (R326X), EBI Accession No. ADU04761, Jan. 13, 2005.

Uniport, Novel Protein Sequence #944, EBI Accession No. ADQ65971, Oct. 7, 2004.

Yamashita T., RGMa Modulates T Cell Responses and is Involved in Autoimmune Encephalomyelitis, Supplementary Information Titles, Nature Medicine (2011).

Bowie J.U., et al., "Deciphering the Message in Protein Sequences: Tolerance to Amino Acid Substitutions," Science, 1990, vol. 247 (4948), pp. 1306-1310.

Burgess W.H., et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111 (5 Pt 1), pp. 2129-2138.

Frohman E.M., et al., "Modeling Axonal Degeneration within the Anterior Visual System: Implications for Demonstrating Neuroprotection in Multiple Sclerosis," Archives of neurology, 2008, vol. 65 (1), pp. 26-35.

Non-Final Office Action mailed Sep. 18, 2013 for U.S. Appl. No. 13/547,109, filed Jul. 12, 2012.

Non-Final Office Action mailed Aug. 21, 2013 for U.S. Appl. No. 12/963,461, filed Dec. 8, 2010.

Pawson T., et al., "Assembly of Cell Regulatory Systems through Protein Interaction Domains," Science, 2003, vol. 300 (5618), pp. 445-452.

Hamilton R.G., "Molecular Engineering: Applications to the Clinical Laboratory," Clinical Chemistry, 1993, vol. 39 (9), pp. 1988-1997.

Winter G., et al., "Humanized Antibodies," Immunology Today, 1993, vol. 14 (6), pp. 243-246.

Non-Final Office Action mailed Nov. 22, 2013 for U.S. Appl. No. 14/033,707, filed Sep. 23, 2013.

Final Office Action mailed Jan. 16, 2014 for U.S. Appl. No. 12/677,054, filed Jan. 25, 2013.

\* cited by examiner

RGM fractions induce growth cone collapse

Fraction 4

Fraction 5

Fraction 6

| Anterior - Control (C) | Anterior - PI-PLC (E) |
|---|---|
|  |  |
| Posterior - C | Posterior - E |
|  |  | iP 3 ⟶ 10

Fig.2b

RGM Peptide Sequences

| | |
|---|---|
| YLGTTLVVR | (SEQ ID NO: 1) |
| TFTDTFQ | (SEQ ID NO: 2) |
| MPEEVVNAVEDR | (SEQ ID NO: 3) |
| LTLLFK | (SEQ ID NO: 4) |
| TFTDTFQTCK | (SEQ ID NO: 5) |
| (GC)PLNQQLDFQTMR | (SEQ ID NO: 6) |
| AEMDE | (SEQ ID NO: 7) |
| PEAFTYE | (SEQ ID NO: 8) |
| HLEYR | (SEQ ID NO: 9) |
| QGLYL | (SEQ ID NO:10) |

A

B

USE OF RGM AND ITS MODULATORS

CROSS-REFERENCE TO RELATED APPLICATIONS

This is a continuation of U.S. patent application Ser. No. 12/939,823, filed on Nov. 4, 2010, which is a continuation of U.S. patent application Ser. No. 10/451,586, filed on Dec. 8, 2003, which is the U.S. national stage entry of International Patent Application No. PCT/EP2001/015289, filed on Dec. 21, 2001, which claims priority to European Patent Application No. 00128356.3, filed on Dec. 22, 2000, the contents of all of which are herein fully incorporated by reference.

SEQUENCE LISTING

A sequence listing in accordance with 37 C.F.R. §§1.821-1.825 is attached to the present invention and contained in a file named "8085USC2.txt" (28 Kb, created on Jun. 4, 2012) and is herein fully incorporated by reference.

The present invention relates to the use of a modulator of a polypeptide having or comprising an amino acid sequence as disclosed herein or of a functional fragment or derivative thereof or of a polynucleotide encoding said polypeptide or fragment or derivative for the preparation of a pharmaceutical composition for preventing, alleviating or treating diseases or conditions associated with the degeneration or injury of vertebrate nervous tissue, associated with angiogenic disorders or disorders of the cardio-vascular system. Furthermore, the invention provides for the use of a modulator of a polypeptide having or comprising said amino acid sequence or of a functional fragment or derivative thereof or of a polynucleotide encoding said polypeptide or fragment or derivative for the preparation of a pharmaceutical composition for preventing, alleviating or treating diseases or conditions associated with the degeneration or injury of vertebrate nervous tissue, associated with seizures, associated with angiogenic disorders or disorders of the cardio-vascular system. In addition the invention provides for the use of said polypeptide or said functional fragment or derivative thereof for the preparation of a pharmaceutical composition for preventing or treating tumor growth or formation of tumor metastases or as a marker of stem cells.

Several documents are cited throughout the text of this specification. The disclosure content of each of the documents cited herein (including any manufacturer's specifications, instructions, etc.) are hereby incorporated by reference.

The most important mechanism in formation of embryonic nervous systems is the guidance of axons and growth cones by directional guidance cues (Goodman, Annu. Rev. Neurosci. 19 (1996), 341-77; Mueller, Annu. Rev. Neurosci 22, (1999), 351-88). A suitable model system for studying this guidance process is the retinotectal system of vertebrates. In the chick embryo approximately 2 million retinal ganglion cell (RGC) axons leave each eye and grow towards the contralateral tectum opticum to form a precise map (Mey & Thanos, (1992); J. Himforschung 33, 673-702). Having arrived at the anterior pole of the optic tectum, RGC axons start to invade their tectal target to find their target neurons. Mapping occurs in such a way, that RGC axons from nasal retina project to posterior tectum and temporal axons to anterior tectum. Along the dorso-ventral axis, axons coming from dorsal retina terminate in ventral tectum, whereas those from ventral retina end up in dorsal tectum. In the end a precise topographic map is formed, where neighborhood relationships in the retina are preserved in the tectum, so that axons from neighboring ganglion cells in the retina synapse with neighboring tectal neurons. Most important for formation of this map, are graded tectal guidance cues, read by retinal growth cones carrying corresponding receptors which also show a graded distribution (Sperry, Proc. Natl. Acad. Sci. USA 50 (1963), 703-710; Bonhoeffer & Gierer, Trends Neurosci. 7 (1984) 378-381). Position of each retinal growth cone in the tectal field is therefore determined by two sets of gradients: receptor gradients on ingrowing retinal axons and growth cones and ligand gradients on tectal cells (Gierer, Development 101 (1987), 479-489). The existence of the graded tectal ligands has been postulated from anatomical work, their identification however proved to be extremely difficult and was only made possible with the development of simple in vitro systems (Walter; Development 101 (1987), 685-96; Cox, Neuron 4 (1990), 31-7). In the stripe assay RGC axons grow on a membrane carpet, consisting of alternating lanes of anterior (a) and posterior (p) tectal membranes. On these carpets, temporal retinal axons grow on anterior tectal membranes and are repelled by the posterior lanes, whereas nasal axons do not distinguish between a and p membranes (Walter, Development 101 (1987), 685-96). The same specificity is also observed in the growth cone collapse assay (Raper & Kapfhammer, Neuron 4 (1990), 21-29), where temporal retinal growth cones collapse after addition of posterior tectal membrane vesicles but do not react to anterior tectal vesicles and where nasal growth cones are insensitive to either type of vesicles (Cox, (1990), loc. cit.). In both assay systems, treatment of posterior tectal membranes with the enzyme phosphatidylinositol-specific phospholipase C (PI-PLC) which cleaves the lipid anchor of glycosylphosphatidylinositol (GPI)-linked proteins, removed their repellent and collapse-inducing activity (Walter, J. Physiol 84 (1990), 104-10).

One of the first repulsive guidance molecules identified in the retinotectal system of chick embryos was a GPI-anchored glycoprotein with a molecular weight of 33/35 kDa (Stahl, Neuron 5 (1990), 735-43). This 33/35 kDa molecule, later termed RGM (Repulsive Guidance Molecule), was active in both stripe and collapse-assays and was shown to be expressed in a low-anterior high-posterior gradient in the embryonic tecta of chick and rat (Mueller, Curr. Biol. 6 (1996), 1497-502; Mueller, Japan Scientific Societies Press (1997), 215-229). Due to the abnormal biochemical behaviour of RGM, the precise amino acid sequence was not obtainable. RGM was described as a molecule which is active during vertebrate development. Interestingly, RGM is down-regulated in the embryonic chick tectum after E12 and in the embryonic rat tectum after P2 and completely disappears after the embryonic stages (Müller (1992), Ph.D thesis University of Tubingen; Müller (1997) Japan Scientific Societies, 215-229) In 1996, Müller (loc. cit) have shown that CAL1 (chromophore-assisted laser inactivation) of RGM eliminates the repulsive guidance activity of posterior tectal membranes/RGM. However, due to the presence of other guidance molecules, in particular of RAGS (repulsive axon guidance signal) and ELF-1 (Eph ligand family 1), a complete elimination of guidance was not always detected and it was speculated that RGM acts in concert with RAGS (now termed ephrin-A5) and ELF-1 (ephrin-A2). It was furthermore envisaged that RGM may be a co-factor potentiating the activity of RAGS and ELF-1 in embryonic guidance events.

In 1980/81 the group of Aguayo found that, when peripheral neurons are transplanted/grafted into injured CNS of adult, axon growth of CNS neurons is induced (David, Science 214 (1981), 931-933). Therefore, it was speculated that CNS neurons have still the ability and capacity of neurite-outgrowth and/or regeneration, if a suitable environment would be provided. Furthermore, it was speculated that "CNS-neuron regeneration inhibitors" may exist. In 1988, Caroni and Schwab (Neuron 1, 85-96) described two inhibitors of 35 kDa and 250 kDa, isolated from rat CNS myelin (NI-35 and N1-250; see also Schnell, Nature 343 (1990) 269-272; Caroni, J. Cell Biol. 106 (1988), 1291-1288).

In 2000, the DNA encoding for N1-220/250 was deduced and the corresponding potent inhibitor of neurite growth was termed Nogo-A (Chen, Nature 403 (2000), 434-438. The membrane-bound Nogo turned out to be a member of the reticulon family (Grand Pré, Nature 403 (2000), 439-444).

Further factors which mediate neuronal outgrowth inhibition have first been isolated in grasshoppers, and termed "fasciclin IV" and later "collapsin" in chicken. These inhibitors belong to the so-called semaphorin family. Semaphorins have been reported in a wide range of species and described as transmembrane proteins (see, inter alia, Kolodkin Cell 75 (1993) 1389-99, Püschel, Neuron 14 (1995), 941-948). Yet, it was also shown that not all semaphorins have inhibitory activity. Some members of said family, e.g. semaphorin E, act as an attractive guidance signal for cortical axons (Bagnard, Development 125 (1998), 5043-5053).

A further system of repulsive guidance molecules is the ephrin-Eph system. Ephrins are ligands of the Eph receptor kinases and are implicated as positional labels that may guide the development of neural topographic maps (Flanagan, Ann. Rev. Neurosc. 21 (1998), 309-345). Ephrins are grouped in two classes, the A-ephrins which are linked to the membrane by a glycosylphosphatidylinositol-anchor (GPI-anchor) and the β-ephrins carrying a transmembrane domain (Eph nomenclature committee 1997). Two members of the A-ephrins, ephrin-A2 and ephrin-A5, expressed in low anterior-high posterior gradients in the optic tectum, have recently been shown to be involved in repulsive guidance of retinal ganglion cell axons in vitro and in vivo (see, inter alia (Drescher, Cell 82 (1995), 359-70; Cheng, Cell 79 (1994), 157-168; Feldheim, Neuron 21 (1998), 563-74; Feldheim, Neuron 25 (2000), 563-74)

Considering the fact that a plurality of physiological disorders or injuries are related to altered cellular migration processes, the technical problems underlying the present invention was to provide for means and methods for modifying altered developmental or cellular (migration) processes which lead to disease conditions. Accordingly, the present invention relates to the use of a modulator of a polypeptide having or comprising the amino acid sequence of SEQ ID NOs.18, 20, 23 or 25 or of a functional fragment or derivative thereof or of a polynucleotide encoding said polypeptide or fragment or derivative for the preparation of a pharmaceutical composition for preventing, alleviating or treating diseases or conditions associated with the degeneration or injury of vertebrate nervous tissue, associated with angiogenic disorders or disorders of the cardio-vascular system and associated with tumor formation and tumor growth.

In context of the present invention, and as documented in the appended examples, it was surprisingly found that the repulsive guidance molecule (RGM) is not only expressed during vertebrate development but is re-expressed in adult tissue, in particular in damaged adult tissues. It was, inter alia, surprisingly found that RGM is reexpressed after damage of the nervous tissue, after traumatic events or focal ischemias. The present invention provides for the complete nucleotide sequence and/or amino acid of RGM (see, e.g. SEQ 10 NO: 17 or 18 depicting the RGM sequence of chicken or SEQ 10 NO: 20 to 25 depicting the human RGM homologues.) RGM, as pointed out herein above, is a glycoprotein, linked to membranes by a GPI-anchor. Said GPI-anchor also carries a cross-reacting determinant (CRD) epitope and its carbohydrate part is able to bind peanut lectin. As documented herein, the RGM protein is a potent growth inhibitor and can assert neurite growth inhibition in picomolor concentrations.

The term "modulator" as employed herein relates to "inhibitors" as well as "activators" of RGM function. Most preferably said "modulation" is an inhibition, wherein said inhibition may be a partial or a complete inhibition.

The term "amino acid sequence of SEQ ID NO: 18, 20, 23 or 25 as employed herein relates to the amino acid sequence of RGM (repulsive guidance molecule) and relates to the RGM polypeptide of chicken or human, respectively. In particular, SEQ ID NOs: 20 and 21 depict human RGM1. Human RGM1 has been localized on chromosome 15. Further, human RGMs comprise RGM2 and RGM3. RGM2 is depicted in SEQ NO: 23 (amino acid sequence) and is encoded by a nucleotide sequence as shown in SEQ ID NO: 22. Human RGM2 has been localized on chromosome 5. Furthermore, human RGM3 is shown in appended SEQ ID NO: 25 (amino acid sequence) and encoded by a nucleotide sequence as depicted in SEQ ID NO: 24. Human RGM3 is located on chromosome 1. Yet, as will be discussed herein below, said term relates also to further RGM homologues.

The term "(poly)peptide" means, in accordance with the present invention, a peptide, a protein, or a (poly)peptide which encompasses amino acid chains of a given length, wherein the amino acid residues are linked by covalent peptide bonds. However, peptidomimetics of such RGM proteins/(poly)peptides wherein amino acid(s) and/or peptide bond(s) have been replaced by functional analogs are also encompassed by the invention.

The present invention is not restricted to RGM from human, mouse or chicken and its inhibitors but also relates to the use of inhibitors of RGM or of RGM itself (or functional fragments or derivatives thereof) from other species. Since the present invention provides for the use of amino acid sequences/polypeptides of RGM and its corresponding inhibitors and since the amino acid sequences of human and chicken RGM are disclosed herein, the person skilled in the art is provided with the information to obtain RGM sequences from other species, like, inter alia, mouse, rat, pig, etc. The relevant methods are known in the art and may be carried out by standard methods, employing, inter alia, degenerate and non-degenerate primers in PCR-techniques. Such molecular biology methods are well known in the art and, e.g., described in Sambrook (Molecular Cloning; A Laboratory Manual, 2nd Edition, Cold Spring Harbour Laboratory Press, Cold Spring Harbour, NY (1989)) and Ausubel, "Current Protocols in Molecular Biology", Green Publishing Associates; and Wiley Interscience, N.Y. (1989).

Furthermore, as employed in the context of the present invention, the term "RGM", "RGM modulator" and "RGM-inhibitor" also relates to RGM molecules (and their corresponding inhibitors) which are variants or homologs of the RGM molecules (and their inhibitors) as described herein. "Homology" in this context is understood to refer in this context to a sequence identity of RGMs of at least 70%, preferably more than 80% and still more preferably more than 90% on the amino acid level. The present invention, however, comprises also (poly)peptides deviating from wildtype amino acid sequences of human or chicken RGMs described herein, wherein said deviation may be, for example, the result of amino acid and/or nucleotide substitution(s), deletion(s), addition(s), insertion(s), duplication(s), inversion(s) and/or recombination(s) either alone or in combination. Those deviations may naturally occur or be produced via recombinant DNA techniques well known in the art The term "variation" as employed herein also comprises "allelic variants". These allelic variations may be naturally occurring allelic variants, splice variants as well as synthetically produced or genetically engineered variants.

The term "polynucleotide" in accordance with the present invention comprises coding and, wherever applicable, non-coding sequences (like promoters, enhancers etc.). It comprises DNA, RNA as well as PNA. In accordance with the present invention, the term "polynucleotide/nucleic acid molecule" comprises also any feasible derivative of a nucleic acid to which a nucleic acid probe may hybridize. Said nucleic acid probe itself may be a derivative of a nucleic acid molecule capable of hybridizing to said nucleic acid molecule or said derivative thereof. The term "nucleic acid molecule" further comprises peptide nucleic acids (PNAs) containing DNA analogs with amide backbone linkages (Nielsen, Science 254 (1991), 1497-1500). The term "nucleic acid molecule" which encodes a RGM (poly)peptide or a functional fragment/derivative thereof, in connection with the present invention, is defined either by (a) the specific nucleic acid sequences encoding said (poly)peptide specified in the present invention or (b) by nucleic acid sequences hybridizing under stringent conditions to the complementary strand of the nucleotide sequences of (a) and encoding a (poly)peptide deviating from the nucleic acid of (a) by one or more nucleotide substitutions, deletions, additions or inversions and wherein the nucleotide sequence shows at least 70%, more preferably at least 80% identity with the nucleotide sequence of said encoded RGM (paly)peptide having an amino acid sequence as defined herein above and functions as a RGM (or a functional fragment/derivative thereof).

The term "modulator" as employed herein also comprises the term "inhibitor", as mentioned herein above.

The term "inhibitor of a polypeptide having or comprising the amino acid sequence of SEQ ID NOs 18, 20, 23 or 25 or a functional fragment or derivative thereof", therefore, not only relates to the specific inhibitors of human or chicken RGM but also relates to inhibitors of RGM (or functional fragments or derivatives thereof) of other species. Useful inhibitors are disclosed herein as well as described herein below and in the appended examples.

The term "inhibitor" also comprises "modulators" of the RGM polypeptides and/or the RGM encoding nucleic acid molecule/gene. In context of this invention it is also envisaged that said "modulation" leads, when desired, to an activation of RGM.

The term "functional fragment or derivative thereof" in context of the present invention and in relation to the herein described RGM molecules comprises fragments of the RGM molecules defined herein having a length of at least 25, more preferably at least 50, more preferably at least 75, even more preferably at least 100 amino acids. Functional fragments of the herein identified RGM molecules or RGM molecules of other species (homologous RGMs) may be comprised in fusion and/or chimeric proteins. "Functional fragments" comprise RGM fragments (or its encoding nucleic acid molecules) which are able to replace RGM full length molecules in corresponding assays (as disclosed herein in the appended examples, e.g. collapse and/or stripe assays) or may elucidate an anti-RGM specific immune-response and/or lead to specific anti-RGM antibodies. An example of such a "functional fragment" is, inter alia, the functional fragment of chicken RGM depicted in SEQ ID NO: 19. In context of the present invention, polynucleotides encoding functional fragments of RGM and/or its derivatives have preferably at least 15, more preferably at least 30, more preferably at least 90, more preferably of at least 150, more preferably of at least 300 nucleotides. The term "derivative" means in context of their invention derivatives of RGM molecules and/or their encoding nucleic acid molecules and refer to natural derivatives (like allelic variants) as well as recombinantly produced derivatives/variants which may differ from the herein described RGM molecules by at least one modification/mutation, e.g. at least one deletion, substitution, addition, inversion or duplication. The term "derivative" also comprises chemical modifications. The term "derivative" as employed herein in context of the RGM molecule also comprises soluble RGM molecules which do not comprise any membrane anchorage.

As mentioned herein above, the present invention provides for the use of a modulator, preferably an inhibitor, of RGM molecules and/or their corresponding encoding polynucleotides/nucleic acid molecules for the preparation of a pharmaceutical composition for preventing, alleviating or treating various disorders of the nervous system, angiogenic disorders or disorders of the cardio-vascular system and malignancies of different etiology.

In a preferred embodiment, said disorders of the nervous system comprise degeneration or injury of vertebrate nervous tissue, in particular neurodegenerative diseases, nerve fiber injuries and disorders related to nerve fiber losses.

Said neurodegenerative diseases may be selected from the group consisting of motoneuronal diseases (MND), amyotrophic lateral sclerosis (ALS), Alzheimers disease, Parkinsons disease, progressive bulbar palsy, progressive muscular atrophy, HIV-related dementia and spinal muscular atrophy (ies), Down's Syndrome, Huntington's Disease, Creutzfeldt-Jacob Disease, Gerstmann-Straeussler Syndrome, kuru, Scrapie, transmissible mink encephalopathy, other unknown plion diseases, multiple system atrophy, Riley-Day familial dysautonomia said nerve fiber injuries may be selected from the group consisting of spinal cord injury(ies), brain injuries related to raised intracranial pressure, trauma, secondary damage due to increased intracranial pressure, infection, infarction, exposure to toxic agents, malignancy and paraneoplastic syndromes and wherein said disorders related to nerve fiber losses may be selected from the group consisting of paresis of nervus facialis, nervus medianus, nervus ulnaris, nervus axillaris, nervus thoracicus longus, nervus radialis and for of other peripheral nerves, and other acquired and non-acquired diseases of the (human) central and peripheral nervous system.

The above mentioned spinal cord and brain injuries not only comprise traumatic injuries but also relate to injuries caused by stroke, ischemia and the like. It is in particular envisaged that the inhibitors as defined herein below and comprising, inter alia, anti-RGM antibodies be employed in the medical art to stimulate nerve fiber growth in individuals, in particular in vertebrates, most preferably in humans.

In a more preferred embodiment of the present invention, the invention provides for the use of a modulator, preferably an inhibitor to RGM (or a functional fragment or derivative thereof) for the preparation of a pharmaceutical composition for the treatment of disorders of the cardio-vascular system, wherein these disorders, e.g., comprise disorders of the blood-brain barrier, brain oedema, secondary brain damages due to increased intracranial pressure, infection, infarction, ischemia, hypoxia, hypoglycemia, exposure to toxic agents, malignancy, paraneoplastic syndromes.

It is envisaged, without being bound by theory, that RGM inhibitors may stimulate surviving neurons to project collateral fibers into the diseased tissue, e.g. the ischemic tissue.

As illustrated in the appended examples, RGM is expressed locally at the side of artificial transection of brain/spinal cord tissue in test animals (like rats), e.g., in the penumbra region surrounding an ischemic core of a human suffering focal ischemia in the temporal context. Furthermore, it is documented in the appended examples that RGM is, surprisingly, expressed in tissue(s) having experienced from traumatic brain injuries. The invention also relates to the use of a RGM polypeptide or a functional fragment or derivative thereof or the use of a polynucleotide encoding the same (polypeptides and polynucleotides as defined herein), wherein the above described disease or condition associated with seizures is epilepsy. An epilepsy is thereby characterized by an epileptic seizure as a convulsion or transient abnormal event experienced by the subject, e.g. a human patient, due to a paroxysmal discharge of (cerebral) neurons. The epileptic seizures comprise tonic seizures, tonic-clonic seizures (grand mal), myoclonic seizures, absence seizures as well as akinetic seizures. Yet, also comprised are in context of this invention simple partial seizures, e.g. Jacksonian seizures and seizures due to perinatal trauma and/or fetal anoxia. As mentioned herein below, the uses described herein relate in particular to the preparation of pharmaceutical compositions for the treatment of diseases/conditions associated with aberrant sprouting of nerve fibres, like epilepsy, see also Routbort, Neuroscience 94 (1999), 755-765.

In a even more preferred embodiment of the invention, the modulator, preferably the inhibitor of RGM (or of its functional fragment or derivative thereof or of its encoding nucleid acid molecule) is used for the preparation of a pharmaceutical composition for the modification of neovascularization. Said modification may comprise activation as well as stimulation. It is in particular envisaged that said neovascularisation be stimulated and/or activated in diseased tissue, like inter alia, ischemic and/or infarctious tissue. Furthermore, it is envisaged that the RGM-inhibitors described herein may be employed in the regulation of the blood-brain barrier permeability.

It is furthermore envisaged that said modulators, preferably said inhibitors for RGM be employed in the alleviation, prevention and/or inhibition of progression of vascular plaque formation (e.g. arterosclerosis) in cardio-vascular, cerebo-vascular and/or nephrovascular diseases/disorders.

Furthermore, the present invention provides for the use of a modulator, preferably an inhibitor of RGM as defined herein for the preparation of a pharmaceutical composition for remyelination. Therefore, the present invention provides for a pharmaceutical composition for the treatment of demyelinating diseases of the CNS, like multiple sclerosis or of demyelinating diseases like peripheral neuropathy caused by diphtheria toxin, Landry-Guillain-Barré-Syndrom, Elsberg-Syndrom, Charcot-Marie-Tooth disease and other polyneuropatias. A particular preferred inhibitor of RGM in this context is an antibody directed against RGM, e.g. an IgM antibody. It has previously been shown that certain IgMs bind to oligodendrocytes and thereby induce remyelination. IgM antibodies against RGM are known in the art and comprise e.g. the F3D4 described in the appended examples.

In addition the invention provides for the use of a RGM polypeptide as defined herein or of a functional fragment or derivative thereof or of a polynucleotide encoding said polypeptide or fragment or derivative for the preparation of a pharmaceutical composition for preventing, alleviating or treating diseases or conditions associated with the activity of autoreactive immune cells or with overactive inflammatory cells. Most preferably these cells are T-cells.

Furthermore, the present invention relates to the use of a modulator, preferably an inhibitor or another RGM binding molecule of a RGM polypeptide or of a functional fragment or derivative thereof or of a polynucleotide encoding said polypeptide or of fragment/derivative thereof for modifying and/or altering the differentiation status of neuronal stem cells and/or their progenitors. Said stem cells are normally found in the subventricular zones of many brain regions. It is known that factors in the microenvironment of the brain dramatically influence the differentiation of undifferentiated stem cells. It is assumed that due to the characteristic expression of RGM in the subventricular layers of many different brain regions, this molecule could be a marker for stem cells. Furthermore, RGM inhibitors, like antibodies could be useful markers for stem cells. Most important in stem cell biology is the understanding of factors influencing their differentiation. It is therefore assumed that RGM inhibitors change the developmental fate of these cells.

As documented in the appended examples, RGM is not only expressed in ischemic tissue but is also expressed in scar tissue surrounding (brain) lesions.

It is particularly preferred that the modulator, preferably the inhibitor of the RGM molecule (or its functional fragment or derivative) is an antibody or a fragment or a derivative thereof, is an aptamer, is a specific receptor molecule capable of interacting with a RGM polypeptide or with a functional fragment or derivative thereof, or is a specific nucleic acid molecule interacting with a polynucleotide encoding an RGM and/or the polypeptide as defined herein.

The antibody to be used in context of the present invention can be, for example, polyclonal or monoclonal antibodies. Techniques for the production of antibodies are well known in the art and described, e.g. in Harlow and Lane "Antibodies, A Laboratory Manual", CSH Press, Cold Spring Harbor, 1988. The production of specific anti-RGM antibodies is further known in the art (see, e.g. Müller (1996) loc. cit.) or described in the appended examples.

The term "antibody" as employed herein also comprises chimeric, single chain and humanized antibodies, as well as antibody fragments, like, inter alia, Fab fragments. Antibody fragments or derivatives further comprise $F(ab')_2$. Fv or scFv fragments; see, for example, Harlow and Lane, loc. cit. Various procedures are known in the art and may be used for the production of such antibodies and/or fragments, see also appended examples. Thus, the (antibody) derivatives can be produced by peptidomimetics. Further, techniques described for the production of single chain antibodies (see, inter alia, U.S. Pat. No. 4,946,778) can be adapted to produce single chain antibodies to polypeptide(s) of this invention. Also, transgenic animals may be used to express humanized antibodies to polypeptides of this invention. Most preferably, the antibody to be used in the invention is a monoclonal antibody, for example the F3D4 antibody described in the appended examples may be employed when an IgM is desired. The general methodology for producing, monoclonal antibodies is well-known and has been described in, for example, Köhler and Milstein, Nature 256 (1975), 494-496 and reviewed in J. G. R. Hurrel, ed., "Monoclonal Hybridoma Antibodies Techniques and Applications", CRC Press Inc., Boca Raron, Fla. (1982), as well as that taught by L. T. Mimms et al., Virology 176 (1990), 604-619.

Preferably, said antibodies (or inhibitors) are directed against functional fragments of the RGM polypeptide. As pointed out herein above and as documented in the appended examples, such functional fragments are easily deducible for the person skilled in the art and, correspondingly, relevant antibodies (or other inhibitors) may be produced.

The "modulator", preferably the "inhibitor" as defined herein may also be an aptamer. In the context of the present invention, the term "aptamer" comprises nucleic acids such as RNA, ssDNA (ss=single stranded), modified RNA, modified ssDNA or PNAs which bind a plurality of target sequences having a high specificity and affinity. Aptamers are well known in the art and, inter alia, described in Famulok, Cum Op. Chem. Biol. 2 (1998), 320-327. The preparation of aptamers is well known in the art and may involve, inter alia, the use of combinatorial RNA libraries to identify binding sites (Gold, Ann. Rev. Biochem. 64 (1995), 763-797). Said other receptors may, for example, be derived from said antibody etc. by peptidomimetics.

Other specific "receptor" molecules which may function as inhibitors of the RGM polypeptides are also comprised in this invention. Said specific receptors may be deduced by methods known in the art and comprise binding assays and/or interaction assays. These may, inter alia, involve assays in the ELISA-format or FRET-format. Said "inhibitor" may also comprise specific peptides binding to and/or interfering with RGM.

Furthermore, the above recited "modulator", preferably "inhibitor" may function at the level of RGM gene expression. Therefore, the inhibitor may be a (specific) nucleic acid molecule interacting with a polynucleotide encoding a RGM molecule (or a functional fragment or derivative thereof.) These inhibitors may, e.g., comprise antisense nucleic acid molecules or ribozymes.

The nucleic acid molecule encoding RGM (and as disclosed herein, e.g., SEQ ID NO: 17) may be employed to construct appropriate anti-sense oligonucleotides. Said antisense oligonucleotides are able to inhibit the function of wild-type (or mutant) RGM genes and comprise, preferably, at least 15 nucleotides, more preferably at least 20 nucleotides, even more preferably 30 nucleotides and most preferably at least 40 nucleotides.

In addition, ribozyme approaches are also envisaged for use in this invention. Ribozymes may specifically cleave the nucleic acid molecule encoding RGMs.

In the context of the present invention ribozymes comprise, inter alia, hammerhead ribozymes, hammerhead ribozymes with altered core sequences or deoxyribozymes (see, e.g., Santoro, Proc. Natl. Acad. Sci. USA 94 (1997), 4262) and may comprise natural and in vitro selected and/or synthesized ribozymes. Nucleic acid molecules according to the present invention which are complementary to nucleic acid molecules coding for proteins/(poly)peptides regulating, causing or contributing to obesity and/or encoding a mammalian (poly)peptide involved in the regulation of body weight (see herein below) may be used for the construction of appropriate ribozymes (see, e.g., EP-B1 0 291 533, EP-A10 321 201, EP-A2 0 360 257) which specifically cleave nucleic acid molecules of the invention. Selection of the appropriate target sites and corresponding ribozymes can be done as described for example in Steinecke, Ribozymes, Methods in Cell Biology 50, Galbraith, eds. Academic Press, Inc. (1995), 449-460.

Said "inhibitor" may also comprise double-stranded RNAs, which lead to RNA-mediated gene interference (see Sharp, Genes and Dev. 13 (1999), 139-141).

Further potential inhibitors of RGM may be found and/or deduced by interaction assay and employing corresponding read-out systems. These are known in the art and comprise, inter alia, two hybrid screenings (as, described, inter alia, in EP-0 963 376, WO 98/25947, WO 00/02911) GST-pull-down columns, co-precipitation assays from cell extracts as described, inter alia, in Kasus-Jacobi, Oncogene 19 (2000), 2052-2059, "interaction-trap" systems (as described, inter alia, in U.S. Pat. No. 6,004,746) expression cloning (e.g. lambda gill), phage display (as described, inter alia, in U.S. Pat. No. 5,541,109), in vitro binding assays and the like. Further interaction assay methods and corresponding read out systems are, inter alia, described in U.S. Pat. No. 5,525,490, WO 99/51741, WO 00/17221, WO 00/14271 or WO 00/05410.

A further objective of the present invention is to provide for the use of a RGM polypeptide and/or of polypeptide having or comprising the amino acid sequence of SEQ ID NOs. 18, 20, 23 or 25 or of a functional fragment or derivative thereof or of a polynucleotide encoding said polypeptide or fragment or derivative for the preparation of a pharmaceutical composition for preventing, alleviating or treating diseases or conditions associated with excessive collateral sprouting of nerve fibres.

The present invention, therefore, provides for the medical use of RGM protein(s) and/or functional fragments/derivatives thereof or for the use of polynucleotides encoding said RGM protein(s) in conditions where excessive collateral sprouting occurs. Said conditions comprise, but are not limited to, epilepsy, phantom pain and neuropathic pain. For example, McNamara (Nat. Suppl. 399 (1999), A15-A22) has described that said sprouting occurs in certain types of epilepsy. The RGM molecule, either naturally isolated or recombinantly produced, or its functional fragments/derivatives may therefore be employed as potent "stop" signals for growing nerve fibres. The feasibility of such an approach has been shown by Tanelian (Nat. Med. 3 (1997), 1398-1401) who employed a semaphorin for inhibition of nerve fiber growth.

In yet another embodiment, the present invention provides for the use of RGM and/or of a polypeptide having or comprising the amino acid sequence of SEQ ID NOs 18, 20, 23 or 25 or of a functional fragment or derivative thereof or of a polynucleotide encoding said polypeptide or fragment or derivative for the preparation of a pharmaceutical composition for preventing or treating tumor growth or formation of tumor metastases.

RGM (naturally isolated or recombinantly produced) and/or functional fragments thereof may be employed for the preparation of a pharmaceutical composition for the treatment of neoplastic disorders, in particular of disorders related to tumor (cell) migration, metastasis and/or tumor invasion. Furthermore, it Is envisaged that RGM inhibits undesired neovascularisation. Said neovascularisation, as an angiogenic disorder during neoplastic events, should be prevented in order to limit, inter alia, tumor growth.

Growth cones of neurons and (invasive) tumor cells secrets a cocktail of proteases (uPA, tPA, MNPs, etc.) in order to degrade extracellular matrix. Furthermore, similar mechanisms for adhesion and (cell) migration are employed by these cellular systems. RGM and/or its functional fragments may be employed to actively stimulate withdrawal of lamellipodia of tumor cells and/or to induce their collapse. As demonstrated in the appended examples RGM also influences tumor growth behaviour, i.e. is capable of negatively influencing tumor growth.

In addition the invention provides for the use of a RGM polypeptide as defined herein or of a functional fragment or derivative thereof or of a polynucleotide encoding said polypeptide or fragment or derivative for the preparation of a pharmaceutical composition for preventing, alleviating or treating diseases or conditions associated with the activity of autoreactive immune cells or with overactive inflammatory cells. Most preferably these cells are T-cells.

In yet another embodiment, the invention provides for the use of a RGM polypeptide having or comprising, inter alia, the amino acid sequence of SEQ ID NOs.18, 20, 23 or 25 or of a functional fragment or derivative thereof or of a polynucleotide encoding said polypeptide or fragment or derivative for the preparation of a pharmaceutical composition for the treatment of inflammation processes and/or allergies, for wound healing or for the suppression/alleviation of scar formation. Scar tissue is formed by invading cells, most importantly by fibroblasts and/or glial cells. Migration and adhesion of these cells are required to get to the lesion side. RGM or an active fragment/derivative could prevent accumulation of these cells in the lesion side, thereby preventing or slowing down scar formation. In inflammatory reactions cells migrate to the inflamed region and RGM or its active fragment/derivative prevent or reduce migration of these cells to the side of inflammation, thereby preventing overactive inflammatory reactions.

In context of the present invention, the term "pharmaceutical composition" also comprises optionally further comprising an acceptable carrier and/or diluent and/or excipient. The pharmaceutical composition of the present invention may be particularly useful in preventing and/or treating pathological disorders in vertebrates, like humans. Said pathological disorders comprise, but are not limited to, neurological, neurodegenerative and/or neoplastic disorders as well as disorders associated with seizures, e.g. epilepsy. These disorders comprise, inter alia, Alzheimer's disease, Parkinson's disease, amyotrophic lateral sclerosis (FALS/SALS), ischemia, stroke, epilepsy, AIDS dementia and cancer. The pharmaceutical composition may also be used for prophylactic purposes. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. However, it is also envisaged that the pharmaceutical compositions are directly applied to the nervous tissue. The dosage regimen will be determined by the attending physician and clinical factors. As is well known in the medical arts, dosages for any one patient depends upon many factors, including the patient's size, body surface area, general health, age, sex, the particular compound to be administered, time and route of administration, and other drugs being administered concurrently. Pharmaceutically active matter may be present preferably, inter alia, in amounts between 1 ng and 1000 mg per dose, more preferably in amounts of 1 ng to 100 mg however, doses below or above this exemplary range are envisioned, especially considering the aforementioned factors. If the regimen is a continuous infusion, it should also be in the range of 1 ng to 10 mg units per kilogram of body weight per minute, respectively. Progress can be monitored by periodic assessment. The compositions of the invention may be administered locally or systemically. Administration will generally be parenterally, e.g., intravenously. The compositions of the invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents, depending on the intended use of the pharmaceutical composition. Such agents may be drugs acting on the central nervous system as well as on small, unmyelinated sensory nerve terminals (like in the skin), neurons of the peripheral nervous system of the digestive tract, etc.

It is also understood that the pharmaceutical composition as defined herein may comprise nucleic acid molecules encoding RGMs (and/or functional fragments or derivatives thereof) or corresponding RGM inhibitors or defined herein: As mentioned herein-above, said inhibitors comprise, but are not limited to, antibodies, aptamer, RGM-interacting peptides as well as inhibitors interacting with the RGM-encoding polynucleotides.

Accordingly, the present invention also provides for a method of treating, preventing and/or alleviating pathological disorders and conditions as defined herein, whereby said method comprises administering to a subject in need of such a treatment a pharmaceutical composition/medicament as defined herein. Preferably, said subject is a human.

The nucleic acid molecules may be particularly useful in gene therapy approaches and may comprise DNA, RNA as well as PNA. Said nucleic acid molecules may be comprised in suitable vectors, either inter alia, gene expression vectors. Such a vector may be, e.g., a plasmid, cosmid, virus, bacteriophage or another vector used e.g. conventionally in genetic engineering, and may comprise further genes such as marker genes which allow for the selection of said vector in a suitable host cell and under suitable conditions. Furthermore, the vectors may, in addition to the nucleic acid sequences encoding RGM or its corresponding inhibitors, comprise expression control elements, allowing proper expression of the coding regions in suitable host cells or tissues. Such control elements are known to the artisan and may include a promoter, translation initiation codon, translation and insertion site for introducing an insert into the vector. Preferably, the nucleic acid molecule of the invention is operatively linked to said expression control sequences allowing expression in (eukaryotic) cells. Particularly preferred are in this context control sequences which allow for correct expression in neuronal cells and/or cells derived from nervous tissue.

Control elements ensuring expression in eukaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymidine kinase promoter, SV40, RSV-promoter (Rous sarcoma virus), human elongation factor 1α-promoter, CMV enhancer, CaM-kinase promoter or SV40-enhancer. For the expression for example in nervous tissue and/or cells derived therefrom, several regulatory sequences are well known in the art, like the minimal promoter sequence of human neurofilament L (Charron, J. Biol. Chem 270 (1995), 25739-25745). Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (in-Vitrogene, as used, inter alia in the appended examples), pSPORT1 (GIBCO BRL) or pGEMHE (Promega), Beside the nucleic acid molecules defined herein, the vector may further comprise nucleic acid sequences encoding for secretion signals. Such sequences are well known to the person skilled in the art. Furthermore, depending on the expression system used leader sequences capable of directing the protein/(poly)peptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a part thereof.

As mentioned herein above, said vector may also be, besides an expression vector, a gene transfer and/or gene targeting vector. Gene therapy, which is based on introducing therapeutic genes into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957, Schaper, Current Opinion in Biotechnology 7 (1996), 635-640 Verma, Nature 389 (1997), 239-242 WO 94/29469, WO 97/00957, U.S. Pat. Nos. 5,580,859, 589,66 or 4,394,448 and references cited therein.

In particular, said vectors and/or gene delivery systems are also described in gene therapy approaches in neurological tissue/cells (see, inter alia Blöimer, J. Virology 71 (1997) 6641-6649) or in the hypothalamus (see, inter alia, Geddes, Front Neuroendocrinol. 20 (1999), 296-316 or Geddes, Nat. Med. 3 (1997), 1402-1404). Further suitable gene therapy constructs for use in neurological cells/tissues are known in the art, for example in Meier (1999), J. Neuropathol. Exp. Neural. 58, 1099-1110. The nucleic acid molecules and vectors of the invention may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules described herein.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

In yet another embodiment, the present invention provides for the use of a (RGM) polypeptide and/or a polypeptide having or comprising the amino acid sequence of SEQ ID NOs 18, 20, 23 or 25 or of a functional fragment or derivative thereof or of a polynucleotide encoding said polypeptide or fragment or derivative as a marker of stem cells. Since it is envisaged that stem cells as well as their undifferentiated progenitor cells express RGM, RGM and/or functional fragments or derivatives thereof may be employed to influence the differentiation/differentiation pattern of said stem cells.

It is furthermore envisaged that antibodies directed against RGMs, in particular directed against polypeptides disclosed herein or comprising the amino acid sequence of SEQ ID NOs 18, 20, 23 or 25 (or (a) functional fragment(s)/derivative(s) thereof) may be employed to influence the differentiation of (neuronal) stem cells and (neuronal) progenitor cells. It is particularly preferred that said antibodies (as well as other RGM-inhibitors and/or RGM-binding molecules) be employed to selectively label stem cells. Therefore these reagents may be employed as markers for stem cells. It is also envisaged that peptides or derivatives be employed in said purpose.

In a particularly preferred embodiment of the present invention, the polypeptide and/or fragment thereof which comprises or has an amino acid sequence as depicted in SEQ ID NOs 18, 20, 23 or 25 and/or is a RGM molecule to be used in accordance with their invention is a soluble, i.e. not membrane bound molecule.

As shown in Davis (1994), Science 266, 816-819 ephrins, in particular A-ephrins, are not active in soluble, monomeric form. In contrast, soluble RGMs are active and may function without any membrane-attachment. RGM, in contrast to ephrins, is capable of self-formation of dimers and/or of the formation of higher aggregates. The invention also provides for the use of a RGM molecule and/or a polypeptide having or comprising the amino acid sequence of SEQ ID NOs 18, 20, 23 or 25 or of a functional fragment or derivative thereof or of a polynucleotide encoding said polypeptide or a fragment or a derivative for the preparation of a pharmaceutical composition for alleviating, preventing and/or treating homeostatic and/or bleeding disorders and/or vascular damage.

It is envisaged, without being bound by theory, that RGMs may, due to their structural homology to von-Willebrand factor (vWF), be employed in the treatment of said disorders/diseases. Furthermore, it is envisaged that RGM may interact with vonWillebrand factor and that said molecule, thereby, influences the activity of vWF.

Furthermore, the inhibitors as defined herein should be employed in disorders where immune cells invade the brain, like multiple sclerosis, encephalomyelitis disseminata.

The present invention also provides for the use of an antibody or a fragment or a derivative thereof, or an aptamer, or a binding molecule capable of interacting with a polypeptide having or comprising the amino acid sequence of SEQ ID NOs 18, 20, 23 or 25 or with functional fragment or derivative thereof or of an nucleid acid molecule capable of interacting with a polynucleotide encoding said polypeptide or a fragment thereof for the preparation of a diagnostic composition for detecting neurological and/or neurodegenerative disorders or dispositions thereto.

The diagnostic composition may be used, inter alia, for methods for determining the expression of the nucleic acids encoding RGM polypeptides by detecting, inter alia, the presence of the corresponding mRNA which comprises isolation of RNA from a cell, contacting the RNA so obtained with a nucleic acid probe as described above under hybridizing conditions, and detecting the presence of mRNAs hybridized to the probe. Furthermore, corresponding mutations and/or alterations may be detected. Furthermore, RGM (poly)peptides can be detected with methods known in the art, which comprise, inter alia, immunological methods, like, ELISA or Western blotting.

The diagnostic composition of the invention may be useful, inter alia, in detecting the prevalence, the onset or the progress of a disease related to the aberrant expression of a RGM polypeptide. Accordingly, the diagnostic composition of the invention may be used, inter alia, for assessing the prevalence, the onset and/or the disease status of neurological, neurodegenerative and/or inflammatory disorders, as defined herein above. It is also contemplated that anti-RGM antibodies, aptamers etc. and compositions comprising such antibodies, aptamers, etc. may be useful in discriminating (the) stage(s) of a disease.

The diagnostic composition optionally comprises suitable means for detection. The nucleic acid molecule(s), vector(s), antibody(ies), (poly)peptide(s), described above are, for example, suitable for use in immunoassays in which they can be utilized in liquid phase or bound to a solid phase carrier. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

Solid phase carriers are known to those in the art and may comprise polystyrene beads, latex beads, magnetic beads, colloid metal particles, glass and/or silicon chips and surfaces, nitrocellulose strips, membranes, sheets, duracytes and the walls of wells of a reaction tray, plastic tubes or other test tubes. Suitable methods of immobilizing nucleic acid molecule(s), vector(s), host(s), antibody(ies), (poly)peptide(s), fusion protein(s) etc. on solid phases include but are not limited to ionic, hydrophobic, covalent interactions and the like. Examples of immunoassays which can utilize said compounds of the invention are competitive and non-competitive immunoassays in either a direct or Indirect format. Commonly used detection assays can comprise radioisotopic or non-radioisotopic methods. Examples of such immunoassays are the radioimmunoassay (RIA), the sandwich (immunometric assay) and the Northern or Southern blot assay. Furthermore, these detection methods comprise, inter alia, IRMA (Immune Radioimmunometric Assay), EIA (Enzyme Immuno Assay), ELISA (Enzyme Linked Immune Assay), FIA (Fluorescent Immune Assay), and CLIA (Chemiluminescent Immune Assay). Furthermore, the diagnostic compounds of the present invention may be are employed in techniques like FRET (Fluorescence Resonance Energy Transfer) assays.

The nucleic acid sequences encoding RGMs of other species as well as variants of RGMs are easily deducible from the information provided herein. These nucleic acid sequences are particularly useful, as pointed out herein above, in medical and/or diagnostic setting, but they also provide for important research tools. These tools may be employed, inter alia, for the generation of transgenic animals which overexpress or suppress RGMs or wherein the RGM gene is silenced and/or deleted. Furthermore, said sequences may be employed to detect and/or ellucidate RGM interaction partners and/or molecules binding to and/or interfering with RGMs.

The Figures show:

FIG. 1: RGM protein fractions Induce collapse of RGC growth cones.

Solubilized membrane proteins from E9/E10 chick brains were loaded on two different ion exchange columns, a DEAE anion exchange column and a cation exchange column. RGM was eluted from the cation exchange column at a Na CI concentration of 200-400 mM in two 1 ml fractions (4+5) was incorporated into lecithin vesicles and lecithin vesicles were used in collapse experiments with RGC growth cones. RGM-containing fractions (4+5, arrows), but not RGM-free fractions induced extensive collapse (>90%) of RGC growth cones. Neither ephrin-A5 nor ephrin-A2 could be detected with specific antibodies, in RGM-fractions. RGC axons and growth cones on laminin were stained with AlexaPhalloidin. Western blots from two dimensional gels were incubated with the F3D4 monoclonal antibody, and were subsequently stained by a whole protein, india ink stain.

FIG. 2: Comparative two dimensional gel analysis of tectal proteins and RGM sequences.

A: Membranes from E9/10 anterior and posterior chick tecta were enriched and treated with buffer (C) or with PI-PLC (E), to remove GPI-anchored proteins. The putative RGM (arrow in Anterior-E+Posterior-E), a PI-PLC cleavable basic protein with a molecular weight of 33 kDa, was cut out and was used for nanoelectrospray tandem mass spectrometry. Two dimensional gels were stained with silver. No anterior-posterior difference of the RGM candidate is observed in these gels, this is probably due to the presence of two other proteins in the selected spot.

B: Deduced RGM peptide sequences

Figure 3:
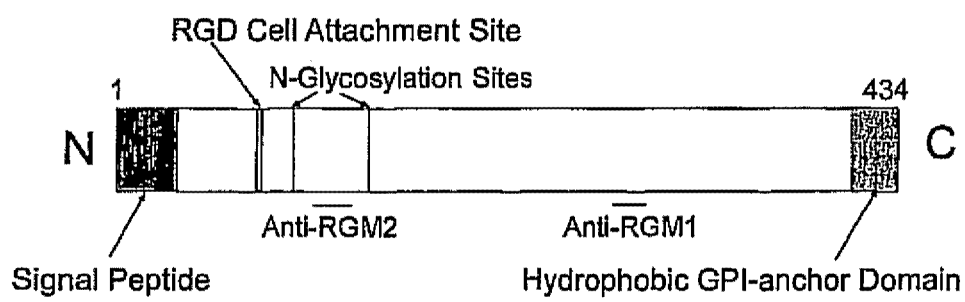

FIG. 3: shows a schematic view of the RGM protein. Hydrophobic domains are present at the N- and C-termini of the protein. Epitopes of the two polyclonal anti-RGM antibodies are demarcated.

Figure 4:
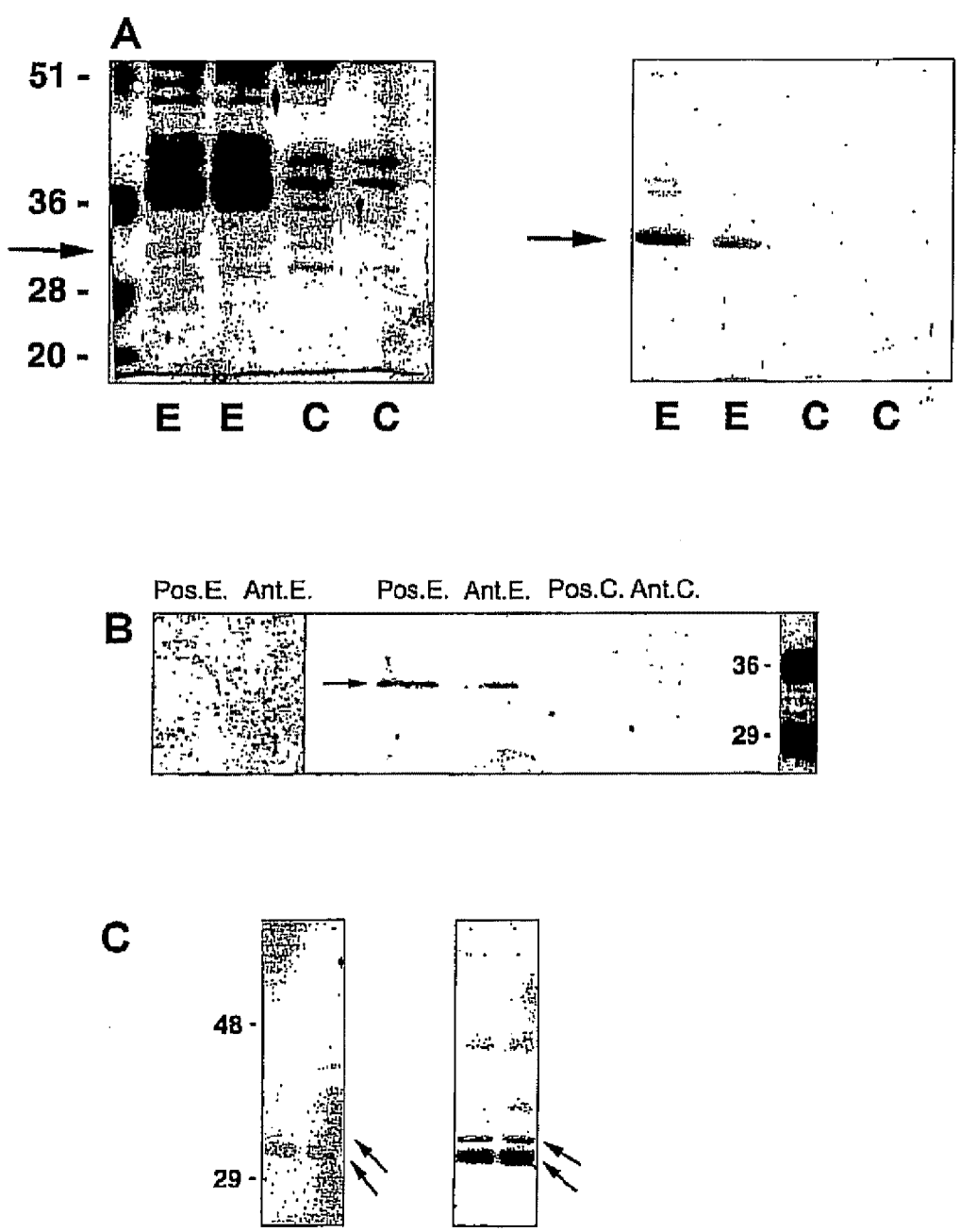

FIG. 4: The polyclonal and the monoclonal RGM antibody recognize the same 33 kDa protein.

A. The anti-RGM1 antibody binds to a GPI-anchored CRD- (cross reacting determinant) positive 33 kDa protein. Left blot: An anti-CRD antibody binds to a low abundant, 33 kDa protein (arrow), present in the E (PI-PLC supernatant) but not the C fraction (control supernatant). Right blot: AntiRGM1 staining of a GPI-anchored 33 kDa protein on a western blot with supernatant from E9/E10 chick brain membranes.

B. The GPI-anchored 33 kDa antigen of the anti-RGM1 antibody is more abundant in posterior (pos.) than in anterior (ant.) tectal membranes. Left blot: rabbit preimmune serum did not bind to any protein on western blots with PI-PLC supernatant protein from anterior and posterior tectum. Right blot: Anti-RGM1 binding to a 33 kDa protein. E=PI-PLC supernatant from tectal membranes, C=control supernatants from tectal membranes.

C. Anti-RGM1 and F3D4 recognize the same antigens in tectal membranes. Left blot: F3D4 staining of tectal membrane proteins. A double band at 33 kDa (lower arrow) and a hardly visible band at 35 kDa (upper arrow) are recognized.

Right blot: Anti-RGM1 staining reveals the same staining pattern with 33 and 35 kDa antigens (arrows). Contrary to the membrane fraction, where 3 different protein bands are observed, only one band is detected in most western blots with PI-PLC supernatants.

For detection on western blots, a secondary, alkaline phosphatase-conjugated antibody was used and NBT (nitro blue tetrazolium) and BCIP (bromochloroindolyl phosphat) was used for the colour reaction.

Figure 5:
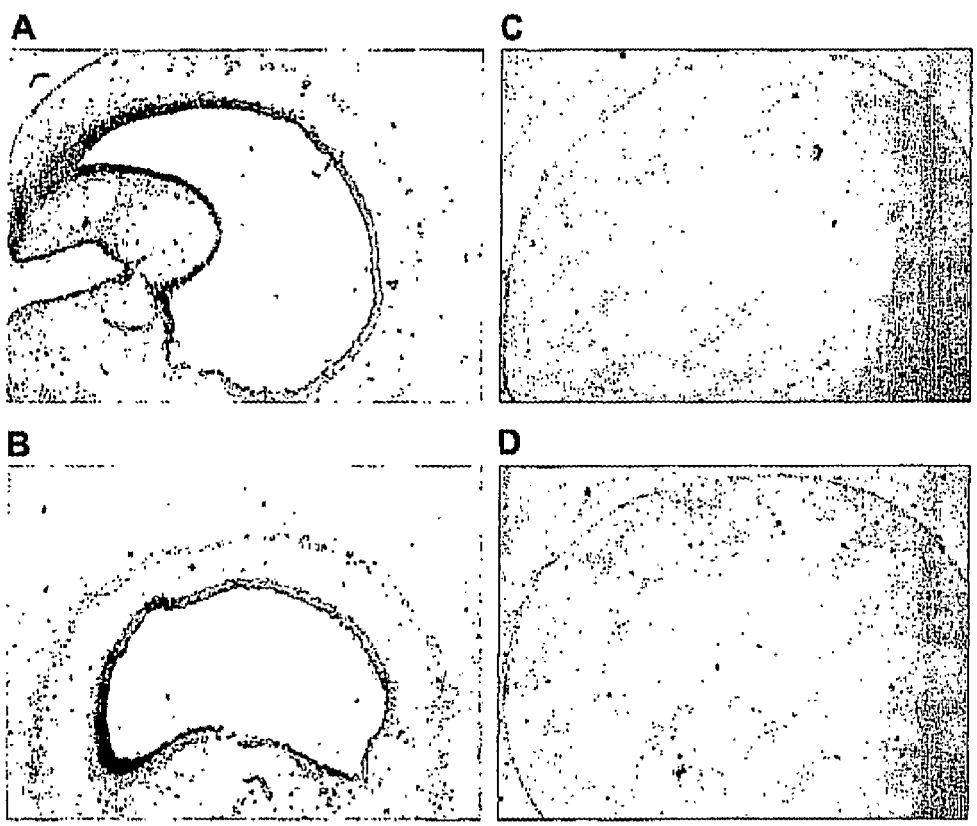

FIG. 5: The RGM anti-sense probe hybridizes to an mRNA with graded expression along the anterior-posterior axis.

A, B: RGM-mRNA is expressed in a periventricular gradient in the tectum of an E9 chick embryo. In a more superficial layer (arrows), RGM is also expressed but at much lower level. The anterior tectal pole is to the right, the posterior to the left.

C, D: No staining is detected with the RGM sense probe, on parallel cryostat sections from E9 chick tecta. The anterior tectal pole is to the right, the posterior to the left.

Figure 6:
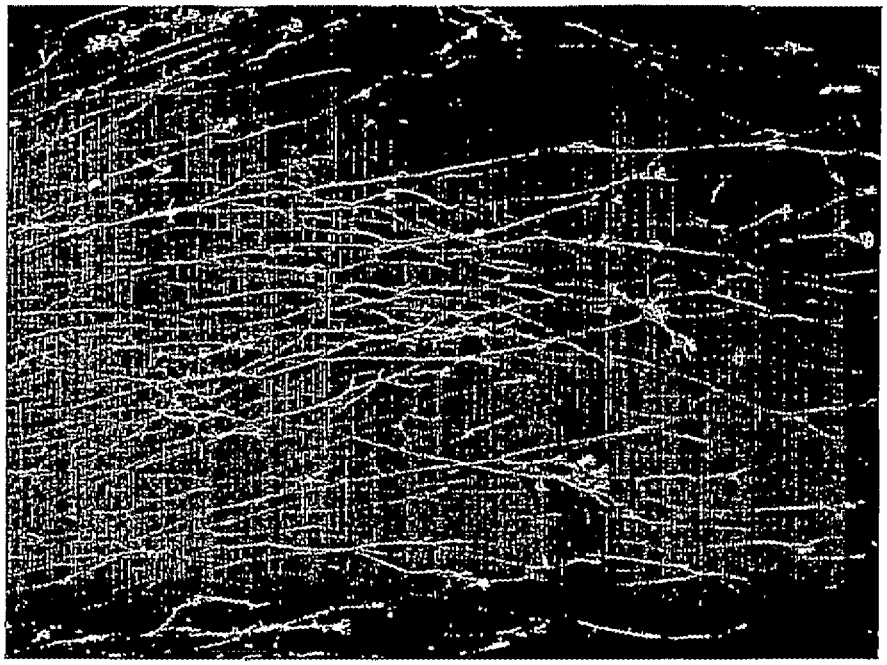
Figure 6:
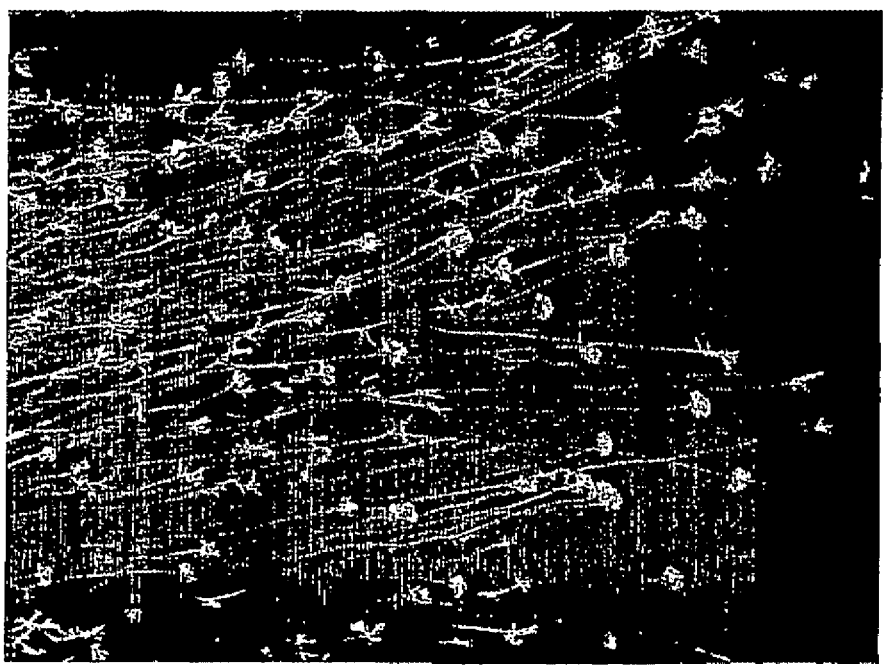

FIG. 6: Recombinant RGM Induces collapse of retinal growth cones.

A: RGC axons were grown on laminin-coated coverslips and affinity purified recombinant RGM was added at a final concentration of 10 ng/ml. More than 90% of temporal retinal growth cones are collapsed.

B: Neighboring, RGM-free fractions from affinity purification did not induce collapse of temporal growth cones. Supernatants from cos-7 cells transfected with an empty plasmid, did not possess any collapse-inducing activity (data not shown).

In A and B, retinal axons and growth cones were stained with the F-actin stain Alexa-Phalloidin.

Figure 7:
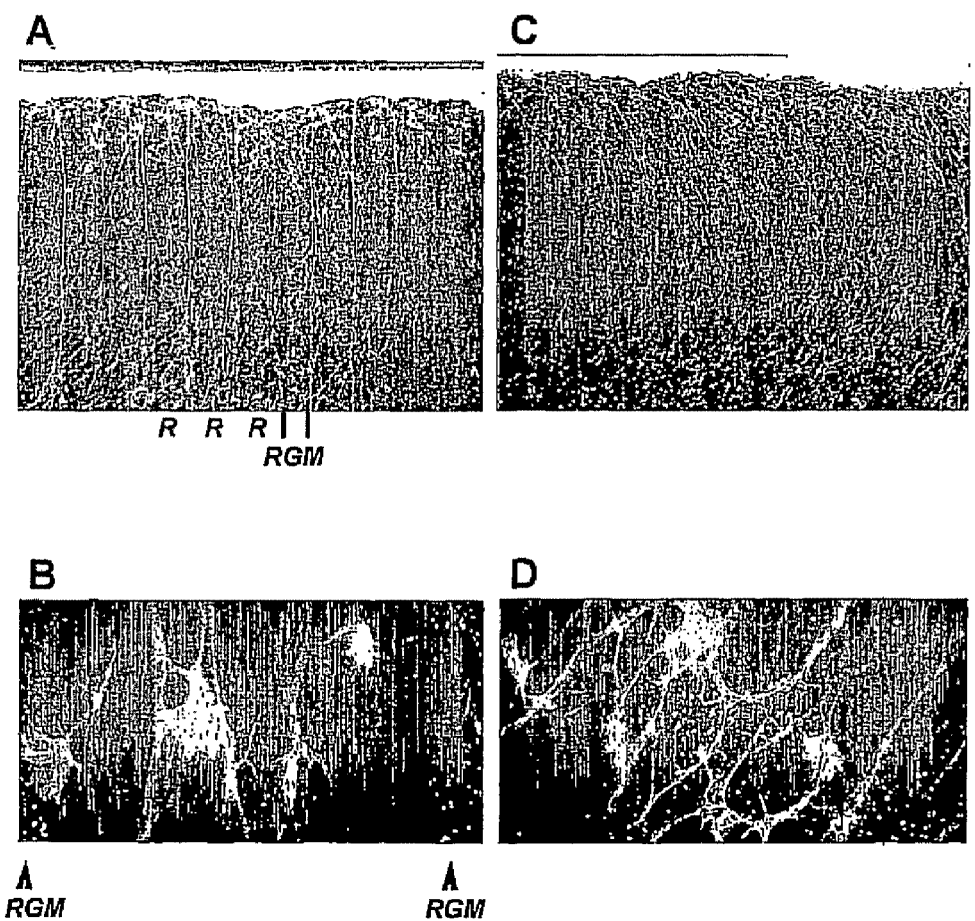

FIG. 7: Recombinant RGM guides temporal retinal axons in the stripe assay.

A, B: Temporal retinal axons avoid the RGM-containing stripes (demarcated with red fluorescent beads). Membranes from RGM-transfected cos-7 cells (marked with beads) and anterior tectal membranes were used to prepare striped carpets.

C, D: Temporal retinal axons do not show any avoidance reaction, when membranes from cos-7 cells, transfected with an empty plasmid (red beads) were used.

In A-D, striped membrane carpets were in addition coated with laminin to enhance retinal axon growth in accordance with a previous protocol (Monschau et al. 1997).

Figure 8:
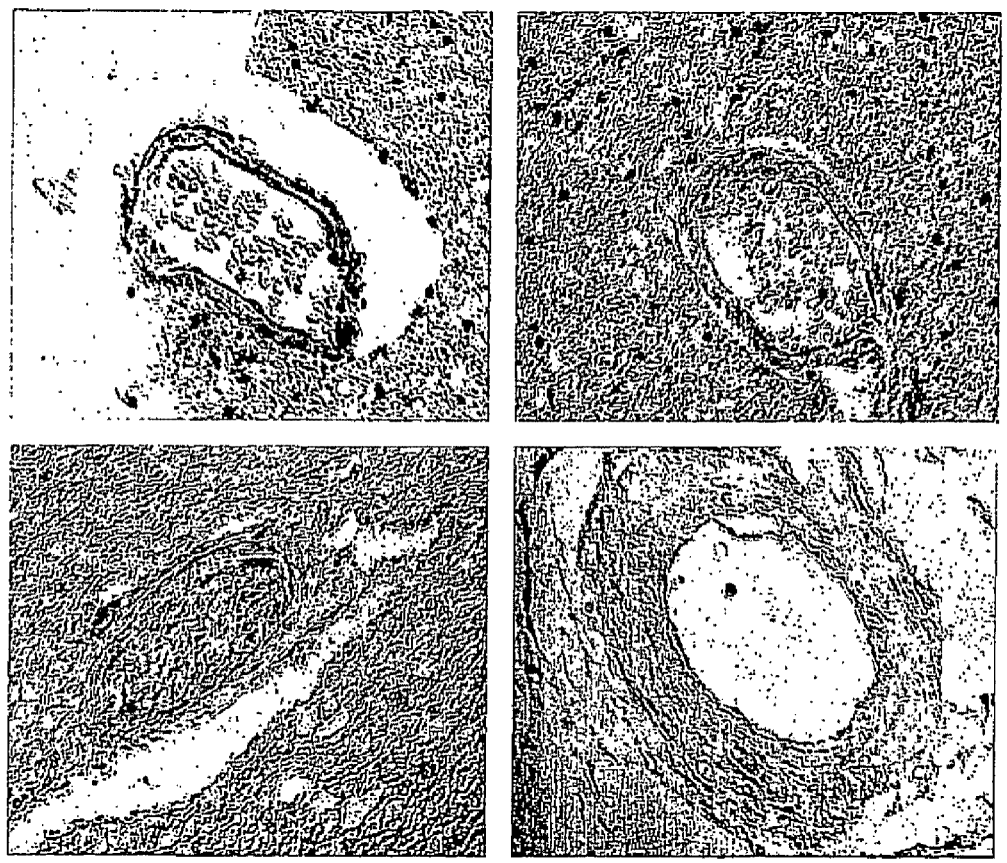

FIG. 8: RGM staining in endothel of (human) brain.

RGM immunoreactivity was detected in endothelial and vascular smooth muscle cells (SMC), both, in healthy, neuropathological unaltered control brains and injured brains, suggesting a constitutive, physiological role in vascular homeostasis.

Figure 9:
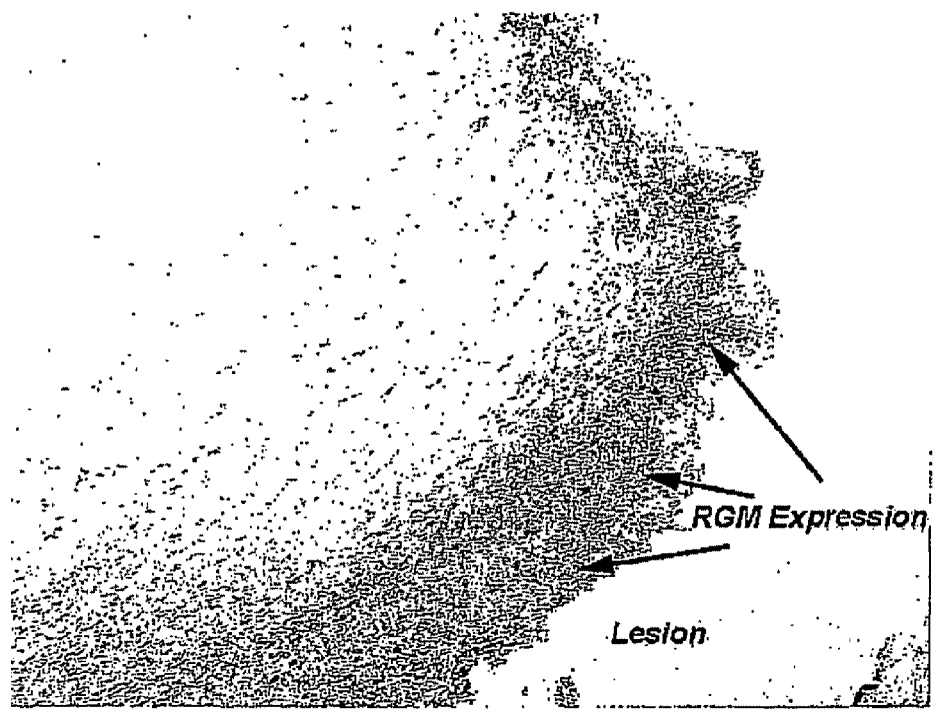

FIG. 9: RGM expression in a lesion of a human being deceased due to severe brain injury (1-2 hours after his death). RGM expression on infiltrating cells from the immune system. Upregulation of cellular RGM expression correlated with the time course and appearance of infiltrating leukocytes and activation of microglia/macrophages after injury (Stoll et al., 1998). Early after injury (up to 2.5 days), RGM immunoreactivity was found on leukocytes of granulocytic, monocytic and lymphocytic origin in vessels within ischemic tissue. Paralleled by edema formation, up to 1-7 days, RGM-positive cells were found extravasating outside the vascular walls into the focal ischemic lesioned parenchyma. In perivascular regions, RGM-positive cells formed clusters in the Virchow-Robin spaces from day 1-7, which subsided later. These peri-vascular cells, also referred to as adventitial or perithelial cells are characteristically alert immune cells (Kato and Walz, 2000; Streit et al., 1999).

Figure 10:
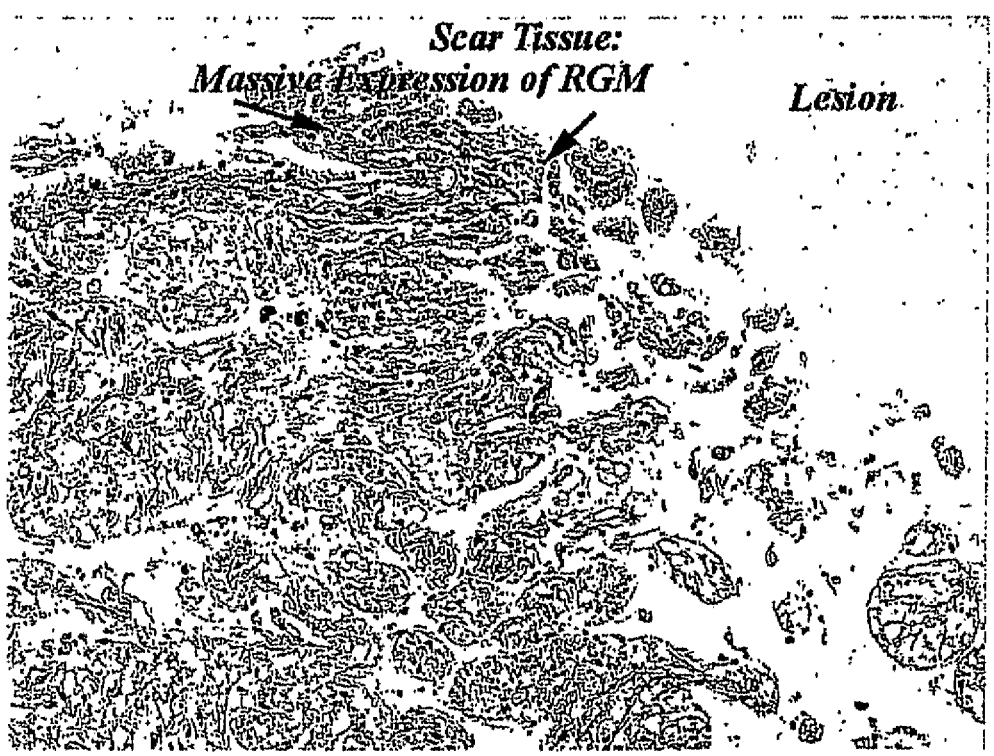

FIG. 10: RGM expression in a brain lesion (human).

With increasing time after brain injury, most remarkable changes corresponded to areas of ongoing scar formation. In these areas, well defined extracellular RGM-positive laminae and RGM-positive fibroblastoid and reactive astrocytic cells were visible condensing adjacent to the border zone. These RGM-positive laminae increased in magnitude and regional extend over time.

The Examples illustrate the invention.

EXAMPLE 1

Microsequencing of an RGM Candidate

To separate RGM from the A-ephrins, a combination of two different ionexchange columns was employed. RGM, in contrast to the A-ephrins, bound to a strong cation exchanger and was eluted at a salt concentration of 200-400 mM NaCl. After incorporation of RGM into lecithin vesicles, strong collapse-inducing activity was observed in RGM-fractions (fractions 4+5, FIG. 1) but not in neighboring RGM-free fractions (fraction 6, FIG. 1). Neither ephrin-A5 nor ephrin-A2 was present in these fractions, proving thereby that RGM function does not require presence of the A-ephrins.

To get peptide sequences from RGM, microsequencing of all proteins, (cleaved from the membrane by treatment with the enzyme PI-PLC and having a molecular weight of 30-35 kDa and an isoelectric point between 7 and 9 was carried out). To this aim, anterior and posterior membranes from embryonic chick tecta (E9/10) were prepared with some modifications as described previously (Walter, Development 101, (1987), 685-96) and membrane pellets were subject to treatment with enzyme PI-PLC (E fraction) or buffer alone (C fraction). In particular, Membranes from embryonic chick tecta (E9/10) were prepared with some modifications as described previously (Walter et at., 1987). All steps were performed at 4° C. Tecta from 100 chick embryos were isolated and were divided into three parts equal in length along the anterior-posterior axis. The middle tectal parts were discarded and the anterior and posterior parts were worked up separately. Membranes were washed with PBS containing protease inhibitors and were centrifuged. Tectal membrane pellets were resuspended in triethanolamine buffer and were treated with the enzyme PI-PLC (50 mU Boehringer Mannheim/Roche Diagnostics GmbH), to remove glycosylphosphatidylinositol anchored (GPI-anchored) proteins from the membranes. No PI-PLC was added to the other anterior and posterior tectal membrane fractions, the control-fractions (C). Enzyme (E) and control (C) fractions were incubated at 37° C. for 1.5 hours and membrane suspensions were centrifuged at 400.000×g in a Beckmann TLA 100.3 rotor. Supernatants were collected and their protein concentrations were determined (Bradford 1976, modified by Zor and Selinger, 1996). Supernatants were precipitated with ice cold 10% trichloroacetic acid, were centrifuged and protein pellets were washed in ethanol-ether (1:1 v/v) and solubilized in sample buffer (8.5 M urea, 5% B-mercaptoethanol, 2.5% ampholytes pH 3-10, 2% NP 40).

E fractions and C fractions were loaded onto two dimensional gels, and after silver staining candidate proteins in the E-fractions (FIG. 2A, arrows) were cut out and subject to in gel tryptic digestion and nanoelectrospray ionization (Wilm, Nature 379 (1996), 466-9).

In detail, said 20 gelelectrophoresis and the protein sequence analysis was carried out as outlined herein below:

Tectal proteins resuspended in sample buffer, were separated using two dimensional gel electrophoresis. 20:g of tectal protein was loaded on each gel. Non-equilibrium pH gradient electrophoresis (NEPHGE) followed by SDS-PAGE in the second dimension was performed as described by Boxberg (1988). After the SDS PAGE, gels were stained by a modified silver staining protocol from Heukeshoven and Demick (Heukeshoven & Demick, Electrophoresis 9, (1988), 372-375).

Silver-stained proteins in the 2D gels, with a basic isoelectric point and a molecular weight of 33/35 kDa, present in the PI-PLC treated E fraction but not in the C fraction, were cut out using a sharp and sterile scalpel.

Microsequencing was done using the technique of nanoelectrospray tandem mass spectrometry as previously described (Wilm et al., 1996). The protein spots were digested in gel by trypsin and the resulting peptides were adsorbed and stepwise eluted into the electrospray source for mass spectral analysis. Nanoelectrospray was performed on an API III (Perkin-Elmer) mass spectrometer as described by Wilm and Mann (Wilm & Mann, Anal. Chem. 68 (1996), 1-8). After selecting an ionized peptide from the peptide mixture, the peptide was fragmented and the peptide fragments were analysed.

Mass spectrometric microsequencing of ionized peptides from the spot marked by arrows in FIG. 2, yielded ten different peptides, with lengths of 5-14 amino acids as shown in FIG. 2B; (SEQ ID NOs 1-10). The selected spot, was present in anterior and posterior PI-PLC supernatants at similar levels. RGM is however more abundant in posterior than in anterior tectal membranes and the disappearance of the ap-difference in the 2D-gels was most likely caused by two different proteins unrelated to RGM and present in the selected spot.

EXAMPLE II

Cloning of the RGM Gene

Three out of the ten peptide sequences (SEQ ID NOs 1 to 10) obtained by nanoelectrospray tandem mass spectrometry were used for synthesis of degenerate oligonucleotide primers and PCR experiments were performed as follows: Three out of the ten peptide sequences obtained by nanoelectrospray tandem mass spectrometry were used for synthesis of degenerate oligonucleotide primers and their complementary sequences.

P1F:
(SEQ ID NO: 11)
5'-ATGCC(AGCT)GA(AG)GA(AG)GT(AGCT)GT(AGCT)-3'

P1R:
(SEQ ID NO: 12)
5'-TT(AGCT)AC(AGCT)AC(CT)TC(CT)TC(AGCT)GGCAT-3'

P2F:
(SEQ ID NO: 13)
5'-GA(CT)AC(AGCT)TT(CT)CA(AG)AC(AGCT)TG(CT)M-3'

P2R:
(SEQ ID NO: 14)
5'-TT(AG)CA(AGCT)GT(CT)TG(AG)M(AGCT)GT(AG)TC-3'

P3F:
(SEQ ID NO: 15)
5'-AA(CT)CA(AG)CA(AG)(CT)T(AGCT)GA(CT)TT(CT)CA-3'

P3R:
(SEQ ID NO: 16)
5'-TG(AG)AA(AG)TC(AGCT)A(AG)(CT)TG(CT)TG(AG)TT-3'

Moloney murine leukemia virus reverse transcriptase and random hexamer primers were used to synthesize single-stranded cDNA from E9 chick tectum total RNA. Combinations of forward (F) and reverse (R) primers were added to the cDNA and PCR amplification was done using Taq polymerase. The following PCR conditions were used: an initial denaturation step at 95° C. for 5 min followed by 30 cycles of 95° C. for 40 s, 50° C. for 1 min, 72° C. for 2 min. The PCR products were cloned into the pGEM T vector (Promega) and four positive clones were sequenced using the ALF express sequencer (Pharmacia). The sequence yielded an ORF, containing most of the peptide sequences obtained by microsequencing. The 459 bp fragment was used for screening a cDNA library to obtain the full length sequence and for further analysis such as Northern blotting and in situ hybridization.

The PCR products were loaded onto agarose gels stained with ethidium bromide and a PCR product of 459 bp in length, was obtained and cloned Into the pGEM T vector. After sequencing, most of the peptide sequences were found in the PCR product, confirming that the correct candidate was amplified. The 459 bp fragment was used for screening an E14 chicken brain cDNA library. Positive clones contained an insert of approximately 4 kb and sequencing confirmed the presence of the 459 bp fragment and additional downstream sequences, including a stop codon. Upstream sequences were obtained by performing 5'-RACE.

In detail, the 459 bp probe was used to screen 500.000 plaques of an E14 chicken brain library, cloned in the λ Zap vector. After two screening rounds, eight single plaques were isolated and the related inserts were cloned into the Bluescript vector using the rapid excision kit (Stratagene). The positive clones, analysed by restriction digestions, contained an insert of approximately 4 kb and sequencing confirmed the presence of the 459 bp fragment and additional downstream sequences, including a stop codon. To get the sequence of the region upstream of the 459 bp fragment, a 5'-RACE was performed according to the manufacturer's protocol using the RACE kit from Boehringer Mannhelm and total RNA from E9 chick tecta. A 700 bp band was amplified, purified, cloned into pGEM T vector, and 5 positive clones were sequenced. The sequence had an ORF with two methionines which could act as potential start sites. The full length sequence of RGM was confirmed independently several times.

For in situ and Northern blot experiments, the 459 bp fragment was cloned into the Bluescript KS vector (Stratagene) and anti-sense and sense probes were produced by using the SP6 and T7 polymerases, respectively.

This 5'-RACE yielded an ORF with two methionines, potential start sites. The complete ORF of RGM is 1302 nucleotides in length and encodes a protein consisting of 434 amino acids (FIG. 3A; SEQ ID NO:17). Two hydrophobic domains are present at the N-terminus and C-terminus, respectively (FIG. 3B; SEQ ID NO:18), and two different algorithms suggested that the N-terminal hydrophobic domain encodes a signal peptide (best cleavage site predicted: at aa 29), the C-terminal domain, a GPI-anchor domain (best cleavage site predicted: at aa 406). RGM has no significant homology to any other protein, present in the databases and does not carry any specific domain or motif, except an tri-amino acid motif, the RGD site, a potential cell attachment site (Ruoshlahti, Annu. Rev. Cell Dev. Biol. 12 (1996), 697-715). Preliminary results suggest that this site is dispensable for RGM function. Polyclonal antibodies, named anti-RGM1 (against aas: 276-293) and anti-RGM2 (against aas: 110-130), raised against two peptides of the recombinant RGM molecule, recognize a GPI-anchored 33 kDa molecule, which is present at higher levels in posterior than in anterior tectal membrane PI-PLC supernatants (FIG. 4A). In membrane fractions at least three protein bands appear, a double band at 33 kDa and a single band at 35 kDa. These protein bands are recognized by the polyclonal anti-RGM1 antibody and the monoclonal F3D4 antibody (Müller (1996), loc. cit) (FIG. 4B). Both antibodies show identical staining patterns on western blots and immunoprecipitation experiments with anti-RGM1 resulted in pull down of a GPI-anchored, F3D4-positive protein. These results prove, that the antigens of the F3D4 monoclonal antibody and of the anti-RGM1 polyclonal antibody are identical.

RGM is the first member of a new class of axon guidance molecules, sharing no sequence homology with ephrins, netrins, slits, semaphorins and any other axon guidance molecules.

The corresponding human RGM sequence (SEQ ID NO:20) could be deduced by screening the human genome database with the deduced chicken RGM sequence.

EXAMPLE III

RGM mRNA is Expressed in a Gradient in the Optic Tectum

To analyse expression of RGM-mRNA in the tectum opticum, an RGM anti-sense probe was used in in situ hybridization experiments on cryostat sections from E9 chick tecta. Strongest staining is observed in the periventricular layer, surrounding the tectal ventricle and staining intensity is much stronger in posterior tectum than in anterior tectum (FIG. 5A, B). Cell bodies of radial glial cells are located in the periventricular layer and the staining pattern confirms previous data using the monoclonal F3D4 antibody, where staining of glial endfeet and of glial cell bodies was observed (Mueller; (1996), loc. cit.; Mueller, (1997), loc. cit.). In a more superficial layer, a much weaker staining is detected with the RGM anti-sense probe but a differential expression between anterior and posterior tectal poles is hard to detect in this layer. In this layer tectal neurons are RGM-positive. This is in line with the expression of RGM by a subpopulation of tectal neurons. Overall, the staining pattern with the RGM anti-sense probe looks very similar to the expression pattern of ephrin-A5 with both messages being found in a periventricular and in a more superficial tectal layer. No staining is detectable with the RGM-sense probe.

On northern blots with tectal RNA, the RGM anti-sense probe marked two transcripts at 5.5 and 6.1 kb. Both messages are down-regulated at E14 with the smaller message being no longer detectable and the larger transcript being clearly present, albeit at lower levels.

RGM is active in in vitro assays and shows a graded expression in the tectum opticum of vertebrates. Based on Southern blot data it is assumed that there are least two additional family members which might have similar guidance activity. (see FIG. 11)

EXAMPLE IV

Recombinant RGM is Active in Collapse and Stripe Assay

To analyse the function of recombinant RGM, the full length RGM cDNA was used to transfect cos-7 cells with a lipofection procedure. The full length RGM cDNA was cloned into the Kpn1 site of the expression vector pTriEx-1 (Novagen). Cos-7 cells were transfected with the pTriEx-1 plasmid containing RGM cDNA or with the empty plasmid using the Superfect transfection reagent (Qiagen) according to the manufacturer's protocol. The DNA-Superfect mixture was added to Cos-7 cells growing in 10 cm dishes. 2 hours later medium was removed, cells were washed with PBS and grown for an additional 48 hours in fresh medium. Conditioned medium was collected, run over an RGM-affinity column and RGM-containing fractions and RGM free control fractions were directly used in collapse assay experiments. For stripe assay experiments, RGM-transfected Cos-7 cells and empty plasmid transfected cells were washed with PBS and harvested using a rubber policeman in the presence of homogenization buffer containing protease inhibitors. Conditioned medium of cos-7 cells transfected with the RGM-pTriEx-1 plasmid was collected and run over an antiRGM1 antibody column. Eluted fractions were evaluated with a sensitive and rapid dot blot assay and RGM-positive fractions were added to retinal axons growing on a laminin substratum. At a final concentration of 10 ng/ml, soluble RGM induced collapse of 90% of temporal RGC growth cones (FIG. 6A). Neighboring, RGM-free fractions or conditioned and concentrated supernatants from cos-7 cells transfected with the empty plasmid did not possess any collapse-inducing activity (FIG. 6B). Recombinant RGM is active in soluble form, is a strong difference between RGM and the A-ephrins and suggests a role for a chemotropic mechanism, in establishing the retinotectal map.

For preparation of striped membrane carpets, membranes from RGM- or mock transfected cells were used. Carpets consisting of alternate lanes of membranes from mock-transfected cos-7 cells and from RGM-transfected cells were offered to temporal and nasal RGC axons. To enhance the poor outgrowth-stimulating activity of cos-7 membranes, anterior tectal membranes or laminin were added. Collapse assay and stripe assays were prepared and employed as follows: The collapse assay was performed as described (Cox, (1990), loc. cit.; Wahl, J. Cell Biol. 149(2) (2000), 263-70). 5:I of the RGM-positive fraction from the RGM-cos supernatant or supernatant from control cos cells or RGM-free fractions, was added to the retinal cultures. One hour later cultures were fixed by carefully adding 1 ml of fixative (4% paraformaldehyde, 0.33 M sucrose, pH 7.4). 4-12 hours later, cultures were washed and stained by Alexa-Phalloidin (Molecular Probes), following the recommendations of the manufacturer. Stained cultures were stored on a computer using a CCD camera and the images were analysed with the SIS analysis imaging software.

Stripe assay experiments were performed as previously described by Walter et al. (1987). Membrane carpets consisted of lanes of anterior tectal membranes mixed with membranes from RGM-transfected cos cells (ratio: 1:1), alternating with lanes consisting of anterior membranes mixed with membranes from empty plasmid transfected cos cells (ratio 1:1). In an alternative protocol, membrane carpets consisting of alternating lanes of membranes from RGM-transfected cos cells and of control cos membranes, were incubated for 2 hours at 37° C. with 20 1:g/ml laminin (Becton-Dickinson). Before use, the carpets were washed with Hank's buffer (2×).

On these carpets, temporal RGC axons, but not nasal axons, showed a clear repulsive avoidance behaviour, growing on the RGM-free membrane stripes (FIG. 7 A-D). These results demonstrate, that the recombinant RGM protein is not only active in collapse but also in stripe assays.

RGM shares with the A-ephrins A2 and A5 the GPI-anchor, the graded expression and functional activity in two different in vitro systems. Its activity is however different from the two A-ephrins in other respects. The specificity of its activity is not restricted to temporal axons and growth cones. Nasal axons and growth cones also react, albeit at higher RGM concentrations. This is in line with the previous observations, that temporal retinal axons react more strongly to RGM than nasal retinal axons (Stahl, (1990), loc. cit). For ephrin-A5, a slight difference in sensitivity of temporal and nasal retinal axons has been observed, this difference is however not as pronounced as with RGM (Drescher, Cell 82 (1995), 359-70). Besides the stronger concentration dependancy of RGM function, another crucial difference is that RGM, in contrast to both ephrin-A5 and ephrin-A2, seems to be active in soluble form and apparently does not require aggregation to stimulate its currently unknown retinal receptor. These in vitro results underscore the difference between ephrins and RGM. In the stripe assay, inactivation of RGM using the F3D4 monoclonal antibody and the chromophore-assisted laser inactivation (CAL1) method, resulted in complete neutralization of repulsive guidance activities of posterior tectal membranes in more than 50% of the experiments (Mueller, (1996), loc. cit.) F3D4 however neither binds ephrin-A2 nor ephrin-A5 (Mueller, (1997), loc. cit.) and it was therefore suggested that the A-ephrins and RGM somehow interact in special membrane domains to which they are recruited by their GPI-anchors. Such a colocalization could explain the result, that inactivation of RGM lead in addition to inactivation of ephrin-A2 and ephrin-A5 and could explain the complete neutralization observed in the stripe assay experiments (Mueller, (1996), loc. cit.). The functional relationship of RGM with ephrin-A2 and ephrin-A5 and the in vivo role of RGM need to be addressed, especially since both ephrins have been shown to be important molecular determinants for topographic map formation in vertebrates (Nakamoto, Cell 86 (1996), 755-66; Frisen, Neuron 20 (1998), 235-43; Feldheim, Neuron 21 (1998), 563-74; Picker, Development 126 (1999), 2967-78; Feldheim, Neuron 25 (2000), 563-74; Brown, Cell 102 (2000), 77-88). There are however evidences from two vertebrates, which suggest that others factors, besides the ephrins, are required for formation of the retinotectal map. Deletion of either the ephrin-A2 or the ephrin-A5 gene in mice, resulted in mapping phenotypes with some retinal axons forming ectopic termination zones in the superior colliculus (SC), the mammalian homologue of the optic tectum, and with nasal retinal axons overshooting the SC and terminating in the inferior colliculus. In ephrin-A2$^{-/-}$ mice, temporal axons showed mapping errors with ectopic termination zones, but nasal axons did not show any mapping errors in contrast to the ephrin-A5$^{-/-}$ mice which had defects in topographic mapping of nasal but not temporal axons (Frisen, (1998), loc. cit.; Feldheim, (2000), loc. cit.). Deletion of both genes should therefore result in a much more disturbed mapping of both nasal and temporal retinal axons along the anterior-posterior axis of the SC. This is actually observed in double mutant ephrin-A2$^{-/-}$ A5$^{-/-}$ homozygotes but a topographic bias of both nasal and temporal axons was still present, with the majority of temporal and nasal retinal axons being confined to their anterior and posterior tectal halfs, respectively (Feldheim, (2000), loc. cit.; Goodhill, Neuron 25 (2000), 501-3). These results point to a role of RGM as one of the additional factors required for mapping along the anterior-posterior axis. Such a role is supported by the graded anterior-low posterior-high expression of this molecule in the SC of mammals (Mueller, (1997), loc. cit.).

The zebrafish mutant acerebella (ace) is mutant in fgf8 and lacks the midbrain-hindbrain boundary region and the cerebellum (Reifers, Development 125 (1998), 2381-95; Picker, (1999), Ioc. cit.). As a result the tectum is much smaller in ace mutants than in wildtype and the expression levels of all three zebrafish A-ephrins are changed with ephrin-A2 and ephrin-A5a being still expressed at low and anterior levels in ace tecta and with ephrin-A5b being completely eliminated (Picker et al., 1999). In ace mutant tecta, mapping of retinal axons along the anterior-posterior axis is normal in dorsal tectum and is not completely lost in ventral tectum, suggesting the involvement of other graded guidance cues, not seriously affected by the fgf8 mutation in the ace zebrafish mutants (Picker et al., 1999). Dorsoventral patterning in both zebrafish ace mutants and ephrin-A2$^{-/-}$ A5$^{-/-}$ double knock out mice is affected.

RGM, with its graded expression along the anterior-posterior axis of the tectum and its ability to function in a secreted and membrane-coupled way, is an important player for topographic map formation.

EXAMPLE V

Materials and Methods

1. Patients 21 brains of patients with clinical history and neuropathologically confirmed diagnosis of focal cerebral infarctions and 25 brains of patients with traumatic brain injury were included in this study. Infarctioned brain tissue was derived from an updated stroke and trauma brain-bank (Table 1, 2) reported previously (Postler et al., 1997, Beschomer et al., 2000). Tissue specimen procurement was performed according to the ethical guidelines of the University of Tuebingen. Patients with altered immune status because of immunosuppressive therapy or meningitis/encephalitis were excluded from this study. As controls, the results were compared to tissue from corresponding areas of 4 normal non-ischemic brains described previously (Schwab et at., 2000). In addition to patient data, haematoxyline-eosine (HE), luxol fast blue (LFB) and iron (Fe) staining was used for evaluation of the typical histological features defined as standard indication of infarct (Kalimo et al., 1996) and trauma age (Graham and Gennarelli, 1996).

2. Immunohistochemistry

After formaldehyde fixation and paraffin-embedding, rehydrated 2:m sections were boiled (in a 600 W microwave oven) seven times for 5 min in citrate buffer (2.1 g sodium citrate/liter, pH 7.4). Endogenous peroxsidase was inhibited with 1% $H_2O_2$ in methanol (1:10; 15 min). Sections were incubated with 10% normal porcine serum (Biochrom, Berlin, FRG) to block non-specific binding of immunoglobulins. Monospecific polyclonal antibodies directed against RGM were diluted (1:10) in 1% BSA (bovine serum albumin) TBS (Tris-balanced salt solution, containing 0.025 M Tris, 0.15 M NaCI) and incubated over night at room temperature. Specific binding of the antibodies were detected with a secondary biotinylated swine anti-rabbit IgG F(ab)$_2$ antibody fragment 1:400 for 30 min (DAKO, Hamburg, FRG), followed by incubation with a peroxidase conjugated streptavidin-biotin complex (DAKO, Hamburg, FRG). The enzyme was visualized with diaminobenzidine as a chromogen (Fluka, Neu-Ulm, FRG). Sections were counterstained with Mayer's Hemalaun. Negative controls consisted of sections incubated in the absence of the primary antibody. Specificity of polyclonal RGM antibody was confirmed by inhibition of staining using human ischemic brain tissue after pre-incubation for 3 h on ice with access of the cognate RGM peptide.

3. Double Labeling Experiments

In double labelling experiments, a cell-type or activation specific antigen was first labelled using the ABC procedure in combination with alkaline phosphatase conjugates. Specific antigens were labelled with antibodies against GFAP (glial fibrillary acidic protein, monoclonal, Boehringer Mannheim, Germany, 1:100) to detect astrocytes, MBP (myelin basic protein, polyclonal, oligodendrocytes, Dako, 1:500) and CD68 (Dako, 1:100) for microglia/macrophage identification. Activated microglia/macrophages were detected with antibodies directed against HLA-DR, -DP, -DQ (MHC class II, DAKO, Glostrup, Denmark, 1:100) or MRP-8 (8-5C2, BMA, Augst, Switzerland, 1:100) (Postler et al., 1997). Lymphocytic subpopulations were classified with monoclonal antibodies against CD4 (T-helper lymphocytes, 1:10, Dako) and CD8 (T cytotoxic/suppressor lymphocytes, 1:500, Dako) and CD20 (pan B cell marker, 1:200, Dako). In order to detect extracellular basal lamina structures in vessels and during scar formation mouse laminin (1:500, Chemicon) antibodies were used and rabbit fibronectin (1:100, Dako) antibodies were used to detect matrix deposition. Furthermore, in order to characterize the cellular proliferation response, sections were incubated with the S phase specific PCNA (proliferating cell nuclear antigen, 1:100, Dako) monoclonal antibodies. Briefly, slices were deparaffinized, irradiated in a microwave oven for antigen retrieval and incubated with non specific porcine serum as described above. Visualization was achieved by adding biotinylated secondary antibodies (1:400) for 30 min and alkaline phosphatase conjugated ABC complex diluted 1:400 in TBS-BSA for 30 min. Consecutively, slices were developed with FastBlue BB salt chromogen-substrate solution yielding a blue reaction product. Between double labelling experiments, slices were irradiated in a microwave for 5 min in citrate buffer. Then RGM was immunodetected as described above.

4. Evaluation and Statistical Analysis

Data were calculated as means of labelled cells (MLC, ±SEM) from border zones or remote areas of the same tissue section and were compared to normal control brains using the two-tailed unpaired student's t-test. Border zones were defined as peri-lesional areas adjacent to the developing necrotic core demarcating the region of major damage. RGM$^+$ cells were counted in ten high power fields (HPF, ×200 magnification with an eye-piece-grid representing 0.25 mm$^2$).

Results 21 brains of patients with focal cerebral infarctions (FCI), 25 brains with traumatic brain injury (TBI) and 4 control brains were evaluated for RGM protein expression by immunohistochemistry.

1 Healthy, Neuropathological Unaltered Control Brains

In control brains without neuropathologically alterations, RGM immunoreactivity was detected on white matter fibres, oligodendrocytes, the perikarya of some neurons and RGM+ cells were also detected in the choroid plexus (FIG. 8) and ependyma. Only single cells were detected in peri-vascular spaces. Further, some smooth muscle cells and few endothelial cells but no astrocytes were labelled.

2 Focal Cerebral Ischemia (FCI)

It was analysed whether number and distribution of RGM expressing cells is altered after cerebral infarctions. Results suggested, that RGM expression is lesion-associated. Cellular RGM expression was confined to neurons, few reactive astrocytes and invading leukocytes. With the ageing of the lesions, RGM-positive extracellular laminae components were found in the constituting scar.

RGM-positive cells accumulated in infarctioned white matter, hemorrhagic areas, infarction core and peri-infarctional areas, respectively. Using the students t-test; a significantly (P<0.0001) higher number of RGM+ cells was detected in peri-infarcional areas (MLC=24, SEM=1.1) than in remote areas (MLC=2, SEM=0.2) or control tissue (MLC=6, SEM=0.8). The morphological described peri-infarctional areas were part of the physiologically defined penumbra. In these areas the number of RGM-positive cells accumulated already up to day 1 (p<0.0001, MLC=31.93, SEM=2.3) reached their maximum 1.5-2.5 days (MLC=34, SEM=3.2) after infarction and remained elevated up to several weeks and months of survival (MLC=11, SEM=1.4). Early after ischemic damage (up to 2.5 days), RGM immunoreactivity was predominantly found on neurons and leukocytes of granulocytic, monocytic and lymphocytic origin in vessels within ischemic tissue. Paralleled by edema formation, up to 1-7 days, RGM-positive cells were found extravasating outside the vascular walls into the focal ischemic lesioned parenchyma. In perivascular regions, RGM-positive cells formed clusters in the Virchow-Robin spaces from day 1-7, which subsided later. These peri-vascular cells, also referred to as adventitial or perithelial cells are characteristically alert immune cells (Kato and Walz, 2000; Streit et al., 1999). With lesion aging, from day 3 onwards, lesional RGM expression by few reactive astrocytes, was observed. At later stages, arising 1 week after infarction, extracellular RGM deposits were detected constituting neo-laminae localized to areas of ongoing scar formation. These RGM-positive laminae increased in magnitude and regional extend over time. With tissue reorganisation of the lesion, also "foamy", lipid loaded RGM-positive phagocytic RGM-positive microglia/macrophages were observed.

Upregulation of cellular RGM expression correlated with the time course and appearance of infiltrating leukocytes and activation of microglia/macrophages after injury (Stoll et al., 1998). Whereas upregulation of extracellular RGM expression correlated with the time course and the appearance of the scar after injury. In few cases (<5% of counterstained nuclei) some reactive astrocytes restricted to the demarcating lesion core also expressed RGM.

3. Traumatic Brain Injury

In patients who died after TBI, in accordance to cerebral infarction (FCI) the immunohistological evaluation revealed early cellular membranous, cytoplasmatic and nuclear RGM expression by leukocytes, few reactive astrocytes and neurons with strong staining of their perikarya, dendrites and axons (FIG. 9). During the observed time post TBI, within the necrotic core and the bordering peri-necrotic parenchyma accumulation of RGM-positive cells (p<0.0001) was detected in border zones (MLC=22, SEM=0.7) compared to remote areas (MLC=1, SEM=0.1) and normal brain controls (MLC=5.8, SEM=0.8). Following TBI, RGM-positive cell numbers arose already during the first 24 hours (p<0.0001) where RGM-positive cell numbers reached maximum levels (MLC=29, SEM=0.9) and decreased subsequently. With increasing time after TBI, most remarkable changes corresponded to areas of ongoing scar formation (FIG. 10). In these areas, well defined extracellular RGM-positive laminae were visible condensing adjacent to the border zone. RGM immunoreactivity was also detected in endothelial and vascular smooth muscle cells (SMC) but no significant differences were observed between injured and control brains.

References as mentioned in the example herein above:
Beschomer, Acta Neuropathol. 100 (2000), 377-384
Graham, "Greenfield's Neuropathology," DJ. Graham and P. L. Lantos (eds), 6th Edn., Edward Arnold, London (1996), pps. 197-248
Kalimo, "*Greenfield's Neuropathology,*" 6th Edn. Arnold, London Sydney Auckland (1996), pp 315-381.
Kato, Brain Pathol., 10 (2000), 137-143. Postler, Glia 19 (1997), 27-34.
Schwab, Acta Neuropathol. 99 (2000), 609-614.
Stoll, Prog. Neurobiol. 56 (1998), 149-171.
Streit, Prog. Neurobiol. 57 (1999), 563-581.

EXAMPLE VI

Change of Tumor Growth Behaviour in Mice

Hybridoma cells secreting the RGM-specific F3D4 monoclonal antibody were injected into the peritoneum of mice, primed with mineral oil. Normally the hybridoma cells continue to divide in the peritoneum and the hybridoma cells secreted large amounts of antibody, resulting in formation of large ascites tumors. Mice receiving the F3D4-producing hybridoma cells did not develop ascites tumors in the peritoneal cavity, but developed solid, adherent tumors. The F3D4 monoclonal antibody resulted in a change of phenotype of the tumorigenic hybridoma cells from a less invasive, nonadherent state to an invasive adherent state. Masking of endogeneous RGM by the antibodies secreted from the hybridoma cells, enabled adhesion and invasion of these tumor cells and was responsible for this outcome.

EXAMPLE VII

Detection of a Functional RGM Fragment

RGM was cloned into the pTriEx vector and the vector was cut inside the polylinker side and inside the RGM sequence using Sac1 in the first step. After ligation of both ends the RGM containing vector was cut in the second step with StuI inside the RGM sequence and in the polylinker with PmlI. After ligation of both ends, the vector with the shorter RGM-fragments was transfected into COST cells. Cell lysates of these COS cells were purified using an anti-RGM1 affinity column and RGM-containing fractions were used in collapse assay experiments. A fragment as described in SEQ ID NO:19 was active in said assays.

EXAMPLE VIII

Detection of Further RGMs

A publicly available computer database at the National Center for Biotechnology Information (NCBJ, USA) was used to identify human genes homologous to chicken RGM, employing the information and data illustrated in the examples herein above. A search strategy based on the Blast algorithm (NCBI) resulted in three human genes located on chromosomes 1, 5 and 15. The corresponding contigs are NT_021932.5 (RGM3), NT_029283.2 (RGM2) and NT_010370.5 (RGM1), respectively. cDNA sequences for RGM 1, 2 and 3 were derived from these genomic sequences by omitting introns and fusing the remaining exons.

Corresponding amino acid and nucleotide sequences for human RGM2 are illustrated in appended SEQ ID NOs: 22 and 23. Human RGM3-sequences are shown in SEQ ID NOs: 24 and 25.

---

The invention claimed is:

1. An isolated polypeptide comprising the amino acid sequence as set forth in SEQ ID NO: 18, 20, 23, 25 or an amino acid sequence having more than 90% identity over a full length of SEQ ID NO:18 or 25.

2. The isolated polypeptide of claim 1, comprising SEQ ID NO:18 or the amino acid sequence having more than 90% identity over the full length of SEQ ID NO:18.

3. The isolated polypeptide of claim 1, comprising SEQ ID NO: 20.

4. The isolated polypeptide of claim 1, comprising SEQ ID NO:23.

5. The isolated polypeptide of claim 1, comprising SEQ ID NO:25 or the amino acid sequence having more than 90% identity over the full length of SEQ ID NO:25.

* * * * *

SEQUENCE LISTING

```
<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: synthetic

<400> SEQUENCE: 1

Tyr Leu Gly Thr Thr Leu Val Val Arg
 1               5

<210> SEQ ID NO 2
<211> LENGTH: 7
<212> TYPE: PRT
<213> ORGANISM: Artificial Sequence
<220> FEATURE:
<223> OTHER INFORMATION: synthetic

<400> SEQUENCE: 2

Thr Phe Thr Asp Thr Phe Gln
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: synthetic

<400> SEQUENCE: 3

Met Pro Glu Glu Val Val Asn Ala Val Glu Asp Arg
 1               5                  10

<210> SEQ ID NO 4
<211> LENGTH: 6
<212> TYPE: PRT
<213> ORGANISM: Artificial Sequence
<220> FEATURE:
<223> OTHER INFORMATION: synthetic

<400> SEQUENCE: 4
```

```
Leu Thr Leu Leu Phe Lys
  1               5

<210> SEQ ID NO 5
<211> LENGTH: 10
<212> TYPE: PRT
<213> ORGANISM: Artificial Sequence
<220> FEATURE:
<223> OTHER INFORMATION: synthetic

<400> SEQUENCE: 5

Thr Phe Thr Asp Thr Phe Gln Thr Cys Lys
  1               5                  10

<210> SEQ ID NO 6
<211> LENGTH: 14
<212> TYPE: PRT
<213> ORGANISM: Artificial Sequence
<220> FEATURE:
<223> OTHER INFORMATION: synthetic

<400> SEQUENCE: 6

Gly Cys Pro Leu Asn Gln Gln Leu Asp Phe Gln Thr Met Arg
  1               5                  10

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Ala Glu Met Asp Glu
  1               5

<210> SEQ ID NO 8
<211> LENGTH: 7
<212> TYPE: PRT
<213> ORGANISM: Artificial Sequence
<220> FEATURE:
<223> OTHER INFORMATION: synthetic

<400> SEQUENCE: 8

Pro Glu Ala Phe Thr Tyr Glu
  1               5

<210> SEQ ID NO 9
<211> LENGTH: 5
<212> TYPE: PRT
<213> ORGANISM: Artificial Sequence
<220> FEATURE:
<223> OTHER INFORMATION: synthetic

<400> SEQUENCE: 9

His Leu Glu Tyr Arg
  1               5

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Gln Gly Leu Tyr Leu
  1               5
```

<210> SEQ ID NO 11
<211> LENGTH: 29
<212> TYPE: DNA
<213> ORGANISM: Artificial Sequence
<220> FEATURE:
<223> OTHER INFORMATION: synthetic

<400> SEQUENCE: 11
atgccagctg aaggaaggta gctgtagct                                    29

<210> SEQ ID NO 12
<211> LENGTH: 31
<212> TYPE: DNA
<213> ORGANISM: Artificial Sequence
<220> FEATURE:
<223> OTHER INFORMATION: synthetic

<400> SEQUENCE: 12
ttagctacag ctaccttcct tcagctggca t                                 31

<210> SEQ ID NO 13
<211> LENGTH: 30
<212> TYPE: DNA
<213> ORGANISM: Artificial Sequence
<220> FEATURE:
<223> OTHER INFORMATION: synthetic

<400> SEQUENCE: 13
gactacagct ttctcaagac agcttgctaa                                   30

<210> SEQ ID NO 14
<211> LENGTH: 30
<212> TYPE: DNA
<213> ORGANISM: Artificial Sequence
<220> FEATURE:
<223> OTHER INFORMATION: synthetic

<400> SEQUENCE: 14
ttagcaagct gtcttgagaa agctgtagtc                                   30

<210> SEQ ID NO 15
<211> LENGTH: 29
<212> TYPE: DNA
<213> ORGANISM: Artificial Sequence
<220> FEATURE:
<223> OTHER INFORMATION: synthetic

<400> SEQUENCE: 15
aactcaagca agcttagctg actttctca                                    29

<210> SEQ ID NO 16
<211> LENGTH: 29
<212> TYPE: DNA
<213> ORGANISM: Artificial Sequence
<220> FEATURE:
<223> OTHER INFORMATION: synthetic

<400> SEQUENCE: 16
tgagaaagtc agctaagctt gcttgagtt                                    29

<210> SEQ ID NO 17
<211> LENGTH: 1302
<212> TYPE: DNA
<213> ORGANISM: Artificial Sequence
<220> FEATURE:
<223> OTHER INFORMATION: synthetic

<400> SEQUENCE: 17

```
atgggtatgg ggagaggggc aggatccaca gccctgggac ttttccaaat cctccctgtc     60
tttctctgca tcttccctcc agtgacgtct ccatgcaaga tcctcaagtg caactctgag    120
ttctgggcgg ccacgtcggg ttcgcaccac ctgggcgcag aggaaacccc ggagttctgc    180
acggcgttgc gcgcctacgc gcactgcacc cgccgcaccg cccgcacctg caggggggac    240
ctggcctacc actcggccgt gcatggcata gacgatctca tggtgcaaca caactgctcc    300
aaggatggcc ccacgtccca gccccgcctc cggacattgc ccccggggga cagccaggag    360
cgctctgaca gccccgaaat ctgccactac gagaagagct tcacaaaca ctcggcagct    420
cccaactaca cccactgtgg gctcttcggg gaccccacc tcaggacttt cacggacacc    480
ttccagacct gcaaggtgca aggggcttgg ccgctcatag acaataacta cctgaacgtc    540
caggtcacca cacgccggt gctgcctggc tcctcagcca ccgccaccag caagctcacc    600
atcatcttca agagcttcca ggaatgcgtg agcagaaag tgtaccaggc agagatggac    660
gagctccctg ctgcctttgc tgatggctcc aagaacggcg gcgacaagca cggagccaac    720
agcctgaaga tcaccgagaa ggtgtcgggc agcacatcg agatccaggc caagtacatt    780
ggcaccacca tcgtggtgag gcaggtgggc cgctacctca ccttcgccgt cgtatgccg    840
gaggaggtgg tcaacgctgt ggaggaccgg acagtcagg gcctctacct gtgcctccgg    900
ggttgtccgc tcaaccaaca gattgacttc agactttcc gcttggctca ggccgctgag    960
ggccgtgctc gcaggaaggg gcccagcttg ccggccccc ctgaggcctt cacttacgag   1020
tcggccactg ccaagtgcag ggaaaagctg cccgtagagg acctctactt ccagtcctgc   1080
gtctttgacc tcctgactac gggggatgtc aacttcatgc tggctgctta ttacgctttt   1140
gaggacgtga agatgcttca ctccaacaaa gacaaactgc acctctatga aggacacgg   1200
gccctagccc cgggcaatgc agctcccctcg gagcatccct gggccctccc tgccctctgg   1260
gtagcactgc tgagtttgag tcagtgttgg ttgggtttgt ta                      1302
```

<210> SEQ ID NO 18
<211> LENGTH: 434
<212> TYPE: PRT
<213> ORGANISM: Gallus gallus

<400> SEQUENCE: 18

```
Met Gly Met Gly Arg Gly Ala Gly Ser Thr Ala Leu Gly Leu Phe Gln
  1               5                  10                  15

Ile Leu Pro Val Phe Leu Cys Ile Phe Pro Pro Val Thr Ser Pro Cys
                 20                  25                  30

Lys Ile Leu Lys Cys Asn Ser Glu Phe Trp Ala Ala Thr Ser Gly Ser
             35                  40                  45

His His Leu Gly Ala Glu Glu Thr Pro Glu Phe Cys Thr Ala Leu Arg
         50                  55                  60

Ala Tyr Ala His Cys Thr Arg Arg Thr Ala Arg Thr Cys Arg Gly Asp
 65                  70                  75                  80

Leu Ala Tyr His Ser Ala Val His Gly Ile Asp Asp Leu Met Val Gln
                 85                  90                  95

His Asn Cys Ser Lys Asp Gly Pro Thr Ser Gln Pro Arg Leu Arg Thr
            100                 105                 110

Leu Pro Pro Gly Asp Ser Gln Glu Arg Ser Asp Ser Pro Glu Ile Cys
        115                 120                 125

His Tyr Glu Lys Ser Phe His Lys His Ser Ala Ala Pro Asn Tyr Thr
```

|  | 130 |  |  |  |  | 135 |  |  |  |  | 140 |  |  |  |

His Cys Gly Leu Phe Gly Asp Pro His Leu Arg Thr Phe Thr Asp Thr
145                 150                 155                 160

Phe Gln Thr Cys Lys Val Gln Gly Ala Trp Pro Leu Ile Asp Asn Asn
            165                 170                 175

Tyr Leu Asn Val Gln Val Thr Asn Thr Pro Val Leu Pro Gly Ser Ser
        180                 185                 190

Ala Thr Ala Thr Ser Lys Leu Thr Ile Ile Phe Lys Ser Phe Gln Glu
            195                 200                 205

Cys Val Glu Gln Lys Val Tyr Gln Ala Glu Met Asp Glu Leu Pro Ala
210                 215                 220

Ala Phe Ala Asp Gly Ser Lys Asn Gly Gly Asp Lys His Gly Ala Asn
225                 230                 235                 240

Ser Leu Lys Ile Thr Glu Lys Val Ser Gly Gln His Ile Glu Ile Gln
            245                 250                 255

Ala Lys Tyr Ile Gly Thr Thr Ile Val Val Arg Gln Val Gly Arg Tyr
            260                 265                 270

Leu Thr Phe Ala Val Arg Met Pro Glu Glu Val Val Asn Ala Val Glu
        275                 280                 285

Asp Arg Asp Ser Gln Gly Leu Tyr Leu Cys Leu Arg Gly Cys Pro Leu
290                 295                 300

Asn Gln Gln Ile Asp Phe Gln Thr Phe Arg Leu Ala Gln Ala Ala Glu
305                 310                 315                 320

Gly Arg Ala Arg Arg Lys Gly Pro Ser Leu Pro Ala Pro Pro Glu Ala
            325                 330                 335

Phe Thr Tyr Glu Ser Ala Thr Ala Lys Cys Arg Glu Lys Leu Pro Val
        340                 345                 350

Glu Asp Leu Tyr Phe Gln Ser Cys Val Phe Asp Leu Leu Thr Thr Gly
        355                 360                 365

Asp Val Asn Phe Met Leu Ala Ala Tyr Tyr Ala Phe Glu Asp Val Lys
370                 375                 380

Met Leu His Ser Asn Lys Asp Lys Leu His Leu Tyr Glu Arg Thr Arg
385                 390                 395                 400

Ala Leu Ala Pro Gly Asn Ala Ala Pro Ser Glu His Pro Trp Ala Leu
            405                 410                 415

Pro Ala Leu Trp Val Ala Leu Leu Ser Leu Ser Gln Cys Trp Leu Gly
            420                 425                 430

Leu Leu

<210> SEQ ID NO 19
<211> LENGTH: 116
<212> TYPE: PRT
<213> ORGANISM: Gallus gallus

<400> SEQUENCE: 19

Glu Leu Pro Ala Ala Phe Ala Asp Gly Ser Lys Asn Gly Gly Asp Lys
1               5                   10                  15

His Gly Ala Asn Ser Leu Lys Ile Thr Glu Lys Val Ser Gly Gln His
            20                  25                  30

Ile Glu Ile Gln Ala Lys Tyr Ile Gly Thr Thr Ile Val Val Arg Gln
        35                  40                  45

Val Gly Arg Tyr Leu Thr Phe Ala Val Arg Met Pro Glu Glu Val Val
    50                  55                  60

Asn Ala Val Glu Asp Arg Asp Ser Gln Gly Leu Tyr Leu Cys Leu Arg
65                  70                  75                  80

Gly Cys Pro Leu Asn Gln Gln Ile Asp Phe Gln Thr Phe Arg Leu Ala
            85                  90                  95

Gln Ala Ala Glu Gly Arg Ala Arg Arg Lys Gly Pro Ser Leu Pro Ala
            100                 105                 110

Pro Pro Glu Ala
        115

<210> SEQ ID NO 20
<211> LENGTH: 434
<212> TYPE: PRT
<213> ORGANISM: Homo sapiens

<400> SEQUENCE: 20

Met Gly Met Gly Arg Gly Ala Gly Arg Ser Ala Leu Gly Phe Trp Pro
1               5                   10                  15

Thr Leu Ala Phe Leu Leu Cys Ser Phe Pro Ala Ala Thr Ser Pro Cys
            20                  25                  30

Lys Ile Leu Lys Cys Asn Ser Glu Phe Trp Ser Ala Thr Ser Gly Ser
        35                  40                  45

His Ala Pro Ala Ser Asp Asp Thr Pro Glu Phe Cys Ala Ala Leu Arg
    50                  55                  60

Ser Tyr Ala Leu Cys Thr Arg Arg Thr Ala Arg Thr Cys Arg Gly Asp
65                  70                  75                  80

Leu Ala Tyr His Ser Ala Val His Gly Ile Glu Asp Leu Met Ser Gln
                85                  90                  95

His Asn Cys Ser Lys Asp Gly Pro Thr Ser Gln Pro Arg Leu Arg Thr
            100                 105                 110

Leu Pro Pro Ala Gly Asp Ser Gln Glu Arg Ser Asp Ser Pro Glu Ile
        115                 120                 125

Cys His Tyr Glu Lys Ser Phe His Lys His Ser Ala Thr Pro Asn Tyr
    130                 135                 140

Thr His Cys Gly Leu Phe Gly Asp Pro His Leu Arg Thr Phe Thr Asp
145                 150                 155                 160

Arg Phe Gln Thr Cys Lys Val Gln Gly Ala Trp Pro Leu Ile Asp Asn
                165                 170                 175

Asn Tyr Leu Asn Val Gln Val Thr Asn Thr Pro Val Leu Pro Gly Ser
            180                 185                 190

Ala Ala Thr Ala Thr Ser Lys Leu Thr Ile Ile Phe Lys Asn Phe Gln
        195                 200                 205

Glu Cys Val Asp Gln Lys Val Tyr Gln Ala Glu Met Asp Glu Leu Pro
    210                 215                 220

Ala Ala Phe Val Asp Gly Ser Lys Asn Gly Gly Asp Lys His Gly Ala
225                 230                 235                 240

Asn Ser Leu Lys Ile Thr Glu Lys Val Ser Gly Gln His Val Glu Ile
                245                 250                 255

Gln Ala Lys Tyr Ile Gly Thr Thr Ile Val Val Arg Gln Val Gly Arg
            260                 265                 270

Tyr Leu Thr Phe Ala Val Arg Met Pro Glu Glu Val Val Asn Ala Val
        275                 280                 285

Glu Asp Trp Asp Ser Gln Gly Leu Tyr Leu Cys Leu Arg Gly Cys Pro
    290                 295                 300

Leu Asn Gln Gln Ile Asp Phe Gln Ala Phe His Thr Asn Ala Glu Gly
305                 310                 315                 320

Thr Gly Ala Arg Arg Leu Ala Ala Ala Ser Pro Ala Pro Thr Ala Pro
                325                 330                 335

Glu Thr Phe Pro Tyr Glu Thr Ala Val Ala Lys Cys Lys Glu Lys Leu
                340                 345                 350

Pro Val Glu Asp Leu Tyr Tyr Gln Ala Cys Val Phe Asp Leu Leu Thr
            355                 360                 365

Thr Gly Asp Val Asn Phe Thr Leu Ala Ala Tyr Ala Leu Glu Asp
        370                 375                 380

Val Lys Met Leu His Ser Asn Lys Asp Lys Leu His Leu Tyr Glu Arg
385                 390                 395                 400

Thr Arg Asp Leu Pro Gly Arg Ala Ala Ala Gly Leu Pro Leu Ala Pro
                405                 410                 415

Arg Pro Leu Leu Gly Ala Leu Val Pro Leu Leu Ala Leu Leu Pro Val
                420                 425                 430

Phe Cys

<210> SEQ ID NO 21
<211> LENGTH: 1305
<212> TYPE: DNA
<213> ORGANISM: Homo sapiens

<400> SEQUENCE: 21
atgggtatgg ggagaggggc aggacgttca gccctgggat tctggccgac cctcgccttc     60
cttctctgca gcttccccgc agccacctcc ccgtgcaaga tcctcaagtg caactctgag    120
ttctggagcg ccacgtcggg cagccacgcc ccagcctcag acgacacccc cgagttctgt    180
gcagccttgc gcagctacgc cctgtgcacg cggcggacgg cccgcacctg ccggggtgac    240
ctggcctacc actcggccgt ccatggcata gaggacctca tgagccagca caactgctcc    300
aaggatggcc ccacctcgca gccacgcctg cgcacgctcc accggccgg agacagccag    360 gagcgctcgg acagccccga gatctgccat tacgagaaga gctttcacaa gcactcggcc    420 accccccaact acacgcactg tggcctcttc gggacccac acctcaggac tttcaccgac    480
cgcttccaga cctgcaaggt gcagggcgcc tggccgctca tcgacaataa ttacctgaac    540
gtgcaggtca ccaacacgcc tgtgctgccc ggctcagcgg ccactgccac cagcaagctc    600
accatcatct tcaagaactt ccaggagtgt gtggaccaga aggtgtacca ggctgagatg    660
gacgagctcc cggccgcctt cgtggatggc tctaagaacg gtggggacaa gcacggggcc    720
aacagcctga agatcactga aaggtgtca ggccagcacg tggagatcca ggccaagtac    780
atcggcacca ccatcgtggt gcgccaggtg ggccgctacc tgacctttgc cgtccgcatg    840
ccagaggaag tggtcaatgc tgtggaggac tgggacagcc agggtctcta cctctgcctg    900
cggggctgcc ccctcaacca gcagatcgac ttccaggcct tccacaccaa tgctgagggc    960
accggtgccc gcaggctggc agccgccagc cctgcaccca gcccccga gaccttccca   1020 tacgagacag ccgtggccaa gtgcaaggag aagctgccgg tggaggacct gtactaccag   1080
gcctgcgtct tcgacctcct caccacgggc gacgtgaact tcacactggc cgcctactac   1140
gcgttggagg atgtcaagat gctccactcc aacaaagaca aactgcacct gtatgagagg   1200
actcgggacc tgccaggcag ggcggctgcg ggctgccc tggcccccg ccctcctg   1260 ggcgccctcg tcccgctcct ggccctgctc cctgtgttct gctag              1305

<210> SEQ ID NO 22
<211> LENGTH: 1314
<212> TYPE: DNA
<213> ORGANISM: Homo sapiens

<400> SEQUENCE: 22

-continued

```
atgggcttga gagcagcacc ttccagcgcc gccgctgccg ccgccgaggt tgagcagcgc    60
cgcagccccg ggctctgccc ccgccgctg  gagctgctgc tgctgctgct gttcagcctc   120
gggctgctcc acgcaggtga ctgccaacag ccagcccaat gtcgaatcca gaaatgcacc   180
acggacttcg tgtccctgac ttctcacctg aactctgccg ttgacggctt tgactctgag   240
ttttgcaagg ccttgcgtgc ctatgctggc tgcacccagc gaacttcaaa agcctgccgt   300
ggcaacctgg tataccattc tgccgtgttg ggtatcagtg acctcatgag ccagaggaat   360
tgttccaagg atggacccac atcctctacc aaccccgaag tgacccatga tccttgcaac   420
tatcacagcc acgctggagc cagggaacac aggagagggg accagaaccc tcccagttac   480
cttttttgtg gcttgtttgg agatcctcac ctcagaactt caaggataa  cttccaaaca   540
tgcaaagtag aaggggcctg ccactcata  gataataatt atctttcagt tcaagtgaca   600
aacgtacctg tggtccctgg atccagtgct actgctacaa ataagatcac tattatcttc   660
aaagcccacc atgagtgtac agatcagaaa gtctaccaag ctgtgacaga tgacctgccg   720
gccgcctttg tggatggcac caccagtggt ggggacagcg atgccaagag cctgcgtatc   780
gtggaaaggg agagtggcca ctatgtggag atgcacgccc gctatatagg gaccacagtg   840
tttgtgcggc aggtgggtcg ctacctgacc cttgccatcc gtatgcctga gacctggcc   900
atgtcctacg aggagagcca ggacctgcag ctgtgcgtga acggctgccc cctgagtgaa   960
cgcatcgatg acgggcaggg ccaggtgtct gccatcctgg acacagcct  gcctcgcacc  1020
tccttggtgc aggcctggcc tggctacaca ctggagactg ccaacactca atgccatgag  1080
aagatgccag tgaaggacat ctatttccag tcctgtgtct tcgacctgct caccactggt  1140
gatgccaact ttactgccgc agcccacagt gccttggagg atgtggaggc cctgcaccca  1200
aggaaggaac gctggcacat tttccccagc agtggcaatg ggactccccg tggaggcagt  1260
gatttgtctg tcagtctagg actcacctgc ttgatcctta tcgtgttttt gtag         1314
```

<210> SEQ ID NO 23
<211> LENGTH: 437
<212> TYPE: PRT
<213> ORGANISM: Homo sapiens

<400> SEQUENCE: 23

```
Met Gly Leu Arg Ala Ala Pro Ser Ser Ala Ala Ala Ala Ala Ala Glu
  1               5                  10                  15

Val Glu Gln Arg Arg Ser Pro Gly Leu Cys Pro Pro Leu Glu Leu
                 20                  25                  30

Leu Leu Leu Leu Leu Phe Ser Leu Gly Leu Leu His Ala Gly Asp Cys
         35                   40                  45

Gln Gln Pro Ala Gln Cys Arg Ile Gln Lys Cys Thr Thr Asp Phe Val
     50                  55                  60

Ser Leu Thr Ser His Leu Asn Ser Ala Val Asp Gly Phe Asp Ser Glu
 65                  70                  75                  80

Phe Cys Lys Ala Leu Arg Ala Tyr Ala Gly Cys Thr Gln Arg Thr Ser
                 85                  90                  95

Lys Ala Cys Arg Gly Asn Leu Val Tyr His Ser Ala Val Leu Gly Ile
                100                 105                 110

Ser Asp Leu Met Ser Gln Arg Asn Cys Ser Lys Asp Gly Pro Thr Ser
            115                 120                 125

Ser Thr Asn Pro Glu Val Thr His Asp Pro Cys Asn Tyr His Ser His
        130                 135                 140
```

```
Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
            165                 170                 175

Asn Phe Gln Thr Cys Lys Val Glu Gly Ala Trp Pro Leu Ile Asp Asn
        180                 185                 190

Asn Tyr Leu Ser Val Gln Val Thr Asn Val Pro Val Pro Gly Ser
    195                 200                 205

Ser Ala Thr Ala Thr Asn Lys Ile Thr Ile Ile Phe Lys Ala His His
210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
            260                 265                 270

Ala Arg Tyr Ile Gly Thr Thr Val Phe Val Arg Gln Val Gly Arg Tyr
        275                 280                 285

Leu Thr Leu Ala Ile Arg Met Pro Glu Asp Leu Ala Met Ser Tyr Glu
290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
            340                 345                 350

Thr Ala Asn Thr Gln Cys His Glu Lys Met Pro Val Lys Asp Ile Tyr
        355                 360                 365

Phe Gln Ser Cys Val Phe Asp Leu Leu Thr Thr Gly Asp Ala Asn Phe
370                 375                 380

Thr Ala Ala Ala His Ser Ala Leu Glu Asp Val Glu Ala Leu His Pro
385                 390                 395                 400

Arg Lys Glu Arg Trp His Ile Phe Pro Ser Ser Gly Asn Gly Thr Pro
                405                 410                 415

Arg Gly Gly Ser Asp Leu Ser Val Ser Leu Gly Leu Thr Cys Leu Ile
            420                 425                 430

Leu Ile Val Phe Leu
        435

<210> SEQ ID NO 24
<211> LENGTH: 1272
<212> TYPE: DNA
<213> ORGANISM: Homo sapiens

<400> SEQUENCE: 24
atgggccagt cccctagtcc caggtcctcc catggcagtc ccccaactct aagcactctc    60
actctcctgc tgctcctctg tggacatgct cattctcaat gcaagatcct ccgctgcaat    120
gctgagtacg tatcgtccac tctgagcctt agaggtgggg gttcatcagg agcacttcga    180
ggaggaggag gaggaggccg gggtggaggg gtgggctctg gcggcctctg tcgagccctc    240
cgctcctatg cgctctgcac tcggcgcacc ggccgcacct gccgcgggga cctcgccttc    300
cattcggcgg tacatggcat cgaagacctg atgatccagc acaactgctc ccgccagggc    360
cctacagccc ctccccgcc ccggggcccc gccttccag gcgcgggctc cggcctcccc    420
gccccggacc cttgtgacta tgaaggccgg ttttcccggc tgcatggtcg tccccggggg    480
```

```
ttcttgcatt gcgcttcctt cggggacccc catgtgcgca gcttccacca tcactttcac      540
acatgccgtg tccaaggagc ttggcctcta ctggataatg acttcctctt tgtccaagcc      600
accagctccc ccatggcgtt gggggccaac gctaccgcca cccggaagct caccatcata      660
tttaagaaca tgcaggaatg cattgatcag aaggtgtatc aggctgaggt ggataatctt      720
cctgtagcct ttgaagatgg ttctatcaat ggaggtgacc gacctggggg atccagtttg      780
tcgattcaaa ctgctaaccc tgggaaccat gtggagatcc aagctgccta cattggcaca      840
actataatca ttcggcagac agctgggcag ctctccttct ccatcaaggt agcagaggat      900
gtggccatgg ccttctcagc tgaacaggac ctgcagctct gtgttggggg gtgccctcca      960
agtcagcgac tctctcgatc agagcgcaat cgtcggggag ctataaccat tgatactgcc     1020
agacggctgt gcaaggaagg gcttccagtg gaagatgctt acttccattc ctgtgtcttt     1080
gatgttttaa tttctggtga tcccaacttt accgtggcag ctcaggcagc actggaggat     1140
gcccgagcct tcctgccaga cttagagaag ctgcatctct tcccctcaga tgctggggtt     1200
cctctttcct cagcaaccct cttagctcca ctcctttctg ggctctttgt tctgtggctt     1260
tgcattcagt aa                                                         1272
```

<210> SEQ ID NO 25
<211> LENGTH: 423
<212> TYPE: PRT
<213> ORGANISM: Homo sapiens

<400> SEQUENCE: 25

```
Met Gly Gln Ser Pro Ser Pro Arg Ser Ser His Gly Ser Pro Pro Thr
 1               5                  10                  15

Leu Ser Thr Leu Thr Leu Leu Leu Leu Cys Gly His Ala His Ser
             20                  25                  30

Gln Cys Lys Ile Leu Arg Cys Asn Ala Glu Tyr Val Ser Ser Thr Leu
         35                  40                  45

Ser Leu Arg Gly Gly Gly Ser Ser Gly Ala Leu Arg Gly Gly Gly Gly
     50                  55                  60

Gly Gly Arg Gly Gly Gly Val Gly Ser Gly Gly Leu Cys Arg Ala Leu
 65                  70                  75                  80

Arg Ser Tyr Ala Leu Cys Thr Arg Arg Thr Ala Arg Thr Cys Arg Gly
                 85                  90                  95

Asp Leu Ala Phe His Ser Ala Val His Gly Ile Glu Asp Leu Met Ile
            100                 105                 110

Gln His Asn Cys Ser Arg Gln Gly Pro Thr Ala Pro Pro Pro Pro Arg
        115                 120                 125

Gly Pro Ala Leu Pro Gly Ala Gly Ser Gly Leu Pro Ala Pro Asp Pro
    130                 135                 140

Cys Asp Tyr Glu Gly Arg Phe Ser Arg Leu His Gly Arg Pro Pro Gly
145                 150                 155                 160

Phe Leu His Cys Ala Ser Phe Gly Asp Pro His Val Arg Ser Phe His
                165                 170                 175

His His Phe His Thr Cys Arg Val Gln Gly Ala Trp Pro Leu Leu Asp
            180                 185                 190

Asn Asp Phe Leu Phe Val Gln Ala Thr Ser Ser Pro Met Ala Leu Gly
        195                 200                 205

Ala Asn Ala Thr Ala Thr Arg Lys Leu Thr Ile Ile Phe Lys Asn Met
    210                 215                 220

Gln Glu Cys Ile Asp Gln Lys Val Tyr Gln Ala Glu Val Asp Asn Leu
```

-continued

```
225                 230                 235                 240

Pro Val Ala Phe Glu Asp Gly Ser Ile Asn Gly Gly Asp Arg Pro Gly
                245                 250                 255

Gly Ser Ser Leu Ser Ile Gln Thr Ala Asn Pro Gly Asn His Val Glu
                260                 265                 270

Ile Gln Ala Ala Tyr Ile Gly Thr Thr Ile Ile Ile Arg Gln Thr Ala
                275                 280                 285

Gly Gln Leu Ser Phe Ser Ile Lys Val Ala Glu Asp Val Ala Met Ala
                290                 295                 300

Phe Ser Ala Glu Gln Asp Leu Gln Leu Cys Val Gly Gly Cys Pro Pro
305                 310                 315                 320

Ser Gln Arg Leu Ser Arg Ser Glu Arg Asn Arg Arg Gly Ala Ile Thr
                325                 330                 335

Ile Asp Thr Ala Arg Arg Leu Cys Lys Glu Gly Leu Pro Val Glu Asp
                340                 345                 350

Ala Tyr Phe His Ser Cys Val Phe Asp Val Leu Ile Ser Gly Asp Pro
                355                 360                 365

Asn Phe Thr Val Ala Ala Gln Ala Ala Leu Glu Asp Ala Arg Ala Phe
                370                 375                 380

Leu Pro Asp Leu Glu Lys Leu His Leu Phe Pro Ser Asp Ala Gly Val
385                 390                 395                 400

Pro Leu Ser Ser Ala Thr Leu Leu Ala Pro Leu Leu Ser Gly Leu Phe
                405                 410                 415

Val Leu Trp Leu Cys Ile Gln
                420
```